United States Patent [19]
Takagaki et al.

[11] Patent Number: 5,525,595
[45] Date of Patent: Jun. 11, 1996

[54] 3- OR 4-GLYCOSYLOXYBENZOPYRAN DERIVATIVE AND ANTIALLERGIC AGENT CONTAINING THE DERIVATIVE AS ACTIVE INGREDIENT

[75] Inventors: Hidetsugu Takagaki; Masayoshi Abe; Yasuo Aoki; Yoshiyuki Sano; Mitsuru Sakai; Nobuyuki Kimura, all of Chiba, Japan

[73] Assignee: Dainippon Ink and Chemicals, Inc., Tokyo, Japan

[21] Appl. No.: 312,192

[22] Filed: Sep. 26, 1994

[30] Foreign Application Priority Data

Sep. 28, 1993 [JP] Japan .................................. 5-241136
Sep. 28, 1993 [JP] Japan .................................. 5-241137

[51] Int. Cl.⁶ ............................................. A61K 31/70
[52] U.S. Cl. .................... 514/27; 514/25; 514/826; 514/829; 514/885; 514/455; 514/457; 536/1.1; 536/4.1; 536/18.1
[58] Field of Search ........................ 514/25, 27, 826, 514/829, 885, 455

[56] References Cited

U.S. PATENT DOCUMENTS 4,845,121  4/1989  Witiak et al. ........................ 514/455

FOREIGN PATENT DOCUMENTS

598117A1  5/1994  European Pat. Off. .

OTHER PUBLICATIONS

Synthetic aci–Reductones: 3,4–Dihydroxy–2H–1–benzopyran–2–ones and Their cis– and trans–4a,5,6,7,8,8a–Hexahydro Diastereomers. Antiaggregatory, Antilipidemic, and Redox Properties Compared to Those of the 4–Substituted 2–Hydroxytetronic Acids–Donald T. Witiak, et al–American Chemical Society 1988, pp. 1437–1445.

*Primary Examiner*—Douglas W. Robinson
*Assistant Examiner*—James O. Wilson
*Attorney, Agent, or Firm*—Armstrong, Westerman, Hattori, McLeland & Naughton

[57] ABSTRACT

There are provided novel compounds of the formulae I and II:

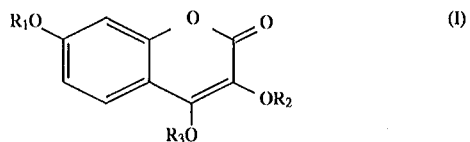

(I)

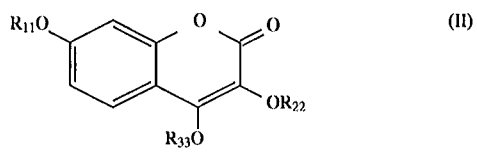

(II)

and their physiologically acceptable salts. The compounds according to the present invention and their physiologically acceptable salts exhibit an antiallergic activity and are useful for treating allergic diseases.

38 Claims, No Drawings

3- OR 4-GLYCOSYLOXYBENZOPYRAN DERIVATIVE AND ANTIALLERGIC AGENT CONTAINING THE DERIVATIVE AS ACTIVE INGREDIENT

FIELD OF THE INVENTION

This invention relates to 3- or 4-glycosyloxybenzopyran derivatives which are obtained by glycosylation reaction of the 3- or 4-position hydroxyl group of a benzopyran derivative with a hexose derivative. These compounds or physiologically acceptable salts thereof are useful as antiallergic agents.

BACKGROUND OF THE INVENTION

Benzopyran derivatives as the aglycon moiety of the 3- or 4-glycosyloxybenzopyran derivatives of the present invention have been disclosed for example in EP-A-0598117 by the present inventors, and similar benzopyran derivatives for example in *J. Med. Chem.*, vol.31, pp.1473–1445, 1988, by Donald T. Witiak and in U.S. Pat. No. 4,845,121, but nothing about the 3- or 4-glycosyloxybenzopyran derivatives as their 3- or 4-position glycosides. In addition to this, nothing is known about the antiallergic activity of the 3- or 4-glycosyloxybenzopyran derivatives of the present invention and physiologically acceptable salts thereof.

Since antiallergic agents so far available commercially are not satisfactory in terms of efficiency, safety and bioavailability, studies on the development of antiallergic agents have been carried out extensively. For example, a typical antiallergic agent, Tranilast (general name), requires high-dose administration for care of allergic disease, though its acute toxicity value ($LD_{50}$) in mice is low (780 mg/kg), hence causing a problem of requiring caution at the time of its use because of the closeness between quantities of its efficacy and toxicity, namely its narrow safety range. Also, Disodium Cromoglicate (general name) as a well known antiasthamtic agent whose efficacy has been confirmed clinically is satisfactory in terms of its toxicity, but must be used by spray inhalation due to its extremely poor gastrointestinal absorbability. In addition, these known antiallergic agents are not effective on delayed type allergy, though they are effective on immediate type allergy. Chronic state of allergic diseases including asthma and atopic dermatitis is a serious problem, and the delayed type allergy is deeply concerned in the development of the chronic state. In consequence, a drug which is effective on both immediate type allergy and delayed type allergy is desirable as an antiallergic agent. As it is universally known, steroid is effective on both immediate type allergy and delayed type allergy but cause extremely serious side effects.

As has been described above, most of the antiallergic agents so far reported have various disadvantages, because they cannot show sufficient therapeutic effect because of the lack of efficacy on delayed type allergy, they are low in safety due to their narrow safety range, or their administration method is limited because of their poor gastrointestinal absorbability. In consequence, great concern has been directed toward the development of a drug which can be used in oral administration, has low toxicity and is effective on both immediate and delayed type allergies.

The inventors of the present invention have provided, by EP-A-0598117, a benzopyran derivative and an antiallergy agent which comprises the derivative as an active ingredient. This time, taking the aforementioned problems involved in the prior art into consideration, we contemplate providing a novel substance more useful as a drug and an antiallergic agent having low toxicity and excellent effect.

SUMMARY OF THE INVENTION

With the aim of providing a compound more useful as a drug, the inventors of the present invention have synthesized various glycosylated compounds of the benzopyran derivative disclosed in EP-A-0598117 by glycosylating its 3- or 4-position hydroxyl group with a hexose derivative and examined their antiallergic activity and safety. As the result, the present inventors have found that a 3-glycosyloxybenzopyran derivative represented by the following formula (I) and a 4-glycosyloxybenzopyran derivative represented by the following formula (II) are capable of showing markedly excellent antiallergic activity with low toxicity. The present invention has been accomplished on the basis of this finding. Accordingly, the present invention relates to a 3-glycosyloxybenzopyran derivative represented by the following formula (I)

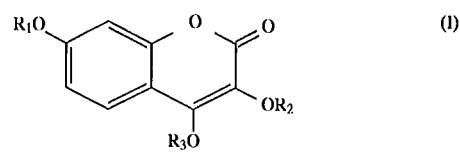

wherein $R_1$ is a hydrogen atom, an alkyl group, an alkenyl group, an aralkyl group or an acyl group, $R_2$ is a glycosyl group whose hydroxyl group is protected or not protected, selected from the group consisting of glucosyl, mannosyl and galactosyl groups, and $R_3$ is a hydrogen atom or a benzyl group, to physiologically acceptable salts thereof and to an antiallergic agent which comprises the 3-glycosyloxybenzopyran derivative represented by the above formula (I) or a physiologically acceptable salt thereof as an active ingredient.

The present invention also relates to a 4-glycosyloxybenzopyran derivative represented by the following formula (II)

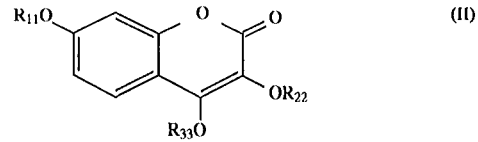

wherein $R_{11}$ is a hydrogen atom, an alkyl group, an alkenyl group, an aralkyl group or an acyl group, $R_{22}$ is a hydrogen atom or an acyl group and $R_{33}$ is a glycosyl group whose hydroxyl group is protected or not protected, selected from the group consisting of glucosyl, mannosyl and galactosyl groups, to physiologically acceptable salts thereof and to an antiallergic agent which comprises the 4-glycosyloxybenzopyran derivative represented by the above formula (II) or a physiologically acceptable salt thereof as an active ingredient.

DETAILED DESCRIPTION OF THE INVENTION

Firstly, the 3-glycosyloxybenzopyran derivative represented by the formula (I) is described.

In the formula (I) of the present invention, $R_1$ is a hydrogen atom, an alkyl group, an alkenyl group, an aralkyl group or an acyl group.

Illustrative examples of the alkyl group include straight- or branched-chain alkyl groups such as methyl, ethyl, propyl, isopropyl, n-butyl, s-butyl, t-butyl, n-pentyl, 2-methyl-pentyl, octyl, decyl, dodecyl and the like alkyl groups preferably having 1 to 12, more preferably 3 to 12, most preferably 6 to 10, carbon atoms.

Illustrative examples of the alkenyl group include straight- or branched-chain alkenyl groups such as vinyl, propenyl, pentenyl, hexenyl, heptenyl, octenyl, nonyl, decenyl, 3-methyl-2-butenyl, geranyl and the like alkenyl groups preferably having 2 to 10, more preferably 6 to 10, carbon atoms.

Illustrative examples of the aralkyl group include those to be used as hydroxyl group protecting groups such as benzyl group or a benzyl group which may have a substituent group (p-methoxybenzyl, p-methylbenzyl, p-chlorobenzyl or p-nitrobenzyl for instance) and the like, of which unsubstituted benzyl group is particularly preferred.

Illustrative examples of the acyl group include alkanoyl groups such as acetyl, propionyl, butylyl, isobutylyl and the like groups, aroyl groups such as benzoyl group or a benzoyl group which may have a substituent group (p-methoxybenzoyl, p-methylbenzoyl, p-chlorobenzoyl or p-nitrobenzoyl for instance) and the like and acyl groups such as an alkoxycarbonyl group (methoxycarbonyl or ethoxycarbonyl for instance) and the like, of which an acyl group having 2 to 7 carbon atoms is particularly preferred.

The glycosyl group represented by $R_2$ is selected from glucosyl, mannosyl and galactosyl groups whose hydroxyl groups may or may not be protected with a protecting group. In general, saccharides are known to have D and L stereoisomers which are also included in the present invention. The hexose derivatives to be used as the material of glycosyl groups are glucose, mannose and galactose whose hydroxyl groups may or may not be protected with a protecting group. The compound of the present invention, 3-glycosyloxybenzopyran derivative, is a compound in which any of these hexose derivatives is linked to the 3-position of a benzopyran derivative through glycoside bonding. Such a glycoside bonding may include $\alpha$- and $\beta$-binding types, and both of these binding types are included in the 3-glycosyloxybenzopyran derivative of the present invention.

With regard to the glycosyl group which is protected with a protecting group, preferred examples of the protecting group include those usually used as saccharide protecting groups such as acyl, benzyl and the like groups. In this case, illustrative examples of the acyl group include alkanoyl groups such as acetyl, propionyl, butylyl, isobutylyl and the like groups, aroyl groups such as benzoyl group or a benzoyl group which may have a substituent group (p-methoxybenzoyl, p-methylbenzoyl, p-chlorobenzoyl or p-nitrobenzoyl for instance) and the like and an alkoxycarbonyl group (methoxycarbonyl or ethoxycarbonyl for instance) and the like, of which an acyl group having 2 to 7 carbon atoms is particularly preferred. Though it varies depending on the type of the substituent groups of $R_1$ and $R_3$, galactose may be used as most preferred glycosyl group, followed by glucose and mannose in that order. Also, an unprotected glycosyl group is more preferable than its protected counterpart.

Illustrative examples of $R_3$ include hydrogen atom and benzyl group.

From the viewpoint of antiallergic activity, preferred examples of the 3-glycosyloxybenzopyran derivative of the present invention include a compound in which $R_1$ is an alkyl group, $R_2$ is glucosyl group and $R_3$ is hydrogen, a compound in which $R_1$ is an alkenyl group, $R_2$ is glycosyl group and $R_3$ is hydrogen, a compound in which $R_1$ is an alkyl group, $R_2$ is galactosyl group and $R_3$ is hydrogen and a compound in which $R_1$ is an alkenyl group, $R_2$ is galactosyl group and $R_3$ is hydrogen.

Next, the 4-glycosyloxybenzopyran derivative represented by the formula (II) of the present invention is described.

In the formula (II), $R_{11}$ is a hydrogen atom, an alkyl group, an alkenyl group, an aralkyl group or an acyl group.

Illustrative examples of the alkyl group include straight- or branched-chain alkyl groups such as methyl, ethyl, propyl, isopropyl, n-butyl, s-butyl, t-butyl, n-pentyl, 2-methylpentyl, octyl, decyl, dodecyl and the like alkyl groups preferably having 1 to 12, more preferably 3 to 12, most preferably 6 to 10, carbon atoms.

Illustrative examples of the alkenyl group include straight- or branched-chain alkenyl groups such as vinyl, propenyl, pentenyl, hexenyl, heptenyl, octenyl, nonyl, decenyl, 3-methyl-2-butenyl, geranyl and the like alkenyl groups preferably having 2 to 10, more preferably 6 to 10, carbon atoms.

Illustrative examples of the aralkyl group include those to be used as hydroxyl group protecting groups such as benzyl group or a benzyl group which may have a substituent group (p-methoxybenzyl, p-methylbenzyl, p-chlorobenzyl or p-nitrobenzyl for instance) and the like, of which unsubstituted benzyl group is particularly preferred.

Illustrative examples of the acyl group include alkanoyl groups such as acetyl, propionyl, butylyl, isobutylyl and the like groups, aroyl groups such as benzoyl group or a benzoyl group which may have a substituent group (p-methoxybenzoyl, p-methylbenzoyl, p-chlorobenzoyl or p-nitrobenzoyl for instance) and the like and acyl groups such as an alkoxycarbonyl group (methoxycarbonyl or ethoxycarbonyl for instance) and the like, of which an acyl group having 2 to 7 carbon atoms is particularly preferred.

$R_{22}$ is a hydrogen atom or an acyl group. In this case, illustrative examples of the acyl group include alkanoyl groups such as acetyl, propionyl, butylyl, isobutylyl and the like groups, aroyl groups such as benzoyl group or a benzoyl group which may have a substituent group (p-methoxybenzoyl, p-methylbenzoyl, p-chlorobenzoyl or p-nitrobenzoyl for instance) and the like and an alkoxycarbonyl group (methoxycarbonyl or ethoxycarbonyl for instance) and the like, of which an acyl group having 2 to 7 carbon atoms is particularly preferred.

The glycosyl group represented by $R_{33}$ is selected from glucosyl, mannosyl and galactosyl groups whose hydroxyl groups may or may not be protected with a protecting group. In general, saccharides are known to have D and L stereoisomers which are also included in the present invention. The hexose derivatives to be used as the material of glycosyl groups are glucose, mannose and galactose whose hydroxyl groups may or may not be protected with a protecting group. The compound of the present invention, 4-glycosyloxybenzopyran derivative, is a compound in which any of these hexose derivatives is linked to the 4-position of a benzopyran derivative through glycoside bonding. Such a glycoside bonding may include $\alpha$- and $\beta$-binding types, and both of these binding types are included in the 4-glycosyloxybenzopyran derivative of the present invention.

With regard to the glycosyl group which is protected with a protecting group, preferred examples of the protecting group include those usually used as saccharide protecting groups such as acyl, benzyl and the like groups. In this case, illustrative examples of the acyl group include alkanoyl groups such as acetyl, propionyl, butylyl, isobutylyl and the like groups, aroyl groups such as benzoyl group or a benzoyl group which may have a substituent group (p-methoxybenzoyl, p-methylbenzoyl, p-chlorobenzoyl or p-nitrobenzoyl for instance) and the like and an alkoxycarbonyl group (methoxycarbonyl or ethoxycarbonyl for instance) and the like, of which an acyl group having 2 to 7 carbon atoms is particularly preferred.

Though it varies depending on the type of the substituent groups of $R_{11}$ and $R_{22}$, galactose may be used as most preferred glycosyl group, followed by glucose and mannose in that order. Also, an unprotected glycosyl group is more preferable than its protected counterpart.

From the viewpoint of antiallergic activity, preferred examples of the 4-glycosyloxybenzopyran derivative of the present invention include a compound in which $R_{11}$ is an alkyl group, $R_{22}$ is hydrogen and $R_{33}$ is glucosyl group, a compound in which $R_{11}$ is an alkenyl group, $R_{22}$ is hydrogen and $R_{33}$ is glucosyl group, a compound in which $R_{11}$ is an alkyl group, $R_{22}$ is hydrogen and $R_{33}$ is galactosyl group and a compound in which $R_{11}$ is an alkenyl group, $R_{22}$ is hydrogen and $R_{33}$ is galactosyl group.

The following summarizes a process for the production of the 3-glycosyloxybenzopyran derivative of the present invention.

The 3-glycosyloxybenzopyran derivative of the present invention represented by the formula (I) can be produced for example in the following manner in accordance with the following reaction scheme:

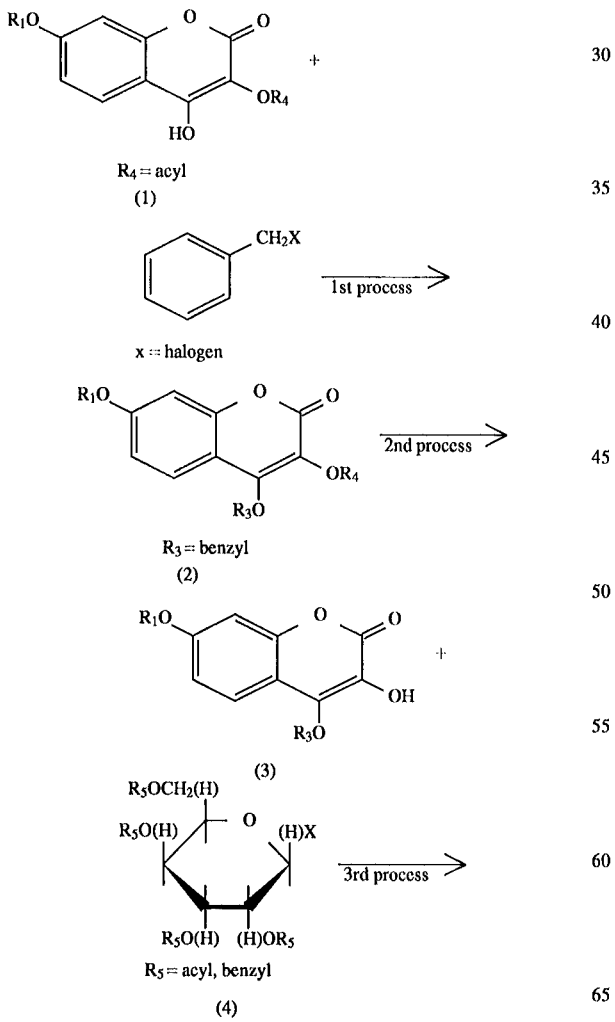

wherein, $R_1$ represents a hydrogen atom, an alkyl group, an alkenyl group, an aralkyl group or an acyl group, $R_3$ represents a benzyl group, $R_4$ represents an acyl group, $R_5$ represents a protecting group of acyl, benzyl or the like group, and X represents a halogen atom.

As a first step, the hydroxyl group at the 4-position of a 3-acyloxybenzopyran derivative (1) disclosed by the present inventors in a prior application (EP-A-0598117) is protected to obtain a compound (2). In this case, benzyl group may be used preferably as the protecting group. The reaction may be carried out by usually used benzylation reaction, for example, making use of benzyl chloride, benzyl bromide or the like as a benzylating agent and sodium carbonate, potassium carbonate or the like carbonate as a base or sodium hydride, potassium hydride or the like metal hydride as a basic substance. The reaction may be carried out in an organic solvent. Preferred examples of the solvent include ether solvents such as tetrahydrofuran, diethyl ether, dioxane and the like and amide solvents such as N,N-dimethylformamide and the like. The reaction may be carried out at a temperature of from 0° to 100° C., preferably from 40° to 70° C., for a period of generally from 1 to 5 hours.

A process for the production of the benzopyran derivative (1) to be used herein as a starting material is described in detail in EP-A-0598117. Namely, this derivative can be produced in accordance with the following reaction scheme:

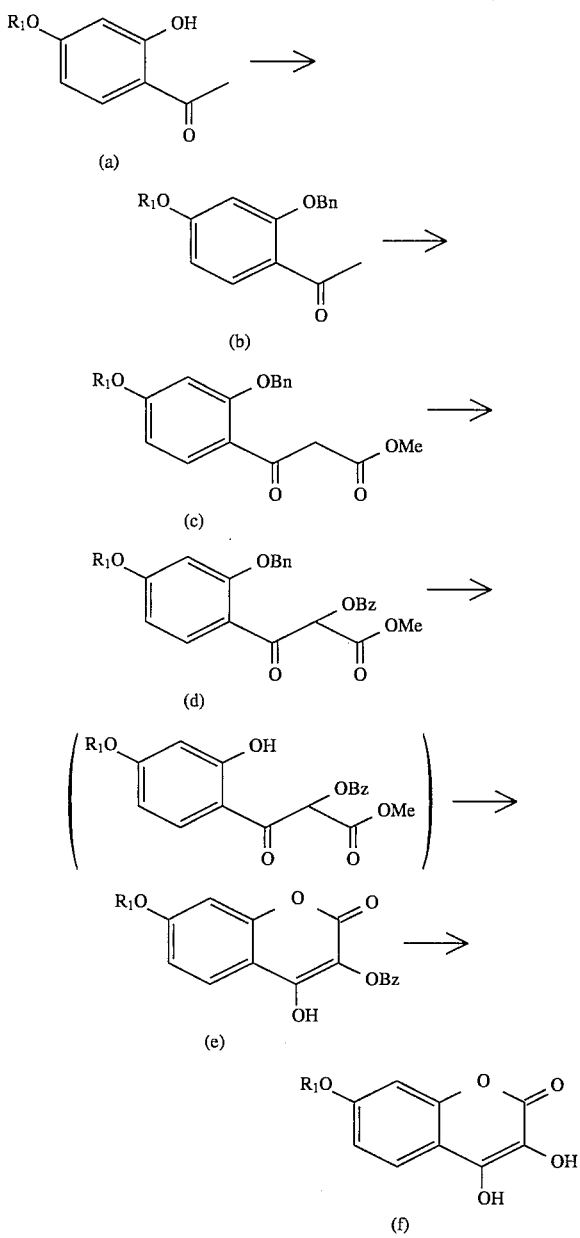

wherein, $R_1$ represents a hydrogen atom, an alkyl group, an alkenyl group, an aralkyl group or an acyl group, Bn represents benzyl group and Bz represents benzoyl group.

Firstly, when $R_1$ is hydrogen atom, hydroxyl group of 2,4-dihydroxyacetophenone (a) is protected with benzyl group to obtain a compound (b). Next, carbon atoms of the thus obtained compound are increased by its reaction with dimethyl carbonate to convert it into a diketone compound (c) which is subsequently allowed to react with benzoyl peroxide to obtain a compound (d). At this stage, the benzyl group used as a hydroxyl group protecting group is deblocked by catalytic reduction and then treated with an acid to obtain a benzoyloxy compound (e). The thus obtained benzoyloxy compound (e) is then treated with a metal alkoxide in a non-aqueous system to effect elimination of benzoyl group, thereby obtaining a benzopyran derivative (f).

When $R_1$ is an alkyl, alkenyl or aralkyl group, a 2-hydroxyacetophenone derivative whose 4-position hydroxyl group is protected with an alkyl, alkenyl or aralkyl group is used in stead of the 2,4-dihydroxyacetophenone (a). In the case of an alkenyl group, conversion into the alkenyl group can be made by using 2-hydroxyacetophenone whose 4-position hydroxyl group is protected with an alkynyl group and subjecting it to reduction in the course of the synthesis.

When $R_1$ is an acyl group, the acyl group may be introduced selectively into hydroxyl group on the benzene ring of the compound (f).

Next, as a second step, deacylation of the thus obtained compound (2) is carried out. The reaction may be effected by usual hydrolysis under basic condition. Preferred examples of the base to be used include hydroxides such as sodium hydroxide, potassium hydroxide, calcium hydroxide and the like and alcholate bases such as sodium methoxide, sodium ethoxide, potassium methoxide, potassium ethoxide and the like. The reaction may be carried out in a solvent. Preferred examples of the solvent include water, alcohol solvents such as methanol, ethanol, propanol and the like, ether solvents such as tetrahydrofuran, diethyl ether, dioxane and the like and amide solvents such as N,N-dimethylformamide and the like. The reaction may be carried out at a temperature of from 0° to 100° C., preferably from 10° to 40° C., for a period of from 1 to 5 hours.

Next, as a third step, the thus obtained compound represented by the formula (3) and a hexose halide derivative represented by the formula (4) are subjected to glycosylation reaction. Each of the hexose halide derivatives can be prepared in accordance with a known method (cf. L. J. Haynes and F. H. Newth, *Adv. Carbohydr. Chem.*, 10, 207 (1955); W. Korytnyk and J. A. Mills, *J. Chem. Soc.*, 1959, 636).

The glycosylation reaction can be effected by the known Koenigs-Knorr method in which a silver salt is used. In this reaction, an organic solvent is used as a reaction solvent. Preferred examples of the solvent include ether solvents such as diethyl ether, tetrahydrofuran, dimethoxyethane, dioxane and the like, amide solvents such as dimethylformamide, dimethylacetamide and the like and nitrile solvents such as acetonitrile, propionitrile and the like. The reaction may be carried out at a temperature of from −20° to 50° C., preferably from 0° to 30° C., for a period of generally from 5 to 30 hours.

In addition, when a compound whose 4-position is hydroxyl group is synthesized, elimination of benzyl in the formula (5) is carried out as a fourth step. This reaction is effected by hydrocracking in an atmosphere of hydrogen gas making use of a metal catalyst. Examples of the metal catalyst include palladium, platinum and the like catalysts which may be used in an amount of from 1 to 10% by weight based on the compound represented by the formula (5). The reaction in hydrogen gas may be carried out under a pressurized condition or under normal pressure. The reaction may be carried out generally in a solvent. Preferred examples of the solvent include alcohol solvents such as methanol, ethanol, propanol, butanol and the like, ether solvents such as diethyl ether, tetrahydrofuran, dioxane and the like and acetic ester solvents such as methyl acetate, ethyl acetate, propyl acetate and the like. The reaction may be carried out at a temperature of from −10° to 50° C., preferably from 0° to 30° C., for a period of generally from 1 to 5 hours. In this manner, the 3-glycosyloxybenzopyran derivative of the formula (6) is obtained.

When a compound having unprotected hydroxyl group on its glycosyl group is synthesized, deblocking reaction is carried out as a fifth step by debenzylation or deacylation of the hexose moiety, which can be attained in the usual way. That is, debenzylation can be carried out according to the aforementioned method, and deacylation can be effected by allowing the compound to react with a base as a deacylation agent which may be selected from hydroxides such as sodium hydroxide, potassium hydroxide, lithium hydroxide and the like and alkolate bases such as sodium methoxide, potassium methoxide, sodium ethoxide, potassium ethoxide and the like. Preferred examples of the reaction solvent to be used in this reaction include lower alcohols such as methanol, ethanol, propanol and the like, ether solvents such as diethyl ether, tetrahydrofuran, dimethoxyethane, dioxane and the like and amide solvents such as N,N-dimethylformamide, N,N-dimethylacetamide and the like. The reaction temperature varies depending on the reaction reagent and solvent to be used and is within the range of preferably from $-10°$ to $50°$ C., more preferably from $0°$ to $30°$ C. The reaction time is generally from 1 to 5 hours.

The following summarizes a process for the production of the 4-glycosyloxybenzopyran derivative of the present invention.

The 4-glycosyloxybenzopyran derivative of the present invention represented by the formula (II) can be produced for example in accordance with the following reaction scheme:

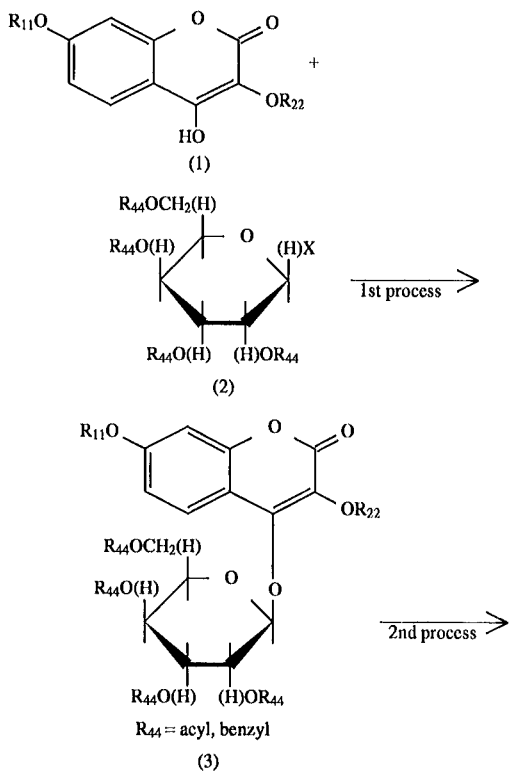

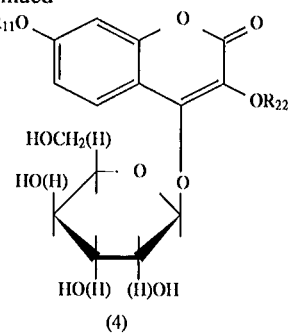

wherein, $R_{11}$ represents a hydrogen atom, an alkyl group, an alkenyl group, an aralkyl group or an acyl group, $R_{22}$ represents a hydrogen atom or an acyl group, $R_{44}$ represents an acyl group or a benzyl group as a protecting group of hydroxyl group of a hexose derivative, and X represents a halogen atom.

As a first step, the benzopyran derivative (1) disclosed in EP-A-0598117 and the hexose halide derivative represented by the formula (2) are subjected to glycosylation reaction. Processes for the production of these hexose halide and benzopyran derivatives are as described in the foregoing.

Using the thus obtained benzopyran derivative (1) and the hexose derivative (2), glycosylation of the 4-position hydroxyl group is carried out in accordance with the known Koenigs-Knorr method. In this glycosylation reaction, a metal catalyst may be used in order to accelerate the reaction, such as a silver salt, preferably silver oxide, silver carbonate or the like. In this reaction, an organic solvent is used as a reaction solvent. Preferred examples of the solvent include ether solvents such as diethyl ether, tetrahydrofuran, dimethoxyethane, dioxane and the like, amide solvents such as dimethylformamide, dimethylacetamide and the like and nitrile solvents such as acetonitrile, propionitrile and the like. The reaction may be carried out at a temperature of from $-20°$ to $50°$ C., preferably from $0°$ to $30°$ C., for a period of generally from 1 to 5 hours. In this way, the 4-glycosyloxybenzopyran derivative of the formula (3) is obtained.

When a compound having unprotected hydroxyl group on its glycosyl group is synthesized, deblocking reaction is carried out as a second step by debenzylation or deacylation of the hexose moiety in the formula (3), which can be attained in the usual way. That is, in the case of debenzylation, the reaction is effected by hydrocracking in an atmosphere of hydrogen gas making use of a metal catalyst. Examples of the metal catalyst include palladium, platinum and the like catalysts which may be used in an amount of from 1 to 10% by weight based on the compound represented by the formula (3). The reaction in hydrogen gas may be carried out under a pressurized condition or under normal pressure. The reaction may be carried out generally in a solvent. Preferred examples of the solvent include alcohol solvents such as methanol, ethanol, propanol, butanol and the like, ether solvents such as diethyl ether, tetrahydrofuran, dioxane and the like and acetic ester solvents such as methyl acetate, ethyl acetate, propyl acetate and the like. The reaction may be carried out at a temperature of from $-10°$ to $50°$ C., preferably from $0°$ to $30°$ C., for a period of generally from 1 to 5 hours. Also, deacylation can be effected by allowing the compound to react with a base as a deacylation agent which may be selected from hydroxides such as sodium hydroxide, potassium hydroxide, lithium hydroxide and the like and alkolate bases such as sodium methoxide, potassium methoxide, sodium ethoxide, potassium ethoxide and the like. Preferred examples of the reaction solvent to be used in this reaction include lower alcohols such as methanol, ethanol, propanol and the like, ether solvents such as diethyl ether, tetrahydrofuran, dimethoxyethane, dioxane and the like and amide solvents such as dimethylformamide, dimethylacetamide and the like. The reaction temperature varies depending on the reaction reagent and solvent to be used and is within the range of preferably from −10° to 50° C., more preferably from 0° to 30° C. The reaction time is generally from 1 to 5 hours.

The following compounds are illustrative examples of the thus obtained 3- or 4-glycosyloxybenzopyran derivatives of the present invention:

4,7-dihydroxy-3-(β-D-glucopyranosyloxy)-2H-1-benzopyran-2-one
7-methoxy-4-hydroxy-3-(β-D-glucopyranosyloxy)-2H-1-benzopyran-2-one
7-ethoxy-4-hydroxy-3-(β-D-glucopyranosyloxy)-2H-1-benzopyran-2-one
7-butoxy-4-hydroxy-3-(β-D-glucopyranosyloxy)-2H-1-benzopyran-2-one
7-octyloxy-4-hydroxy-3-(β-D-glucopyranosyloxy)-2H-1-benzopyran-2-one
7-decanyloxy-4-hydroxy-3-(β-D-glucopyranosyloxy)-2H-1-benzopyran-2-one
7-undecanyloxy-4-hydroxy-3-(β-D-glucopyranosyloxy)-2H-1-benzopyran-2-one
7-isopropoxy-4-hydroxy-3-(β-D-glucopyranosyloxy)-2H-1-benzopyran-2-one
7-(3-hexenyloxy)-4-hydroxy-3-(β-D-glucopyranosyloxy)-2H-1-benzopyran-2-one
7-geranyloxy-4-hydroxy-3-(β-D-glucopyranosyloxy)-2H-1-benzopyran-2-one
7-benzoyloxy-4-hydroxy-3-(β-D-glucopyranosyloxy)-2H-1-benzopyran-2-one
7-methoxy-4-hydroxy-3-(α-D-mannopyranosyloxy)-2H-1-benzopyran-2-one
7-ethoxy-4-hydroxy-3-(α-D-mannopyranosyloxy)-2H-1-benzopyran-2-one
7-butoxy-4-hydroxy-3-(α-D-mannopyranosyloxy)-2H-1-benzopyran-2-one
7-octyloxy-4-hydroxy-3-(α-D-mannopyranosyloxy)-2H-1-benzopyran-2-one
7-decanyloxy-4-hydroxy-3-(α-D-mannopyranosyloxy)-2H-1-benzopyran-2-one
7-undecanyloxy-4-hydroxy-3-(α-D-mannopyranosyloxy)-2H-1-benzopyran-2-one
7-isopropoxy-4-hydroxy-3-(α-D-mannopyranosyloxy)-2H-1-benzopyran-2-one
7-(3-hexenyloxy)-4-hydroxy-3-(α-D-mannopyranosyloxy)-2H-1-benzopyran-2-one
7-geranyloxy-4-hydroxy-3-(α-D-mannopyranosyioxy)-2H-1-benzopyran-2-one
7-benzoyloxy-4-hydroxy-3-(α-D-mannopyranosyloxy)-2H-1-benzopyran-2-one
7-acetoxy-4-hydroxy-3-(α-D-mannopyranosyloxy)-2H-1-benzopyran-2-one
4,7-dihydroxy-3-(β-D-galactopyranosyloxy)-2H-1-benzopyran-2-one
7-methoxy-4-hydroxy-3-(tetra-O-acetyl-β-D-galactopyranosyloxy)-2H-1-benzopyran- 2-one
7-methoxy-4-hydroxy-3-(β-D-galactopyranosyloxy)-2H-1-benzopyran-2-one
7-ethoxy-4-hydroxy-3-(β-D-galactopyranosyloxy)-2H-1-benzopyran-2-one
7-butoxy-4-hydroxy-3-(β-D-galactopyranosyloxy)-2H-1-benzopyran-2-one
7-octyloxy-4-hydroxy-3-(α-D-galactopyranosyloxy)-2H-1-benzopyran-2-one
7-decanyloxy-4-hydroxy-3-(β-D-galactopyranosyloxy)-2H-1-benzopyran-2-one
7-undecanyloxy-4-hydroxy-3-(β-D-galactopyranosyloxy)-2H-1-benzopyran-2-one
7-isopropoxy-4-hydroxy-3-(β-D-galactopyranosyloxy)-2H-1-benzopyran-2-one
7-(3-hexenyloxy)-4-hydroxy-3-(β-D-galactopyranosyloxy)-2H-1-benzopyran-2-one
7-geranyloxy-4-hydroxy-3-(β-D-galactopyranosyloxy)-2H-1-benzopyran-2-one
7-benzoyloxy-4-hydroxy-3-(β-D-galactopyranosyloxy)-2H-1-benzopyran-2-one
7-hydroxy-4-benzyloxy-3-(β-D-glucopyranosyloxy)-2H-1-benzopyran-2-one
4,7-dibenzyloxy-3-(β-D-glucopyranosyloxy)-2H-1-benzopyran-2-one
7-methoxy-4-benzyloxy-3-(β-D-glucopyranosyloxy)-2H-1-benzopyran-2-one
7-ethoxy-4-benzyloxy-3-(β-D-glucopyranosyloxy)-2H-1-benzopyran-2-one
7-butoxy-4-benzyloxy-3-(β-D-glucopyranosyloxy)-2H-1-benzopyran-2-one
7-octyloxy-4-benzyloxy-3-(β-D-glucopyranosyloxy)-2H-1-benzopyran-2-one
7-decanyloxy-4-benzyloxy-3-(β-D-glucopyranosyloxy)-2H-1-benzopyran-2-one
7-undecanyloxy-4-benzyloxy-3-(β-D-glucopyranosyloxy)-2H-1-benzopyran-2-one
7-isopropoxy-4-benzyloxy-3-(β-D-glucopyranosyloxy)-2H-1-benzopyran-2-one
7-(3-hexenyloxy)-4-benzyloxy-3-(β-D-glucopyranosyloxy)-2H-1-benzopyran-2-one
7-geranyloxy-4-benzyloxy-3-(β-D-glucopyranosyloxy)-2H-1-benzopyran-2-one
7-benzoyloxy-4-benzyloxy-3-(β-D-glucopyranosyloxy)-2H-1-benzopyran-2-one
4,7-dibenzyloxy-3-(α-D-mannopyranosyloxy)-2H-1-benzopyran-2-one
7-methoxy-4-benzyloxy-3-(α-D-mannopyranosyloxy)-1-benzopyran-2-one
7-ethoxy-4-benzyloxy-3-(α-D-mannopyranosyloxy)-2H-1-benzopyran-2-one
7-butoxy-4-benzyloxy-3-(α-D-mannopyranosyloxy)-2H-1-benzopyran-2-one
7-octyloxy-4-benzyloxy-3-(α-D-mannopyranosyloxy)-1-benzopyran-2-one
7-decanyloxy-4-benzyloxy-3-(α-D-mannopyranosyloxy)-2H-1-benzopyran-2-one
7-undecanyloxy-4-benzyloxy-3-(α-D-mannopyranosyloxy)-2H-1-benzopyran-2-one
7-isopropoxy-4-benzyloxy-3-(α-D-mannopyranosyloxy)-2H-1-benzopyran-2-one
7-(3-hexenyloxy)-4-benzyloxy-3-(α-D-mannopyranosyloxy)-2H-1-benzopyran-2-one
7-geranyloxy-4-benzyloxy-3-(α-D-mannopyranosyloxy)-2H-1-benzopyran-2-one
7-benzoyloxy-4-benzyloxy-3-(α-D-mannopyranosyloxy)-2H-1-benzopyran-2-one
7-acetoxy-4-benzyloxy-3-(α-D-mannopyranosyloxy)-1-benzopyran-2-one
4,7-dibenzyloxy-3-(β-D-galactopyranosyloxy)-2H-1-benzopyran-2-one
7-methoxy-4-benzyloxy-3-(tetra-O-acetyl-β-D-galactopyranosyloxy)-2H-1-benzopyran- 2-one 7-methoxy-4-benzyloxy-3-(β-D-galactopyranosyloxy)-2H-1-benzopyran-2-one
7-ethoxy-4-benzyloxy-3-(β-D-galactopyranosyloxy)-2H-1-benzopyran-2-one
7-butoxy-4-benzyloxy-3-(β-D-galactopyranosyloxy)-2H-1-benzopyran-2-one
7-octyloxy-4-benzyloxy-3-(α-D-galactopyranosyloxy)-2H-1-benzopyran-2-one
7-decanyloxy-4-benzyloxy-3-(β-D-galactopyranosyloxy)-2H-1-benzopyran-2-one
7-undecanyloxy-4-benzyloxy-3-(β-D-galactopyranosyloxy)-2H-1-benzopyran-2-one
7-isopropoxy-4-benzyloxy-3-(β-D-galactopyranosyloxy)-2H-1-benzopyran-2-one
7-(3-hexenyloxy)-4-benzyloxy-3-(β-D-galactopyranosyloxy)-2H-1-benzopyran-2-one
7-geranyloxy-4-benzyloxy-3-(β-D-galactopyranosyloxy)-2H-1-benzopyran-2-one
7-benzoyloxy-4-benzyloxy-3-(β-D-galactopyranosyloxy)-2H-1-benzopyran-2-one
3,7-diacetoxy-4-(tetra-O-acetyl-β-D-glucopyranosyloxy)-2H-1-benzopyran-2-one
3,7-dihydroxy-4-(β-D-glucopyranosyloxy)-2H-1-benzopyran-2-one
7-methoxy-3-acetoxy-4-(tetra-O-acetyl-β-D-glucopyranosyloxy)-2H-1-benzopyran-2-one
7-methoxy-3-hydroxy-4-(β-D-glucopyranosyloxy)-2H-1-benzopyran-2-one
7-ethoxy-3-hydroxy-4-(β-D-glucopyranosyloxy)-2H-1-benzopyran-2-one
7-butoxy-3-hydroxy-4-(β-D-glucopyranosyloxy)-2H-1-benzopyran-2-one
7-octyloxy-3-hydroxy-4-(β-D-glucopyranosyloxy)-2H-1-benzopyran-2-one
7-decanyloxy-3-hydroxy-4-(β-D-glucopyranosyloxy)-2H-1-benzopyran-2-one
7-undecanyloxy-3-hydroxy-4-(β-D-glucopyranosyloxy)-2H-1-benzopyran-2-one
7-isopropoxy-3-hydroxy-4-(β-D-glucopyranosyloxy)-2H-1-benzopyran-2-one
7-(3-hexenyloxy)-3-hydroxy-4-(β-D-glucopyranosyloxy)-2H-1-benzopyran-2-one
7-geranyloxy-3-hydroxy-4-(β-D-glucopyranosyloxy)-2H-1-benzopyran-2-one
7-benzoyloxy-3-hydroxy-4-(β-D-glucopyranosyloxy)-2H-1-benzopyran-2-one
7-ethoxy-3-acetoxy-4-(tetra-O-acetyl-β-D-glucopyranosyloxy)-2H-1-benzopyran-2-one
7-isopropoxy-3-acetoxy-4-(tetra-O-acetyl-β-D-glucopyranosyloxy)-2H-1-benzopyran-2-one
7-butoxy-3-acetoxy-4-(tetra-O-benzoyl-β-D-glucopyranosyloxy)-2H-1-benzopyran-2-one
7-butoxy-3-acetoxy-4-(β-D-glucopyranosyloxy)-2H-1-benzopyran-2-one
7-dodecanyloxy-3-acetoxy-4-(tetra-O-benzyl-β-D-glucopyranosyloxy)-2H-1-benzopyran-2-one
7-dodecanyloxy-3-acetoxy-4-(β-D-glucopyranosyloxy)-2H-1-benzopyran-2-one
7-(3-hexenyloxy)-3-acetoxy-4-(tetra-O-acetyl-β-D-glucopyranosyloxy)-2H-1-benzopyran-2-one
3,7-dipropynyloxy-4-(tetra-O-acetyl-β-D-glucopyranosyloxy)-2H-1-benzopyran-2-one
7-methoxy-3-propynyloxy-4-(tetra-O-acetyl-β-D-glucopyranosyloxy)-2H-1-benzopyran-2-one
7-methoxy-3-benzoyloxy-4-(tetra-O-acetyl-α-D-glucopyranosyloxy)-2H-1-benzopyran-2-one
7-ethoxy-3-propynyloxy-4-(tetra-O-acetyl-β-D-glucopyranosyloxy)-2H-1-benzopyran-2-one
7-isopropoxy-3-propynyloxy-4-(tetra-O-acetyl-β-D-glucopyranosyloxy)-2H-1-benzopyran-2-one
7-(3-hexenyloxy)-3-propynyloxy-4-(tetra-O-acetyl-β-D-glucopyranosyloxy)-2H-1-benzopyran-2-one
7-geranyloxy-3-propynyloxy-4-(tetra-O-acetyl-β-D-glucopyranosyloxy)-2H-1-benzopyran-2-one
7-octyloxy-3-acetoxy-4-(tetra-O-acetyl-β-D-glucopyranosyloxy)-2H-1-benzopyran-2-one
7-decanyloxy-3-acetoxy-4-(tetra-O-acetyl-β-D-glucopyranosyloxy)-2H-1-benzopyran-2-one
7-undecanyloxy-3-acetoxy-4-(tetra-O-acetyl-β-D-glucopyranosyloxy)-2H-1-benzopyran-2-one
7-geranyloxy-3-acetoxy-4-(tetra-O-acetyl-β-D-glucopyranosyloxy)-2H-1-benzopyran-2-one
3,7-dibenzoyloxy-4-(tetra-O-acetyl-β-D-glucopyranosyloxy)-2H-1-benzopyran-2-one
7-methoxy-3-benzoyloxy-4-(tetra-O-acetyl-β-D-glucopyranosyloxy)-2H-1-benzopyran-2-one
7-methoxy-3-benzoyloxy-4-(tetra-O-benzyl-β-D-glucopyranosyloxy)-2H-1-benzopyran-2-one
7-methoxy-3-benzoyloxy-4-(β-D-glucopyranosyloxy)-2H-1-benzopyran-2-one
7-ethoxy-3-benzoyloxy-4-(tetra-O-acetyl-β-D-glucopyranosyloxy)-2H-1-benzopyran-2-one
7-isopropoxy-3-benzoyloxy-4-(tetra-O-acetyl-β-D-glucopyranosyloxy)-2H-1-benzopyran-2-one
7-octyloxy-3-benzoyloxy-4-(tetra-O-acetyl-β-D-glucopyranosyloxy)-2H-1-benzopyran-2-one
7-decanyloxy-3-benzoyloxy-4-(tetra-O-acetyl-β-D-glucopyranosyloxy)-2H-1-benzopyran-2-one
7-undecanyloxy-3-benzoyloxy-4-(tetra-O-acetyl-β-D-glucopyranosyloxy)-2H-1-benzopyran-2-one
7-benzyloxy-3-benzoyloxy-4-(tetra-O-acetyl-β-D-glucopyranosyloxy)-2H-1-benzopyran-2-one
7-benzyloxy-3-hydroxy-4-(β-D-glucopyranosyloxy)-2H-1-benzopyran-2-one
7-acetoxy-3-benzyloxy-4-(tetra-O-benzyl-β-D-glucopyranosyloxy)-2H-1-benzopyran-2-one
7-acetoxy-3-hydroxy-4-(β-D-glucopyranosyloxy)-2H-1-benzopyran-2-one
3,7-diacetoxy-4-(tetra-O-acetyl-β-D-mannopyranosyloxy)-2H-1-benzopyran-2-one
3,7-dihydroxy-4-(α-D-mannopyranosyloxy)-2H-1-benzopyran-2-one
7-methoxy-3-acetoxy-4-(tetra-O-acetyl-α-D-mannopyranosyloxy)-2H-1-benzopyran-2-one
7-methoxy-3-hydroxy-4-(α-D-mannopyranosyloxy)-2H-1-benzopyran-2-one
7-ethoxy-3-hydroxy-4-(α-D-mannopyranosyloxy)-2H-1-benzopyran-2-one
7-butoxy-3-hydroxy-4-(α-D-mannopyranosyloxy)-2H-1-benzopyran-2-one
7-octyloxy-3-hydroxy-4-(α-D-mannopyranosyloxy)-2H-1-benzopyran-2-one
7-decanyloxy-3-hydroxy-4-(α-D-mannopyranosyloxy)-2H-1-benzopyran-2-one
7-undecanyloxy-3-hydroxy-4-(α-D-mannopyranosyloxy)-2H-1-benzopyran-2-one
7-isopropoxy-3-hydroxy-4-(α-D-mannopyranosyloxy)-2H-1-benzopyran-2-one
7-(3-hexenyloxy)-3-hydroxy-4-(α-D-mannopyranosyloxy)-2H-1-benzopyran-2-one
7-geranyloxy-3-hydroxy-4-(α-D-mannopyranosyloxy)-2H-1-benzopyran-2-one
7-benzoyloxy-3-hydroxy-4-(α-D-mannopyranosyloxy)-2H-1-benzopyran-2-one
7-ethoxy-3-acetoxy-4-(tetra-O-acetyl-α-D-mannopyranosyloxy)-2H-1-benzopyran-2-one 7-ethoxy-3-acetoxy-4-(tetra-O-benzyl-α-D-mannopyranosyloxy)-2H-1-benzopyran-2-one
7-isopropoxy-3-acetoxy-4-(tetra-O-acetyl-α-D-mannopyranosyloxy)-2H-1-benzopyran-2-one
7-butoxy-3-acetoxy-4-(tetra-O-benzoyl-α-D-mannopyranosyloxy)-2H-1-benzopyran-2-one
7-butoxy-3-acetoxy-4-(α-D-mannopyranosyloxy)-2H-1-benzopyran-2-one
7-dodecanyloxy-3-acetoxy-4-(tetra-O-benzyl-α-D-mannopyranosyioxy)-2H-1-benzopyran-2-one
7-dodecanyloxy-3-acetoxy-4-(α-D-mannopyranosyloxy)-2H-1-benzopyran-2-one
7-(3-hexenyloxy)-3-acetoxy-4-(tetra-O-acetyl-α-D-mannopyranosyloxy)-2H-1-benzopyran-2-one
3,7-dipropynyloxy-4-(tetra-O-acetyl-α-D-mannopyranosyloxy)-2H-1-benzopyran-2-one
7-methoxy-3-propynyloxy-4-(tetra-O-acetyl-α-D-mannopyranosyloxy )-2H-1-benzopyran-2-one
7-methoxy-3-benzoyloxy-4-(tetra-O-acetyl-α-D-mannopyranosyl)-2H-1-benzopyran-2-one
7-ethoxy-3-propynyloxy-4-(tetra-O-acetyl-α-D-mannopyranosyloxy)-2H-1-benzopyran-2-one
7-isopropoxy-3-propynyloxy-4-(tetra-O-acetyl-α-D-mannopyranosyloxy)-2H-1-benzopyran-2-one
7-(3-hexenyloxy)-3-propynyloxy-4-(tetra-O-acetyl-α-D-mannopyranosyloxy)-2H-1-benzopyran-2-one
7-geranyloxy-3-propynyloxy-4-(tetra-O-acetyl-α-D-mannopyranosyloxy)-2H-1-benzopyran-2-one
7-octyloxy-3-acetoxy-4-(tetra-O-acetyl-α-D-mannopyranosyloxy)-2H-1-benzopyran-2-one
7-decanyloxy-3-acetoxy-4-(tetra-O-acetyl-α-D-mannopyranosyloxy)-2H-1-benzopyran-2-one
7-undecanyloxy-3-acetoxy-4-(tetra-O-acetyl-α-D-mannopyranosyloxy)-2H-1-benzopyran-2-one
7-geranyloxy-3-acetoxy-4-(tetra-O-acetyl-α-D-mannopyranosyloxy)-2H-1-benzopyran-2-one
3,7-dibenzoyloxy-4-(tetra-O-acetyl-α-D-mannopyranosyioxy)-2H-1-benzopyran-2-one
7-methoxy-3-benzoyloxy-4-(tetra-O-acetyl-α-D-mannopyranosyloxy)-2H-1-benzopyran-2-one
7-methoxy-3-benzoyloxy-4-(tetra-O-benzyl-α-D-mannopyranosyloxy)-2H-1-benzopyran-2-one
7-methoxy-3-benzoyloxy-4-(α-D-mannopyranosyloxy)-2H-1-benzopyran-2-one
7-ethoxy-3-benzoyloxy-4-(tetra-O-acetyl-α-D-mannopyranosyloxy)-2H-1-benzopyran-2-one
7-isopropoxy-3-benzoyloxy-4-(tetra-O-acetyl-α-D-mannopyranosyloxy)-2H-1-benzopyran-2-one
7-octyloxy-3-benzoyloxy-4-(tetra-O-acetyl-α-D-mannopyranosyloxy)-2H-1-benzopyran-2-one
7-decanyloxy-3-benzoyloxy-4-(tetra-O-acetyl-α-D-mannopyranosyloxy)-2H-1-benzopyran-2-one
7-undecanyloxy-3-benzoyloxy-4-(tetra-O-acetyl-α-D-mannopyranosyloxy)-2H-1-benzopyran-2-one
7-benzyloxy-3-benzoyloxy-4-(tetra-O-acetyl-α-D-mannopyranosyloxy)-2H-1-benzopyran-2-one
7-benzyloxy-3-hydroxy-4-(α-D-mannopyranosyloxy)-2H-1-benzopyran-2-one
7-acetoxy-3-benzyloxy-4-(tetra-O-benzyl-α-D-mannopyranosyloxy)-2H-1-benzopyran-2-one
7-acetoxy-3-hydroxy-4-(α-D-mannopyranosyloxy)-2H-1-benzopyran-2-one
3,7-diacetoxy-4-(tetra-O-acetyl-β-D-galactopyranosyloxy)-2H-1-benzopyran-2-one
3,7-dihydroxy-4-(β-D-galactopyranosyloxy)-2H-1-benzopyran-2-one
7-methoxy-3-acetoxy-4-(tetra-O-acetyl-β-D-galactopyranosyloxy)-2H-1-benzopyran-2-one
7-methoxy-3-hydroxy-4-(β-D-galactopyranosyloxy)-2H-1-benzopyran-2-one
7-ethoxy-3-hydroxy-4-(β-D-galactopyranosyloxy)-2H-1-benzopyran-2-one
7-butoxy-3-hydroxy-4-(β-D-galactopyranosyloxy)-2H-1-benzopyran-2-one
7-octyloxy-3-hydroxy-4-(α-D-galactopyranosyloxy)-2H-1-benzopyran-2-one
7-decanyloxy-3-hydroxy-4-(β-D-galactopyranosyloxy)-2H-1-benzopyran-2-one
7-undecanyloxy-3-hydroxy-4-(β-D-galactopyranosyloxy)-2H-1-benzopyran-2-one
7-isopropoxy-3-hydroxy-4-(β-D-galactopyrsnosyloxy)-2H-1-benzopyran-2-one
7-(3-hexenyloxy)-3-hydroxy-4-(β-D-galactopyranosyloxy)-2H-1-benzopyran-2-one
7-geranyloxy-3-hydroxy-4-(β-D-galactopyranosyloxy)-2H-1-benzopyran-2-one
7-benzoyloxy-3-hydroxy-4-(β-D-galactopyranosyloxy)-2H-1-benzopyran-2-one
7-ethoxy-3-acetoxy-4-(tetra-O-acetyl-β-D-galactopyranosyloxy)-2H-1-benzopyran-2-one
7-ethoxy-3-acetoxy-4-(tetra-O-benzyl-β-D-galactopyranosyloxy)-2H-1-benzopyran-2-one
7-isopropoxy-3-acetoxy-4-(tetra-O-acetyl-β-D-galactopyranosyloxy)-2H-1-benzopyran-2-one
7-butoxy-3-acetoxy-4-(tetra-O-benzoyl-β-D-galactopyranosyloxy)-2H-1-benzopyran-2-one
7-butoxy-3-acetoxy-4-(β-D-galactopyranosyloxy)-2H-1-benzopyran-2-one
7-dodecanyloxy-3-acetoxy-4-(tetra-O-benzyl-β-D-galactopyranosyloxy)-2H-1-benzopyran-2-one
7-dodecanyloxy-3-acetoxy-4-(β-D-galactopyranosyloxy)-2H-1-benzopyran-2-one
7-(3-hexenyloxy)-3-acetoxy-4-(tetra-O-acetyl-β-D-galactopyranosyloxy)-2H-1-benzopyran-2-one
3,7-dipropynyloxy-4-(tetra-O-acetyl-β-D-galactopyranosyloxy)-2H-1-benzopyran-2-one
7-methoxy-3-propynyloxy-4-(tetra-O-acetyl-β-D-galactopyranosyloxy)-2H-1-benzopyran-2-one
7-methoxy-3-benzoyloxy-4-(tetra-O-acetyl-α-D-galactopyranosyloxy)-2H-1-benzopyran-2-one
7-ethoxy-3-propynyloxy-4-(tetra-O-acetyl-β-D-galactopyranosyloxy)-2H-1-benzopyran-2-one
7-isopropoxy-3-propynyloxy-4-(tetra-O-acetyl-β-D-galactopyranosyloxy)-2H-1-benzopyran-2-one
7-(3-hexenyloxy)-3-propynyloxy-4-(tetra-O-acetyl-β-D-galactopyranosyloxy)-2H- 1-benzopyran-2-one
7-geranyloxy-3-propynyloxy-4-(tetra-O-acetyl-β-D-galactopyranosyloxy)-2H-1-benzopyran-2-one
7-octyloxy-3-acetoxy-4-(tetra-O-acetyl-β-D-galactopyranosyloxy)-2H-1-benzopyran-2-one
7-decanyloxy-3-acetoxy-4-(tetra-O-acetyl-β-D-galactopyranosyloxy)-2H-1-benzopyran-2-one
7-decanyloxy-3-acetoxy-4-(tetra-O-benzyl-β-D-galactopyranosyloxy)-2H-1-benzopyran-2-one
7-undecanyloxy-3-acetoxy-4-(tetra-O-acetyl-β-D-galactopyranosyloxy)-2H-1-benzopyran-2-one
7-geranyloxy-3-acetoxy-4-(tetra-O-acetyl-β-D-galactopyranosyloxy)-2H-1-benzopyran-2-one
3,7-dibenzoyloxy-4-(tetra-O-acetyl-β-D-galactopyranosyloxy)-2H-1-benzopyran-2-one
7-methoxy-3-benzoyloxy-4-(tetra-O-acetyl-β-D-galactopyranosyloxy)-2H-1-benzopyran-2-one
7-methoxy-3-benzoyloxy-4-(tetra-O-benzyl-β-D-galactopyranosyloxy)-2H-1-benzopyran-2-one
7-methoxy-3-benzoyloxy-4-(β-D-galactopyranosyloxy)-2H-1-benzopyran-2-one 7-ethoxy-3-benzoyloxy-4-(tetra-O-acetyl-β-D-galactopyranosyloxy)-2H-1-benzopyran-2-one 7-isopropoxy-3-benzoyloxy-4-(tetra-O-acetyl-β-D-galactopyranosyloxy)-2H-1-benzopyran-2-one 7-octyloxy-3-benzoyloxy-4-(tetra-O-acetyl-β-D-galactopyranosyloxy)-2H-1-benzopyran-2-one 7-decanyloxy-3-benzoyloxy-4-(tetra-O-acetyl-β-D-galactopyranosyloxy)-2H-1-benzopyran-2-one 7-undecanyloxy-3-benzoyloxy-4-(tetra-O-acetyl-β-D-galactopyranosyloxy)-2H-1-benzopyran-2-one 7-benzyloxy-3-benzoyloxy-4-(tetra-O-acetyl-β-D-galactopyranosyloxy)-2H-1-benzopyran-2-one 7-benzyloxy-3-hydroxy-4-(β-D-galactopyranosyloxy)-2H-1-benzopyran-2-one 7-acetoxy-3-benzyloxy-4-(tetra-O-benzyl-β-D-galactopyranosyloxy)-2H-1-benzopyran-2-one 7-acetoxy-3-hydroxy-4-(β-D-galactopyranosyloxy)-2H-1-benzopyran-2-one Physiologically acceptable salts of these compounds are also included in the illustrative examples.

The term "physiologically acceptable salts" as used herein means nontoxic alkali addition salts of, for example, the compounds cited above, which include sodium salts, potassium salts, magnesium salts, calcium salts, ammonium salts, nontoxic amine salts and the like. These physiologically acceptable salts can be produced by known methods and are also included in the present invention.

Since the 3-glycosyloxybenzopyran derivatives and physiologically acceptable salts thereof and 4-glycosyloxybenzopyran derivatives and physiologically acceptable salts thereof of the present invention (to be referred to as "the compound of the present invention" hereinafter) have a function to inhibit both immediate and delayed type allergic reactions as will be described later in Examples, they are useful as antiallergic agents for the treatment or prevention of various allergic diseases.

The term "allergic diseases" as used herein means allergic diseases resulting from excess activation of the biological immune mechanism caused by extrinsic or intrinsic antigens, which include immediate type asthma, delayed type asthma, bronchial asthma, pediatric asthma, atopic dermatitis, allergic dermatitis, urticaria, eczema, allergic conjunctivitis, allergic rhinitis, hay fever, food allergy, allergic gastroenteritis, allergic colitis, contact dermatitis, autoimmune disease and the like.

The antiallergic agent which comprises the compound of the present invention as an active ingredient can be administered orally or parenterally (for example, intravenous injection, subcutaneous injection, percutaneous absorption, rectal administration or the like). Such a pharmaceutical agent can be made into various dosage forms according to the purpose, such as tablets, capsules, granules, fine subtilaes, powders, troches, sublingual tablets, suppositories, ointments, injections, emulsions, suspensions, medicated syrups and the like. These dosage forms can be prepared in accordance with known techniques making use of pharmaceutically acceptable carriers which are commonly used in this type of drugs, such as excipients, bonding agents, disintegrators, lubricants, preservatives, anti-oxidative agents, isotonic agents, buffering agents, coating agents, sweetening agents, dissolving agents, bases, dispersing agents, stabilizing agents, coloring agents and the like.

Illustrative examples of these pharmaceutically acceptable carriers are listed in the following.

Firstly, as excipients, the following can be listed: starch and derivatives of starch (such as dextrin, carboxymethyl starch and the like), cellulose and derivatives of cellulose (such as methylcellulose, hydroxypropylmethylcellulose and the like), sugars (such as lactose, sucrose, glucose and the like), silicic acid and silicates (such as naturally occurring aluminum silicate, magnesium silicate and the like), carbonates (such as calcium carbonate, magnesium carbonate, sodium hydrogencarbonate and the like), aluminum magnesium hydroxide, synthetic hydrotalcite, polyoxyethylene derivatives, glycerin monostearate, sorbitan monooleic acid and the like.

As bonding agents, the following can be listed: starch and starch derivatives (such as alpha starches, dextrin and the like), cellulose and derivatives of cellulose (such as ethyl cellulose, sodium carboxymethyl cellulose, hydroxypropylmethyl cellulose and the like), gum arabic, traganth, gelatin, sugars (such as glucose, sucrose and the like), ethanol, polyvinyl alcohols and the like.

As disintegrators, the following can be listed: starch and starch derivatives (such as carboxymethyl starch, hydroxypropyl starch and the like), cellulose and cellulose derivatives (such as sodium carboxymethyl cellulose, crystal cellulose, hydroxypropylmethyl cellulose and the like), carbonates (such as calcium carbonate, calcium hydrogencarbonate and the like), traganth, gelatins, agar and the like.

As lubricants, the following can be listed: stearic acid, calcium stearate, magnesium stearate, talc, silicic acid and its salts (such as light silicic anhydrides, naturally occurring aluminum silicates and the like), titanium oxide, calcium hydrogen phosphate, dry aluminum hydroxide gel, macrogol and the like.

As preservatives, the following can be listed: p-hydroxybenzoates, sulfites (such as sodium sulfites, sodium pyrosulfites and the like), phosphates (such as sodium phosphates, calcium polyphosphates, sodium polyphosphates, sodium methaphosphate and the like), alcohols (such as chlorobutanol, benzyl alcohol and the like), benzalkonium chloride, benzethonium chloride, phenol, cresol, chlorocresol, dihydroacetic acid, sodium dihydroacetate, glycerin sorbic acid, sugars and the like.

As anti-oxidative agents, the following can be listed: sulfites (such as sodium sulfite, sodium hydrogen sulfite and the like), rongalite, erythorbic acid, L-ascorbic acid, cysteine, thioglycerol, butylhydroxyanisol, dibutylhydroxytoluene, propylgallic acid, ascorbyl palmitate, dl-α-tocopherol and the like.

As isotonic agents, the following can be listed: sodium chloride, sodium nitrate, potassium nitrate, dextrin, glycerin, glucose and the like.

As buffering agents, the following can be listed: sodium carbonate, hydrochloric acid, boric acid, phosphates (such as sodium hydrogenphosphate) and the like.

As coating agents, the following can be listed: cellulose derivatives (such as hydroxypropyl cellulose, cellulose acetate phthalate, hydroxypropylmethyl cellulose phthalate and the like), shellac, polyvinylpyrrolidone, polyvinylpyridines (such as poly-2-vinylpyridine, poly-2-vinyl-5-ethylpyridine and the like), polyvinylacetyl diethylaminoacetate, polyvinyl alcohol phthalate, methacrylate, methacrylate copolymers and the like.

As sweetening agents, the following can be listed: sugars (such as glucose, sucrose, lactose and the like), sodium saccharin, sugar alcohols and the like.

As dissolving agents, the following can be listed: ethylenediamine, nicotinamide, sodium saccharin, citric acid, citrates, sodium benzoic acid, soaps, polyvinylpyrrolidone, polysolvates, sorbitan fatty acid esters, glycerin, propylene glycol, benzyl alcohols and the like.

As bases, the following can be listed: fats (such as lard and the like), vegetable oils (such as olive oil, sesame oil and the like), animal oil, lanolin acid, petrolatums, paraffin, wax, resins, bentonite, glycerin, glycol oils, higher alcohols (such as stearyl alcohol, cetanol) and the like.

As dispersing agents, the following can be listed: gum arabic, traganth, cellulose derivatives (such as methyl cellulose and the like), stearic acid polyesters, sorbitan sesquioleate, aluminum monostearate, sodium alginate, polysolvates, sorbitan fatty acid esters and the like.

Lastly, as stabilizing agents, the following can be listed: sulfites (such as sodium hydrogen sulfite and the like), nitrogen, carbon dioxide and the like.

Though the content of the compound of the present invention in these pharmaceutical preparations varies depending on the dosage forms, it may be contained preferably in a concentration of from 0.01 to 100% by weight.

Dose of the antiallergic agent of the present invention can be varied over a broad range depending on each mammal including human, mouse, rat, pig and the like, to be treated, extent of each disease, doctor's judgement and the like. In general, however, it may be administered in a dose of from 0.01 to 200 mg, preferably from 0.01 to 50 mg, more preferably from 0.05 to 10 mg, as the active ingredient per day per kg body weight in the case of oral administration or in a dose of from 0.01 to 10 mg, preferably from 0.01 to 5 mg, as the active ingredient per day per kg body weight in the case of parenteral administration. The daily dose described above may be used in one portion or in divided portions and changed optionally in accordance with the extent of diseases and doctor's judgement.

The following examples are intended to illustrate the preparation of the compounds of this invention and the pharmaceutical compositions of these compounds; however these examples are intended to illustrate the invention and not to be construed to limit the scope of the invention.

REFERENCE EXAMPLE 1

7-methoxy-3-acetoxy-4-benzyloxy-2H-1-benzopyran-2-one (compound 1)

To a mixture of 0.695 g of 7-methoxy-3-acetoxy-4-hydroxy-2H-1-benzopyran-2-one (2.78 mmol) and 0.571 g of benzyl bromide (3.34 mmol) in 5 ml of DMF was added 0.461 g of sodium carbonate (3.34 mmol) under argon atmosphere, then the mixture was stirred at 50° C. for 2 hours. The solid in the reaction mixture was filtered off, the filtrate was poured into 20 ml of water and extracted with 50 ml of benzene. The organic layer was concentrated in vacuo after drying over magnesium sulfate to give oily residue. The residue was purified on silica gel column chromatography (eluent: benzene/ethyl acetate=7/3) to give 0.330 g of the title compound (1). (yield=35%)

$^1$H-NMR (CDCl$_3$, δ-TMS)
7.67 (d, 1H, J=8.8 Hz), 7.40 (m, 5H), 6.82 (d, 1H, J=8.8 Hz), 6.78 (s, 1 H), 5.45 (s, 2H), 3.80 (s, 3H), 2.32 (s, 3H) IR (KBr, cm$^{-1}$): 1760, 1720, 1620, 1435, 1360, 1220 UV: $\lambda_{max}$=310 nm (MeOH)

Elemental analysis for C$_{19}$H$_{16}$O$_6$
Calculated (%): C 67.05; H 4.75; O 28.20
Found (%): C 67.35; H 4.63; O 28.02

REFERENCE EXAMPLE 2

7-methoxy-4-benzyloxy-3-hydroxy-2H-1-benzopyran-2-one (compound 2)

To a mixture of 0.364 g of 7-methoxy-3-acetoxy-4-benzyloxy-2H-1-benzopyran-2-one (1.07 mmol) in 5 ml of methanol was added 0.0578 g of sodium methoxide (1.07 mmol) and the mixture was stirred at room temperature for 1 hour. Then 0.231 g of Amberlyst-15 (Trademark: Organo corp.) was added, and the mixture was stirred at the room temperature for 1 hour. Amberlyst-15 was filtered off, the filtrate was concentrated under reduced pressure. The precipitate was obtained during concentration and filtered to give 0.246 g of the title compound (2). (yield=77 %)

$^1$H-NMR (DMSO-d$_6$, δ-TMS)
9.30 (bs, 1H), 7.67 (d, 1H, J=8.8 Hz), 7.40 (m, 5H), 6.72 (d, 1H, J=8.8 Hz), 6.78 (s, 1H), 5.45 (s, 2H), 3.75 (s, 3H) IR (KBr, cm$^{-1}$): 3200, 1760, 1720, 1620, 1435, 1360, 1220 UV: $\lambda_{max}$=318 nm (MeOH)

Elemental analysis for C$_{17}$H$_{14}$O$_5$
Calculated (%): C 68.45; H 4.73; O 26.82
Found (%): C 68.35; H 4.63; O 26.92

EXAMPLE 1

7-methoxy-4-benzyloxy-3-(tetra-O-acetyl-β-D-glucopyranosyloxy)-2H-1-benzopyran-2-one (compound 3)

1.52 g of 7-methoxy-4-benzyloxy-3-hydroxy-2H-1-benzopyran-2-one (5.12 mmol) and 4.21 g 2, 3, 4, 6-tetra-O-acetyl-α-D-glucopyranosyl bromide (10.23 mmol) were dissolved in 20 ml of acetonitrile at room temperature under argon atmosphere. To this solution, 1.19 g of silver (I) oxide (5.12 mmol) and 3.10 g of molecular sieve 4A (Merck) were added and the mixture was stirred at room temperature for 2 hours. After filtration, the filtrate was concentrated under reduced pressure, giving an oily residue. Purification of the residue on silica gel column chromatography (eluent: benzene/ethyl acetate=10/1) gave 2.15 g of the title compound (3). (yield=78 %)

$^1$H -NMR (CDCl$_3$, δ-TMS)
7.70 (d, 1H, J=8.8 Hz), 7.20~7.40 (m, 5H), 6.88 (d, 1H, J=8.8 Hz), 6.78 (s, 1H), 5.42 (s, 2H), 5.25~5.35 (m, 2H), 5.14 (t, 1H, J=8 Hz), 4.93 (d, 1H, J=8 Hz), 4.21~4.28 (m, 2H), 3.85 (s, 3H), 3.82~3.85 (m, 1H), 2.02~2.22 (m, 12H)IR (KBr, cm$^{-1}$): 1750, 1620, 1435, 1360, 1240 UV: $\lambda_{max}$=310 nm (MeOH)

Elemental analysis for C$_{31}$H$_{32}$O$_{14}$
Calculated (%): C 59.23; H 5.09; O 35.68
Found (%): C 59.40; H 5.15; O 35.45

EXAMPLE 2

7-methoxy-4-hydroxy-3-(tetra-O-acety-β-D-glucopyranosyloxy)-2H-1-benzopyran-2-one (compound 4)

Under hydrogen atmosphere, a mixture of 2.19 g of 7-methoxy-4-benzyloxy-3-(tetra-O-acetyl-β-D-glucopyranosyloxy)-2H-1-benzopyran-2-one (3.48 mmol) and 0.21 g of 10% palladium on activated carbon in 20 ml of ethyl acetate was stirred at room temperature for 2 hours. The catalyst was filtered off, and the filtrate was evaporated to give a crude product. After washing the crude product with diethyl ether, 1.59 g of the title compound (4) was obtained. (yield=85%)

$^1$H-NMR (CDCl$_3$, δ-TMS)
10.50 (bs, 1H), 7.70 (d, 1H, J=8.8 Hz), 6.88 (d, 1H, J=8.8 Hz), 6.78 (s, 1H), 5.25~5.35 (m, 2H), 5.14 (t, 1H, J=8 Hz), 4.93 (d, 1H, J=8 Hz), 4.21~4.28 (m, 2H), 3.85 (s, 3H), 3.82~3.85 (m, 1H), 2.02~2.22 (m, 12H) IR (KBr, cm$^{-1}$): 3250, 1750, 1620, 1435, 1360, 1240 UV: $\lambda_{max}$=310 nm (MeOH)

Elemental analysis for C$_{24}$H$_{26}$O$_{14}$
Calculated (%): C 53.53; H 4.83; O 41.64
Found (%): C 53.40; H 4.60; O 42.00

EXAMPLE 3

7-methoxy-4-hydroxy-3-(β-D-glucopyranosyloxy)-2H-1-benzopyran-2-one (compound 5)

Under argon atmosphere, to a mixture of 0.575 g of 7-methoxy-4-hydroxy-3-(tetra-O-acetyl-β-D-glucopyranosyloxy)-2H-1-benzopyran-2-one (1.07 mmol) in 5 ml of methanol was added 0.348 g of sodium methoxide at 5° C. and followed by stirring at room temperature for 1 hour. Then 2.93 g of Ambrtlyst-15 (Trademark: Organo corp.) was added and the mixture was stirred at room temperature for 1 hour. After dissolving a precipitate generated during neutralization by adding excess methanol, Amberlyst-15 was filtered off and the filtrate was concentrated in vacuo to give a precipitate. Filtration gave 0.305 g of the title compound (5). (yield=77%)

$^1$H -NMR (DMSO-$d_6$, δ-TMS)

11.40 (bs, 1H), 7.67 (d, 1H, J=8.4 Hz), 6.95 (s, 1H), 6.94 (d, 1H, J=8.4 Hz), 4.98 (bs, 4H), 4.83 (d, 1H, J=7.6 Hz), 3.85 (s, 3H), 3.65 (d, 1H, J=7.6 Hz), 3.51 (d, 1H, J=7.6 Hz), 3.41 (m, 1H), 3.31~3.20 (m, 3H) IR (KBr, cm$^{-1}$): 3350, 1660, 1630, 1580, 1270 UV: $\lambda_{max}$=310 nm (McOH)

Elemental analysis for $C_{16}H_{18}O_{10}$

Calculated (%): C 51.89; H 4.90; O 43.21

Found (%): C 51.52; H 4.85; O 43.63

EXAMPLE 4

7-methoxy-4-benzyloxy-3-(tetra-O-acetyl-β-D-mannopyranosyloxy)-2H-1-benzopyran-2-one (compound 6)

In accordance with Example 1, 4.21 g of 2, 3, 4, 6-tetra-O-acetyl-β-D-mannopyranosyl bromide (10.23 mmol) was used instead of 2, 3, 4, 6-tetra-O-acetyl-α-D-glucopyranosyl bromide, 2.30 g of the title compound (6) was obtained. (yield=71%)

$^1$H-NMR (CDCl$_3$, δ-TMS)

7.67 (d, 1H, J=8.4 Hz), 7.20~7.40 (m, 5H), 6.95 (s, 1H), 6.94 (d, 1H, J=8.4 Hz), 6.00 (s, 1H), 5.55 (m, 2H), 5.45 (s, 2H), 5.40 (m, 1H), 4.23 (m, 2H), 4.15 (s, 1H), 3.75 (s, 3H), 2.02~2.22 (m, 12H) IR (KBr, cm$^{-1}$): 1750, 1620, 1435, 1360, 1240 UV: $\lambda_{max}$=310 nm (McOH)

Elemental analysis for $C_{31}H_{32}O_{14}$

Calculated (%): C 59.23; H 5.09; O 35.68

Found (%): C 59.40; H 5.15; O 35.45

EXAMPLE 5

7-methoxy-4-benzyloxy-3-(tetra-O-acetyl-β-D-galactopyranosyloxy)-2H-1-benzopyran-2-one (compound 7)

In accordance with Example 1,4.21 g of 2, 3, 4, 6-tetra-O-acetyl-α-D-galactopyranosyloxy bromide (10.23 mmol) was used instead of 2, 3, 4, 6-tetra-O-acety-α-D-glucopyranosyl bromide, 2.60 g of the title compound (7) was obtained. (yield=80%)

$^1$H-NMR (CDCl$_3$, δ-TMS)

7.72 (d, 1H, J=8.8 Hz), 7.20~7.40 (m, 5H), 6.88 (d, 1H, J=8.8 Hz), 6.78 (s, 1H), 5.55 (m, 2H), 5.45 (s, 2H), 5.40 (s, 1H), 5.16~5.25 (m, 1H), 4.10–4.20 (m, 3H), 3.90 (s, 3H), 2.02~2.22 (m, 12H) IR (KBr, cm$^{-1}$): 1750, 1620, 1435, 1360, 1240 UV: $\lambda_{max}$=310 nm (McOH)

Elemental analysis for $C_{31}H_{32}O_{14}$

Calculated (%): C 59.23; H 5.09; O 35.68

Found (%): C 59.42; H 5.15; O 35.43

EXAMPLE 6

7-methoxy-4-hydroxy-3-(tetra-O-acetyl-α-D-mannopyranosyloxy)-2H-1-benzopyran-2-one (compound 8)

In accordance with Example 2, 7-methoxy-4-benzyloxy-3-(tetra-O-acetyl-α-D-mannopyranosyloxy)-2H-1-benzopyran-2-one was used instead of 7-methoxy-4-benzyloxy-3-(tetra-O-acetyl-β-D-glucopyranosyloxy)-2H-1-benzopyran-2-one, 0.321 g of the title compound (8) was obtained. (yield=81%)

$^1$H-NMR (DMSO-$d_6$, δ-TMS)

11.40 (bs, 1H), 7.67 (d, 1H, J=8.4 Hz), 6.95 (s, 1H), 6.94 (d, 1H, J=8.4 Hz), 6.00 (s, 1H), 5.55 (m, 2H), 5.40 (m, 1H), 4.23 (m, 2H), 4.15 (s, 1H), 3.75 (s, 3H), 2.02~2.22 (m, 12H) IR (KBr, cm$^{-1}$): 3350, 1660, 1630, 1580, 1270 UV: $\lambda_{max}$=310 nm (McOH)

Elemental analysis for $C_{24}H_{26}O_{14}$

Calculated (%): C 53.53; H 4.83; O 41.64

Found (%): C 53.42; H 4.55; O 42.03

EXAMPLE 7

7-methoxy-4-hydroxy-3-(tetra-O-acetyl-β-D-galactopyranosyloxy)-2H-1-benzopyran-2-one (compound 9)

In accordance with Example 2, 7-methoxy-4-benzyloxy-3-(tetra-O-acetyl-β-D-galactopyranosyloxy)-2H-1-benzopyran-2-one was used instead of 7-methoxy-4-benzyloxy-3-(tetra-O-acetyl-β-D-glucopyranosyloxy)-2H-1-benzopyran-2-one, 0.309 g of the title compound (9) was obtained. (yield=78%)

$^1$H -NMR (DMSO-$d_6$, δ-TMS)

11.40 (bs, 1H), 7.67 (d, 1H, J=8.4 Hz), 6.95 (s, 1H), 6.94 (d, 1H, J=8.4 Hz), 4.85 (d, 1H, J=7.6 Hz), 3.85 (s, 3H), 3.65 (d, 1H, J=7.6 Hz), 3.51 (d, 1H, J=7.6 Hz), 3.41 (m, 1H), 3.20–3.40 (m, 3H), 2.05~2.22 (m, 12H) IR (KBr, cm$^{-1}$): 3350, 1660, 1630, 1580, 1270 UV: $\lambda_{max}$=310 nm (McOH)

Elemental analysis for $C_{24}H_{26}O_{14}$

Calculated (%): C 53.53; H 4.83; O 41.64

Found (%): C 53.42; H 4.55; O 42.03

EXAMPLE 8

7-methoxy-4-hydroxy-3-(α-D-mannopyranosyloxy)-2H-1-benzopyran-2-one (compound 10)

In accordance with Example 3, 7-methoxy-4-hydroxy-3-(tetra-O-acetyl-α-D-mannopyranosyloxy)-2H-1-benzopyran-2-one was used instead of 7-methoxy-4-hydroxy-3-(tetra-O-acetyl-β-D-glucopyranosyloxy)-2H-1-benzopyran-2-one, 0.301 g of the title compound was obtained. (yield=78%)

$^1$H-NMR (DMSO-$d_6$, δ-TMS)

11.40 (bs, 1H), 7.67 (d, 1H, J=8.4 Hz), 6.95 (s, 1H), 6.94 (d, 1H, J=8.4 Hz), 6.00 (s, 1H), 5.55 (m, 2H), 5.40 (m, 1H), 4.98 (bs, 4H), 4.23 (m, 2H), 4.15 (s, 1H), 3.75 (s, 3H) IR (KBr, cm$^{-1}$): 3350, 1660, 1630, 1580, 1270 UV: $\lambda_{max}$=310 nm (McOH)

Elemental analysis for $C_{16}H_{18}O_{10}$

Calculated (%): C 51.89; H 4.90; O 43.21

Found (%): C 51.52; H 4.85; O 43.63

EXAMPLE 9

7-methoxy-4-hydroxy-3-(β-D-galactopyranosyloxy)-2H-1-benzopyran-2-one (compound 11)

In accordance with Example 3, 7-methoxy-4-hydroxy-3-(tetra-O-acetyl-β-D-galactopyranosyloxy)-2H-1-benzopyran-2-one was used instead of 7-methoxy-4-hydroxy-3-

(tetra-O-acetyl-β-D-glucopyranosyloxy)-2H-1-benzopyran-2-one, 0.295 g of the title compound (11) was obtained. (yield=74%)

$^1$H -NMR (DMSO-d$_6$, δ-TMS)

11.25 (bs, 1H), 7.67 (d, 1H, J=8.4 Hz), 6.95 (s, 1H), 6.94 (d, 1H, J=8.4 Hz), 5.00 (bs, 4H), 4.85 (d, 1H, J=7.6 Hz), 3.85 (s, 3H). 3.65 (d, 1H, J=7.6 Hz), 3.51 (d, 1H, J=7.6 Hz), 3.41 (m, 1H), 3.20–3.40 (m, 3H) IR (KBr, cm$^{-1}$): 3350, 1660, 1630, 1580, 1270 UV: λ$_{max}$=310 nm (MeOH)

Elemental analysis for C$_{16}$H$_{18}$O$_{10}$

Calculated (%): C 51.89; H 4.90; O 43.21

Found (%): C 51.65; H 4.85; O 43.50

EXAMPLE 10

4-benzyloxy-7-acetoxy-3-(tetra-O-benzyl-β-D-glucopyranosyloxy)-2H-1-benzopyran-2-one (compound 12)

In accordance with Example 1, 1.00 g of 4-benzyloxy-7-acetoxy-3-hydroxy-2H-1-benzopyran-2-one (3.06 mmol) and 2.70 g of 2, 3, 4, 6-tetra-O-benzy-α-D-glucopyranosyl bromide (4.43 mmol) were used instead of 7-methoxy-4-benzyloxy-3-hydroxy-2H-1-benzopyran-2-one and 2, 3, 4, 6-tetra-O-acetyl-α-D-glucopyranosyl bromide, 2.04 g of the title compound (12) was obtained. (yield=78%)

$^1$H-NMR (DMSO-d$_6$, δ-TMS)

7.67 (d, 1H, J=8.8 Hz), 7.15–7.60 (m, 25H), 6.88 (d, 1H, J=8.8 Hz), 6.78 (s, 1H), 5.42 (s, 8H), 5.25–5.35 (m, 2H), 5.20 (m, 2H), 5.14 (t, 1H, J=8 Hz), 4.93 (d, 1H, J=8 Hz), 4.21–4.28 (m, 2H), 3.82–3.85 (m, 1H), 2.38 (s, 3H) IR (KBr, cm$^{-1}$): 1760, 1640, 1600, 1450, 1380

Elemental analysis for C$_{52}$H$_{48}$O$_{11}$

Calculated (%): C 73.58; H 5.66; O 20.76

Found (%) :C 73.53; H 5.78; O 20.69

EXAMPLE 11

7-acetoxy-4-hydroxy-3-(β-D-glucopyranosyloxy)-2H-1-benzopyran-2-one (compound 13)

Under argon atmosphere, 1.50 g of 4-benzyloxy-7-acetoxy-3-(tetra-O-benzyloxy-β-D-glucopyranosyloxy)-2H-1-benzopyran-2-one (1.77 mmo) was dissolved in 150 ml of tetrahydrofuran at room temperature, and 0.15 g of 10% palladium on activated carbon was added. After argon gas was replaced with hydrogen gas, the reaction mixture was stirred at room temperature for 2 hours. The catalyst was filtered off, and the filtrate was evaporated to give a crystalline product. 0.662 g of the title compound (13) was obtained after reprecipitation from tetrahydrofuran and hexane. (yield=94%)

$^1$H -NMR (DMSO-d$_6$, δ-TMS)

10.5 (bs, 1H), 7.70 (d, 1H, J=8.4 Hz), 6.70–6.90 (m, 2H), 5.80 (bs, 1H), 5.32 (d, 1H, J=7.2 Hz), 5.19 (s, 1H), 5.02 (s, 1H), 4.50 (s, 1H), 3.10–3.70 (m, 6H), 2.33 (s, 3H) IR (KBr, cm$^{-1}$): 3400, 1780, 1670, 1610, 1580, 1270

Elemental analysis for C$_{17}$H$_{18}$O$_{11}$

Calculated (%): C 51.26; H 4.52; O 44.22

Found (%): C 51.27; H 4.51; O 44.22

EXAMPLES 12 TO 55

The following Tables show 3-glycopyranosyloxy benzopyran derivatives (14)~(57) obtained by the methods described in Examples.

The abbreviations used in this Table are as follows: Glc, unprotected glucopyranosyl group; Man, unprotected mannopyranosyl group; Gal, unprotected galactopyranosyl group; GlcA, tetraacetylated glucopyranosyl group; ManA, tetraacetylated mannopyranosyl group; Gal, tetraacetylated galactopyranosyl group.

TABLE 1

| Example | Compound | Referential Example | R$_1$ | R$_2$ | R$_3$ | Yield (%) |
| --- | --- | --- | --- | --- | --- | --- |
| 12 | 14 | 3 | H | Glc (β-D form) | H | 78 |
| 13 | 15 | 3 | C$_4$H$_9$ | Glc (β-D form) | H | 75 |
| 14 | 16 | 3 | C$_8$H$_{17}$ | Glc (β-D form) | H | 78 |
| 15 | 17 | 3 | C$_{12}$H$_{25}$ | Glc (β-D form) | H | 81 |
| 16 | 18 | 3 | (CH$_3$)$_2$CH | Glc (β-D form) | H | 70 |
| 17 | 19 | 3 | 3-hexenyl | Glc (β-D form) | H | 72 |
| 18 | 20 | 3 | geranyl | Glc (β-D form) | H | 69 |
| 19 | 21 | 11 | benzoyl | Glc (β-D form) | H | 88 |
| 20 | 22 | 3 | benzyl | Glc (β-D form) | H | 82 |
| 21 | 23 | 8 | H | Man (α-D form) | H | 75 |
| 22 | 24 | 8 | C$_4$H$_9$ | Man (α-D form) | H | 78 |
| 23 | 25 | 8 | C$_8$H$_{17}$ | Man (α-D form) | H | 75 |
| 24 | 26 | 8 | C$_{12}$H$_{25}$ | Man (α-D form) | H | 69 |
| 25 | 27 | 8 | (CH$_3$)$_2$CH | Man (α-D form) | H | 74 |
| 26 | 28 | 8 | 3-hexenyl | Man (α-D form) | H | 81 |
| 27 | 29 | 8 | geranyl | Man (α-D form) | H | 71 |
| 28 | 30 | 11 | benzoyl | Man (α-D form) | H | 85 |
| 29 | 31 | 3 | benzyl | Man (α-D form) | H | 79 |
| 30 | 32 | 9 | H | Gal (β-D form) | H | 80 |
| 31 | 33 | 9 | C$_4$H$_9$ | Gal (β-D form) | H | 74 |
| 32 | 34 | 9 | C$_8$H$_{17}$ | Gal (β-D form) | H | 72 |
| 33 | 35 | 9 | C$_{12}$H$_{25}$ | Gal (β-D form) | H | 81 |
| 34 | 36 | 9 | (CH$_3$)$_2$CH | Gal (β-D form) | H | 72 |
| 35 | 37 | 9 | 3-hexenyl | Gal (β-D form) | H | 69 |
| 36 | 38 | 9 | geranyl | Gal (β-D form) | H | 68 |
| 37 | 39 | 11 | benzoyl | Gal (β-D form) | H | 81 |
| 38 | 40 | 3 | benzyl | Gal (β-D form) | H | 84 |
| 39 | 41 | 9 | C$_6$H$_{13}$ | Gal (β-D form) | H | 70 |
| 40 | 42 | 11 | acetyl | Gal (β-D form) | H | 88 |
| 41 | 43 | 3 | C$_6$H$_{13}$ | Glc (β-D form) | H | 74 |
| 42 | 44 | 8 | C$_6$H$_{13}$ | Man (α-D form) | H | 81 |
| 43 | 45 | 11 | acetyl | Man (α-D form) | H | 86 |
| 44 | 46 | 7 | H | GalA (β-D form) | benzyl | 71 |
| 45 | 47 | 7 | acetyl | GalA (β-D form) | benzyl | 82 |

TABLE 1-continued

| Example | Compound | Referential Example | $R_1$ | $R_2$ | $R_3$ | Yield (%) |
|---|---|---|---|---|---|---|
| 46 | 48 | 7 | 3-hexenyl | GalA (β-D form) | benzyl | 75 |
| 47 | 49 | 7 | benzyl | GalA (β-D form) | benzyl | 76 |
| 48 | 50 | 3 | H | GlcA (β-D form) | benzyl | 80 |
| 49 | 51 | 3 | acetyl | GlcA (β-D form) | benzyl | 78 |
| 50 | 52 | 3 | 3-hexenyl | GlcA (β-D form) | benzyl | 73 |
| 51 | 53 | 3 | benzyl | GlcA (β-D form) | benzyl | 75 |
| 52 | 54 | 6 | H | ManA (α-D form) | benzyl | 78 |
| 53 | 55 | 6 | acetyl | ManA (α-D form) | benzyl | 75 |
| 54 | 56 | 6 | 3-hexenyl | ManA (α-D form) | benzyl | 82 |
| 55 | 57 | 6 | benzyl | ManA (α-D form) | benzyl | 79 |

EXAMPLE 56

3, 7-diacetoxy-4-(tetra-O-acetyl-β-D-glucopyranosyloxy)-2H-1-benzopyran-2-one (compound 58)

0.387 g of 3, 7-diacetoxy-4-hydroxy-2H-1-benzopyran-2-one (1.39 mmol) and 0.858 g of 2, 3, 4, 6-tetra-O-acetyl-α-D-glucopyranosyl bromide (2.09 mmol) were dissolved in 8 ml of acetonitrile at room temperature under argon atmosphere. To the mixture 1.50 g of molecular sieve 4A (Merck) and 0.355 g of silver (I) oxide (1.53 mmol) were added and the reaction mixture was stirred for 2 hours. After filtration of the mixture, the filtrate was concentrated under reduced pressure, giving oily residue. Purification of the residue on silica gel column chromatography (eluent: benzene/ethyl acetate-7/3) gave 0.685 g of the title compound (58). (yield= 81%)

$^1$H-NMR (DMSO-$d_6$, δ-TMS)

7.70 (d, 1H, J=8.8 Hz), 7.20~7.40 (m, 2H), 6.07 (d, 1H, J=7.6 Hz), 5.67 (t, 1H, J=10 Hz), 5.21 (dd, 1H, J=9.6 Hz, J=10 Hz), 5.06 (t, 1H, J=9.6 Hz), 4.20~4.30 (m, 2H), 3.94 (d, 1H, J=10 Hz), 2.40 (s, 3H), 2.32 (s, 3H), 1.90~2.10 (m, 12H) IR (KBr, cm$^{-1}$): 1750, 1640, 1620, 1435, 1360, 1220 Melting point: 127°~129° C.

Elemental analysis for $C_{27}H_{28}O_{16}$

Calculated (%): C 53.29; H 4.61; O 2.10

Found (%): C 53.40; H 4.63; O 1.97

EXAMPLE 57

3, 7-dihydroxy-4-(β-D-glucopyranosyloxy)-2H-1-benzopyran-2-one (compound 59)

To a mixture of 0.635 g of 3, 7-diacetoxy-4-(tetra-O-acetyl-β-D-gluco-pyranosyl-oxy)-2H-1-benzopyran-2-one (1.07 mmol) in 5 ml of methanol was added 0.348 g of sodium methoxide (6.44 mmol) and the reaction mixture was stirred at room temperature for 1 hour. Then 2.93 g of Amberlyst-15 was added, and the mixture was stirred at the room temperature for 1 hour. After dissolving the precipitation generated during neutralization by adding excess methanol, Amberlyst-15 was filtered off and the filtrate was concentrated under reduced pressure to give a crystalline product. The product was reprecipitated from tertahydrofuran and hexane to give 0.293 g of the title compound (59). (yield=77%)

$^1$H-NMR (DMSO-$d_6$, δ-TMS)

10.20 (bs, 1H), 9.30 (bs, 1H), 7.67 (d, 1H, J=8.4 Hz), 6.70~6.90 (m, 2H), 5.38 (d, 1H, J=7.2 Hz), 5.17 (s, 1H), 5.02 (s, 1H), 4.49 (s, 1H), 3.10~3.70 (m, 7H) IR (KBr, cm$^{-1}$): 3350, 1660, 1630, 1580, 1270 Melting point: 203°~204° C.

Elemental analysis for $C_{15}H_{16}O_{10}$

Calculated (%): C 50.56; H 4.53; O 44.91

Found (%): C 50.52; H 4.55; O 44.93

EXAMPLE 58

7-methoxy-3-acetoxy-4-(tetra-O-acetyl-β-D-glucopyranosyloxy)-2H-1-benzopyran-2-one (compound 60)

In accordance with Example 56, 1.00 g of 7-methoxy-3-acetoxy-4-hydroxy-2H-1-benzopyran-2-one (4.20 mmol) was used instead of 3, 7-diacetoxy-4-hydroxy-2H-1-benzopyran-2-one, 1.977 g of the title compound (60) was obtained. (yield=79%)

$^1$H-NMR (DMSO-$d_6$, δ-TMS)

7.60 (d, 1H, J=8.8 Hz), 7.20~7.40 (m, 2H), 6.03 (d, 1H, J=7.6 Hz), 5.61 (t, 1H, J=10 Hz), 5.25 (dd, 1H, J=9.6 Hz, J=10 Hz), 5.02 (t, 1H, J=9.6 Hz), 4.20~4.30 (m, 2H), 3.94 (d, 1H, J=10 Hz), 3.65 (s, 3H), 2.32 (s, 3H), 1.90~2.10 (m, 12H) IR (KBr, cm$^{-1}$): 1730, 1640, 1620, 1440, 1360, 1220

Elemental analysis for $C_{26}H_{28}O_{15}$

Calculated (%): C 53.79; H 4.83; O 1.38

Found (%): C 53.70; H 4.74; O 1.56

EXAMPLE 59

7-methoxy-3-hydroxy-4-(β-D-glucopyranosyloxy)-2H-1-benzopyran-2-one (compound 61)

In accordance with Example 57, 1.50 g of 7-methoxy-3-acetoxy-4-(tetra-O-acetyl-β-D-glucopyranosyloxy)-2H-1-benzopyran-2-one (2.51 mmol) was used instead of 3, 7-diacetoxy-4-(tetra-O-acetyl-β-D-glucopyranosyloxy)-2H-1-benzopyran-2-one, 0.847 g of the title compound (61) was obtained. (yield=91%)

$^1$H-NMR (DMSO-$d_6$, δ-TMS)

9.30 (bs, 1H), 7.76 (d, 1H, J=8.4 Hz), 6.70~6.90 (m, 2H), 5.38 (d, 1H, J=7.2 Hz), 5.17 (s, 1H), 5.01 (s, 1H), 4.49 (s, 1H), 3.10~3.70 (m, 10H) IR (KBr, cm$^{-1}$): 3400, 1680, 1620, 1280

Elemental analysis for $C_{16}H_{18}O_{10}$

Calculated (%): C 51.89; H 4.90; O 43.21

Found (%): C 51.92; H 4.86; O 43.22

EXAMPLE 60

7-butoxy-3-acetoxy-4-(tetra-O-benzoyl-β-D-glucopyranosyloxy)-2H-1-benzopyran-2-one (compound 62)

In accordance with Example 56, 1.20 g of 7-butoxy-3-acetoxy-4-hydroxy-2H-1-benzopyran-2-one (4.11 mmol) and 4.66 g 2, 3, 4, 6-tetra-O-benzyl-α-D-glucopyranosyl bromide (6.17 mmol) were used instead of 3, 7-diacetoxy-4-hydroxy-2H-1-benzopyran-2-one and 2, 3, 4, 6-tetra-O-acetyl-β-D-glucopyranosyl bromide, 2.60 g of the title compound (62) was obtained. (yield=73%)

$^1$H-NMR (DMSO-$d_6$, δ-TMS)

7.70~8.40 (m, 20H), 7.67 (d, 1H, J=8.8 Hz), 7.20~7.40 (m, 2H), 6.07 (d, 1H, J=7.6 Hz), 5.68 (t, 1H, J=10 Hz), 5.20 (dd, 1H, J=9.6 Hz, J=10 Hz) 5.06 (t, 1H, J=9.6 Hz), 4.20~4.30 (m, 2H), 4.10 (t, 2H, J=7.9 Hz), 3.94 (d, 1H, J=10 Hz), 2.32 (s, 3H), 1.20~1.70 (m, 4H), 0.99 (t, 3H, J=7.9 Hz) IR (KBr, cm$^{-1}$): 1750, 1650, 1620, 1435, 1360, 1220

Elemental analysis for $C_{49}H_{42}O_{15}$

Calculated (%): C 67.58; H 4.83; O 27.59

Found (%): C 67.60; H 4.88; O 27.52

EXAMPLE 61

7-butoxy-3-hydroxy-4-(β-D-glucopyranosyloxy)-2H-1-benzopyran-2-one (compound 63)

In accordance with Example 57, 1.50 g of 7-butoxy-3-acetoxy-4-(tetra-O-benzoyl-β-D-glucopyranosyloxy)-2H-1-benzopyran-2-one (1.72 mmol) was used instead of 3,7-diacetoxy-4-(tetra-O-acetyl-β-D-glucopyranosyloxy)-2H-1-benzopyran-2-one, 0.632 g of the title compound (63) was obtained. (yield=89%)

$^1$H-NMR (DMSO-$d_6$, δ-TMS)

9.35 (bs, 1H), 7.72 (d, 1H, J=8.4 Hz), 6.70~6.90 (m, 2H), 5.38 (d, 1H, J=7.6 Hz), 5.17 (s, 1H), 5.00 (s, 1H), 4.44 (s, 1H), 4.11 (t, 2H, J=7.9 Hz), 3.10~3.70 (m, 7H), 1.20–1.70 (m, 4H), 0.95 (t, 3H, J=7.9 Hz) IR (KBr, cm$^{-1}$): 3420, 1660, 1620, 1280

Elemental analysis for $C_{19}H_{24}O_{10}$

Calculated (%): C 55.33; H 5.87; O 38.80

Found (%): C 55.38; H 5.81; O 38.81

EXAMPLE 62

7-methoxy-3-acetoxy-4-(tetra-O-benzyl-β-D-glucopyranosyloxy)-2H-1-benzopyran-2-one (compound 64)

In accordance with Example 56, 0.705 g of 7-methoxy-3-acetoxy-4-hydroxy-2H-1-benzopyran-2-one (2.96 mmol) and 2.70 g of 2, 3, 4, 6-tetra-O-benzyl-α-D-glucopyranosyl bromide (4.43 mmol) were used instead of 3, 7-diacetoxy-4-hydroxy-2H-1-benzopyran-2-one and 2, 3, 4, 6-tetra-O-acetyl-α-D-glucopyranosyl bromide, 1.851 g of the title compound (64) was obtained. (yield=81%)

$^1$H-NMR (DMSO-$d_6$, δ-TMS)

7.67 (d, 1H, J=8.8 Hz), 7.15~7.60 (m, 22H), 6.09 (d, 1H, J=7.6 Hz), 5.70 (t, 1H, J=10 Hz), 5.20 (dd, 1H, J=9.6 Hz, J=10 Hz), 5.06 (t, 1H, J=9.6 Hz, J=10 Hz), 4.80~5.20 (m, 8H), 4.20~4.30 (m, 2H), 3.92 (d, 1H, J=10 Hz), 3.85 (s, 3H), 2.38 (s, 3H) IR (KBr, cm$^{-1}$): 1760, 1640, 1600, 1450, 1380

Elemental analysis for $C_{46}H_{44}O_{11}$

Calculated (%): C 71.50; H 5.70; O 22.80

Found (%): C 71.53; H 5.78; O 22.69

EXAMPLE 63

7-methoxy-3-acetoxy-4-(β-D-glucopyranosyloxy)-2H-1-benzopyran-2-one (compound 65)

Under argon atmosphere, 1.366 g of 7-methoxy-3-acetoxy-4-O-(tetra-O-benzyl-β-D-glucopyranosyloxy)-2H-1-benzopyran-2-one (1.77 mmol) was dissolved in 136 ml of tetrahydrofuran at room temperature, and 0.136 g of 10% palladium on activated carbon was added. After argon gas was replaced with hydrogen gas, the reaction mixture was stirred at room temperature for 2 hours. The catalyst was filtered off, and the filtrate was evaporated to give a crystalline product. 0.686 g of the title compound (65) was obtained after reprecipitation from tetrahydrofuran and hexane. (yield=94%)

$^1$H-NMR (DMSO-$d_6$, δ-TMS)

7.70 (d, 1H, J=8.4 Hz), 6.70~6.90 (m, 2H), 5.32 (d, 1H, J=7.2 Hz), 5.19 (s, 1H), 5.02 (s, 1H), 4.50 (s, 1H), 3.10~3.70 (m, 6H), 3.85 (s, 3H), 2.33 (s, 3H) IR (KBr, cm$^{-1}$): 3400, 1780, 1670, 1610, 1580, 1270

Elemental analysis for $C_{18}H_{20}O_{11}$

Calculated (%): C 52.43; H 4.89; O 2.68

Found (%): C 52.27; H 4.81; O 2.98

EXAMPLES 64 TO 123

The following Tables show 4-glycopyranosyloxy benzopyran derivatives (66)~(125) obtained by the methods described in Example 57 or Example 63.

The abbreviations used in this Table are as follows: Glc, glucopyranosyl group; Man, mannopyranosyl group; Gal, galactopyranosyl group.

TABLE 2

| Example | Compound | Referential Example | $R_{11}$ | $R_{22}$ | $R_{33}$ | Yield (%) |
|---|---|---|---|---|---|---|
| 64 | 66 | 57 | $C_8H_{17}$ | H | Glc (β-D form) | 78 |
| 65 | 67 | 57 | $C_{10}H_{21}$ | H | Glc (β-D form) | 75 |
| 66 | 68 | 57 | $C_{12}H_{25}$ | H | Glc (β-D form) | 81 |
| 67 | 69 | 57 | $(CH_3)_2CH$ | H | Glc (β-D form) | 70 |
| 68 | 70 | 57 | 3-hexenyl | H | Glc (β-D form) | 72 |
| 69 | 71 | 57 | geranyl | H | Glc (β-D form) | 69 |
| 70 | 72 | 57 | benzoyl | H | Glc (β-D form) | 88 |
| 71 | 73 | 63 | $CH_3$ | benzoyl | Glc (β-D form) | 79 |
| 72 | 74 | 63 | $C_4H_9$ | acetyl | Glc (β-D form) | 79 |
| 73 | 75 | 63 | $C_{12}H_{25}$ | acetyl | Glc (β-D form) | 72 |
| 74 | 76 | 57 | benzyl | H | Glc (β-D form) | 75 |
| 75 | 77 | 57 | H | H | Man (α-D form) | 75 |
| 76 | 78 | 57 | $CH_3$ | H | Man (α-D form) | 71 |
| 77 | 79 | 57 | $C_4H_9$ | H | Man (α-D form) | 78 |
| 78 | 80 | 57 | $C_8H_{17}$ | H | Man (α-D form) | 75 |
| 79 | 81 | 57 | $C_{10}H_{21}$ | H | Man (α-D form) | 73 |
| 80 | 82 | 57 | $C_{12}H_{25}$ | H | Man (α-D form) | 69 |
| 81 | 83 | 57 | $(CH_3)_2CH$ | H | Man (α-D form) | 74 |
| 82 | 84 | 57 | 3-hexenyl | H | Man (α-D form) | 81 |
| 83 | 85 | 57 | geranyl | H | Man (α-D form) | 71 |
| 84 | 86 | 57 | benzoyl | H | Man (α-D form) | 85 |
| 85 | 87 | 63 | $CH_3$ | benzoyl | Man (α-D form) | 79 |
| 86 | 88 | 63 | $C_4H_9$ | acetyl | Man (α-D form) | 76 |
| 87 | 89 | 63 | $C_{12}H_{25}$ | acetyl | Man (α-D form) | 70 |
| 88 | 90 | 57 | benzyl | H | Man (α-D form) | 78 |
| 89 | 91 | 57 | H | H | Gal (β-D form) | 80 |
| 90 | 92 | 57 | $CH_3$ | H | Gal (β-D form) | 79 |

TABLE 2-continued

| Example | Compound | Referential Example | $R_{11}$ | $R_{22}$ | $R_{33}$ | Yield (%) |
|---|---|---|---|---|---|---|
| 91 | 93 | 57 | $C_4H_9$ | H | Gal (β-D form) | 74 |
| 92 | 94 | 57 | $C_8H_{17}$ | H | Gal (β-D form) | 72 |
| 93 | 95 | 57 | $C_{10}H_{21}$ | H | Gal (β-D form) | 81 |
| 94 | 96 | 57 | $C_{12}H_{25}$ | H | Gal (β-D form) | 81 |
| 95 | 97 | 57 | $(CH_3)_2CH$ | H | Gal (β-D form) | 72 |
| 96 | 98 | 57 | 3-hexenyl | H | Gal (β-D form) | 69 |
| 97 | 99 | 57 | geranyl | H | Gal (β-D form) | 68 |
| 98 | 100 | 57 | benzoyl | H | Gal (β-D form) | 81 |
| 99 | 101 | 63 | $CH_3$ | benzoyl | Gal (β-D form) | 76 |
| 100 | 102 | 63 | $C_4H_9$ | acetyl | Gal (β-D form) | 71 |
| 101 | 103 | 63 | $C_{12}H_{25}$ | acetyl | Gal (β-D form) | 72 |
| 102 | 104 | 57 | benzyl | H | Gal (β-D form) | 76 |
| 103 | 105 | 57 | acetyl | H | Gal (β-D form) | 32 |
| 104 | 106 | 57 | acetyl | H | Man (α-D form) | 34 |
| 105 | 107 | 63 | H | acetyl | Gal (β-D form) | 68 |
| 106 | 108 | 63 | H | acetyl | Glc (β-D form) | 79 |
| 107 | 109 | 57 | H | acetyl | Man (α-D form) | 78 |
| 108 | 110 | 57 | 3-hexenyl | acetyl | Gal (β-D form) | 33 |
| 109 | 111 | 57 | 3-hexenyl | acetyl | Glc (β-D form) | 37 |
| 110 | 112 | 57 | 3-hexenyl | acetyl | Man (α-D form) | 38 |
| 111 | 113 | 57 | benzyl | acetyl | Gal (β-D form) | 33 |
| 112 | 114 | 57 | benzyl | acetyl | Glc (β-D form) | 36 |
| 113 | 115 | 57 | benzyl | acetyl | Man (α-D form) | 31 |
| 114 | 116 | 57 | acetyl | H | Glc (β-D form) | 38 |
| 115 | 117 | 63 | acetyl | acetyl | Gal (β-D form) | 75 |
| 116 | 118 | 63 | acetyl | acetyl | Glc (β-D form) | 72 |
| 117 | 119 | 63 | acetyl | acetyl | Man (α-D form) | 76 |
| 118 | 120 | 57 | $C_6H_{13}$ | H | Gal (β-D form) | 76 |
| 119 | 121 | 57 | $C_6H_{13}$ | H | Glc (β-D form) | 76 |
| 120 | 122 | 57 | $C_6H_{13}$ | H | Man (α-D form) | 68 |
| 121 | 123 | 63 | $C_6H_{13}$ | acetyl | Gal (β-D form) | 32 |
| 122 | 124 | 63 | $C_6H_{13}$ | acetyl | Glc (β-D form) | 36 |
| 123 | 125 | 63 | $C_6H_{13}$ | acetyl | Man (α-D form) | 31 |

Compound 14

$^1$H-NMR (DMSO-$d_6$, δ-TMS): 10.55 (s, 1H), 9.30 (bs, 1H), 7.75 (d, 1H, J=8.6 Hz), 6.80~7.00 (m, 2H), 5.80 (bs, 1H), 5.38 (d, 1H, J=7.2 Hz), 5.17 (d, 1H, J=4.4 Hz), 5.01 (d, 1H, J=4.4 Hz), 4.46 (s, 1H), 3.10~3.70 (m, 6H) IR (KBr, cm$^{-1}$): 3400, 2900, 1680, 1620, 1320

Elemental analysis:

Calculated (%): C 50.56, H 4.53, O 44.91

Found (%): C 50.69, H 4.68, O 44.63

Compound 15

$^1$H-NMR (DMSO-$d_6$, δ-TMS): 9.30 (bs, 1H), 7.75 (d, 1H, J=8.6 Hz), 6.80~7.00 (m, 2H), 5.80 (bs, 1H), 5.38 (d, 1H, J=7.2 Hz), 5.17 (d, 1H, J=4.4 Hz), 5.01 (d, 1H, J=4.4 Hz), 4.46 (s, 1H), 4.02 (t, 2H, J=6.4 Hz ), 3.10~3.70 (m, 6H), 1.20–1.80 (m, 4H), 0.87 (t, 3H, J=6.4 Hz) IR (KBr, cm$^{-1}$): 3400, 2900, 1680, 1620, 1320

Elemental analysis:

Calculated (%): C 55.33, H 5.87, O 38.80

Found (%): C 55.65, H 5.85, O 38.50

Compound 16

$^1$H-NMR (DMSO-$d_6$, δ-TMS): 9.30 (bs, 1H), 7.75 (d, 1H, J=8.6 Hz), 6.80~7.00 (m, 2H), 5.80 (bs, 1H), 5.38 (d, 1H, J=7.2 Hz), 5.17 (d, 1H, J=4.4 Hz), 5.01 (d, 1H, J=4.4 Hz), 4.46 (s, 1H), 4.02 (t, 2H, J=6.4 Hz), 3.10–3.70 (m, 6H), 1.20~1.80 (m, 12H), 0.87 (t, 3H, J=6.4 Hz) IR (KBr, cm$^{-1}$): 3400, 2900, 1680, 1620, 1320 Melting point: 167°~169° C.

Elemental analysis:

Calculated (%): C 58.96, H 6.89, O 34.15

Found (%): C 58.99, H 6.85, O 34.16

Compound 17

$^1$H-NMR (DMSO-$d_6$, δ-TMS): 9.30 (bs, 1H), 7.74 (d, 1H, J=9.6 Hz), 6.80~7.00 (m, 2H), 5.82 (bs, 1H), 5.39 (d, 1H, J=7.2 Hz), 5.16 (d, 1H, J=4.4 Hz), 5.01 (d, 1H, J=4.4 Hz), 4.46 (s, 1H), 4.02 (t, 2H, J=6.4 Hz), 3.10–3.70 (m, 6H), 1.20~1.80 (m, 20H), 0.85 (t, 3H, J=6.4 Hz) IR (KBr, cm$^{-1}$): 3400, 2900, 2850, 1670, 1630, 1260 Melting point: 171°~172° C.

Elemental analysis:

Calculated (%): C 61.81, H 7.69, O 30.50

Found (%): C 61.92, H 7.52, O 30.56

Compound 18

$^1$H-NMR (DMSO-$d_6$, δ-TMS): 9.35 (bs, 1H), 7.71 (d, 1H, J=9.6 Hz), 6.80~7.00 (m, 2H), 5.80 (bs, 1H), 5.40 (d, 1H, J=7.2 Hz), 5.15 (d, 1H, J=4.4 Hz), 5.01 (d, 1H, J=4.4 Hz), 4.46 (s, 1H), 3.90 (m, 1H), 3.10~3.70 (m, 6H), 1.10 (d, 6H, J=6.0 Hz) IR (KBr, cm$^{-1}$): 3400, 2900, 2800, 1680, 1630, 1260

Elemental analysis:

Calculated (%): C 54.27, H 5.57, O 40.16

Found (%): C 54.28, H 5.54, O 40.18

Compound 19

$^1$H-NMR (DMSO-$d_6$, δ-TMS): 9.32 (bs, 1H), 7.71 (d, 1H, J=8.6 Hz), 6.80~7.00 (m, 2H), 5.90 (bs, 1H), 5.40~5.60 (m, 2H), 5.38 (d, 1H, J=7.2 Hz), 5.17 (d, 1H, J=4.4 Hz), 5.01 (d, 1H, J=4.4 Hz), 4.46 (s, 1H), 4.02 (t, 2H, J=6.8 Hz), 3.10~3.70 (m, 6H), 1.50~2.40 (m, 4H), 0.87 (t, 3H, J=6.8 Hz) IR (KBr, cm$^{-1}$): 3400, 2900, 1680, 1620, 1320

Elemental analysis:

Calculated (%): C 57.53, H 5.98, O 36.49

Found (%): C 57.59, H 5.97, O 36.44

Compound 20

¹H-NMR (DMSO-d₆, δ-TMS): 9.30 (bs, 1H), 7.72 (d, 1H, J=8.0 Hz), 6.80~7.00 (m, 2H), 5.90 (bs, 1H), 5.40~5.60 (m, 2H), 5.38 (d, 1H, J=7.2 Hz), 5.17 (d, 1H, J=4.4 Hz), 5.01 (d, 1H, J=4.4 Hz), 4.46 (s, 1H), 4.10 (d, 2H, J=7.0 Hz), 3.10~3.70 (m, 6H), 1.70~2.40 (m, 4H), 1.50~1.80 (m, 9H) IR (KBr, cm⁻¹): 3400, 2900, 2800, 1670, 1620, 1220

Elemental analysis:

Calculated (%): C 60.96, H 6.55, O 32.49

Found (%): C 60.99, H 6.57, O 32.44

Compound 21

¹H-NMR (DMSO-d₆, δ-TMS): 9.35 (bs, 1H), 7.70~8.10 (m, 2H), 7.40~7.65 (m, 4H), 6.80~7.00 (m, 2H), 5.80 (bs, 1H), 5.38 (d, 1H, J=7.2 Hz), 5.15 (d, 1H J=4.4 Hz), 5.01 (d, 1H, J=4.4 Hz), 4.46 (s, 1H), 3.10~3.70 (m, 6H) IR (KBr, cm⁻¹): 3400, 2900, 1700, 1680, 1620, 1320

Elemental analysis:

Calculated (%): C 57.39, H 4.35, O 38.26

Found (%): C 57.34, H 4.37, O 38.29

Compound 22

¹H -NMR (DMSO-d₆, δ-TMS): 9.35 (bs, 1H), 7.40~7.65 (m, 6H), 6.80~7.00 (m, 2H), 5.80 (bs, 1H), 5.55 (s, 2H), 5.38 (d, 1H, J=7.2 Hz), 5.15 (d, 1H, J=4.4 Hz), 5.01 (d, 1H, J=4.4 Hz), 4.46 (s, 1H), 3.10–3.70 (m, 6H) IR (KBr, cm⁻¹): 3400, 2900, 1680, 1620, 1320

Elemental analysis value (%):

Calculated (%): C 59.19, H 4.97, O 35.84

Found (%): C 59.18, H 4.85, O 35.97

Compound 23

¹H -NMR (DMSO-d₆, δ-TMS): 10.18 (bs, 1H), 9.45 (bs, 1H), 7.60 (d, 1H, J=8.8 Hz), 6.80~7.00 (m, 2H), 6.16 (s, 1H), 5.18 (bs, 1H ), 4.97 (s, 1H), 4.75 (s, 1H), 4.39 (s, 1H), 3.10–3.90 (m, 6H) IR (KBr, cm⁻¹): 3350, 1640, 1610, 1520, 1260

Elemental analysis:

Calculated (%): C 50.56, H 4.53, O 44.91

Found (%): C 50.51, H 4.55, O 44.94

Compound 24

¹H -NMR (DMSO-d₆, δ-TMS): 9.39 (bs, 1H), 7.62 (d, 1H, J=8.8 Hz), 6.80~7.00 (m, 2H), 6.14 (s, 1H), 5.17 (s, 1H), 5.00 (s, 1H), 4.74 (s, 1H), 4.34 (s, 1 H), 4.25 (t, 2H, J=8.0 Hz.), 4.11 (m, 2H), 3.10–3.70 (m, 4H), 1.20–1.70 (m, 4H), 0.95 (t, 3H, J=8.0 Hz) IR (KBr, cm⁻¹): 3320, 2900, 1700, 1640, 1 610, 1220

Elemental analysis:

Calculated (%): C 55.33, H 5.87, O 38.80

Found (%): C 55.37, H 5.82, O 38.81

Compound 25

¹H -NMR (DMSO-d₆, δ-TMS): 9.39 (bs, 1H), 7.62 (d, 1H, J=8.8 Hz), 6.80~7.00 (m, 2H), 6.14 (s, 1H), 5.17 (s, 1H), 5.00 (s, 1H), 4.74 (s, 1H), 4.34 (s, 1H), 4.25 (t, 2H, J=8.0 Hz), 4.11 (m, 2H), 3.10–3.70 (m, 4H), 1.20–1.75 (m, 12H), 0.95 (t, 3H, J=8.0 Hz) IR (KBr, cm⁻¹): 3320, 2900, 1700, 1640, 1610, 1220

Elemental analysis:

Calculated (%): C 58.96, H 6.89, O 34.15

Found (%): C 58.97, H 6.82, O 34.21

Compound 26

¹H -NMR (DMSO-d₆, δ-TMS): 9.38 (bs, 1H), 7.60 (d, 1H, J=9.2 Hz), 6.80–7.00 (m, 2H), 6.16 (s, 1H), 5.10 (s, 1H), 4.96 (s, 1H), 4.71 (s, 1H), 4.36 (s,1H), 4.02 (t, 2H, J=7.2 Hz), 3.10–3.70 (m, 6H), 1.20–1.80 (m, 20H), 0.85 (t, H, J=7.2 Hz) IR (KBr, cm⁻¹): 3350, 2900, 2850, 1700, 1640, 1610, 1260

Elemental analysis:

Calculated (%): C 61.81, H 7.69, O 30.50

Found (%): C 61.79, H 7.70, O 30.51

Compound 27

¹H -NMR (DMSO-d₆, δ-TMS): 9.35 (bs, 1H), 7.61 (d, 1H, J=8.2 Hz), 6.80~7.00 (m, 2H), 6.16 (s, 1H), 5.15 (s, 1H), 4.95 (s, 1H), 4.71 (s, 1H), 4.37 (s, 1 H), 4.15 (m, 1H), 3.10–3.70 (m, 6H), 1.10 (d, 6H, J=6.0 Hz) IR (KBr, cm⁻¹): 3400, 2900, 2850, 1690, 1630, 1600, 1260

Elemental analysis:

Calculated (%): C 54.27, H 5.57, O 40.16

Found (%): C 54.23, H 5.58, O 40.19

Compound 28

¹H-NMR (DMSO-d₆, δ-TMS): 9.32 (bs, 1H), 7.61 (d, 1H, J=8.2 Hz), 6.80–7.00 (m, 2H), 6.16 (s, 1H), 5.40–5.60 (m, 2H), 5.18 (s, 1H), 4.97 (s, 1H), 4.71 (s 1H,), 4.36 (s, 1H), 4.00 (t, 2H, J=6.8 Hz), 3.10–3.70 (m, 6H), 1.50–2.40 (m, 4H), 0.87 (t, 3H, J=6.8 Hz) IR (KBr, cm⁻¹): 3400, 2950, 1690, 1630, 1610, 1220

Elemental analysis:

Calculated (%): C 57.53, H 5.98, O 36.49

Found (%): C 57.58, H 5.97, O 36.45

Compound 29

¹H-NMR (DMSO-d₆, δ-TMS): 9.39 (bs, 1H), 7.62 (d, 1H, J=8.2 Hz), 6.80–7.00 (m, 2H), 6.15 (s, 1H), 5.40–5.60 (m, 2H), 5.18 (s, 1H), 4.99 (s, 1H), 4.71 (s 1H), 4.40 (s, 1H), 4.11 (d, 2H, J=7.0 Hz), 3.10–3.70 (m, 6H), 1.70–2.40 (m, 4H), 1.50–1.80 (m, 9H) IR (KBr, cm⁻¹): 3400, 2900, 2850, 1690, 1630, 1600, 1220

Elemental analysis:

Calculated (%): C 60.96, H 6.55, O 32.49

Found (%): C 61.02, H 6.52, O 32.46

Compound 30

¹H-NMR (DMSO-d₆, δ-TMS): 9.40 (bs, 1H), 7.40–8.10 (m, 6H), 6.80–7.00 (m, 2H), 6.15 (s, 1H), 5.15 (s, 1H), 4.95 (s, 1H), 4.69 (s, 1H), 4.46 (s, 1H), 3.10–3.70 (m, 6H) IR (KBr, cm⁻¹): 3400, 2900, 1700, 1680, 1620, 1320

Elemental analysis:

Calculated (%): C 57.39, H 4.35, O 38.26

Found (%): C 57.38, H 4.42, O 38.20

Compound 31

¹H-NMR (DMSO-d₆, δ-TMS): 9.40 (bs, 1H), 7.40–7.70 (m, 6H), 6.80–7.00 (m, 2H), 6.15 (s, 1H), 5.50 (s, 2H), 5.15 (s, 1H), 4.95 (s, 1H), 4.69 (s, 1 H), 4.46 (s, 1H), 3.10–3.70 (m, 6H) IR (KBr, cm⁻¹): 3400, 2900, 1680, 1620, 1320

Elemental analysis:

Calculated (%): C 59.19, H 4.97, O 35.84

Found (%): C 59.15, H 4.83, O 36.02

Compound 32

¹H -NMR (DMSO-d₆, δ-TMS): 10.18 (bs, 1H), 9.35 (bs, 1H), 7.76 (d, 1H, J=8.8 Hz), 6.80–7.00 (m, 2H), 5.80 (s, 1H), 5.26 (d, 1H, J=8.0 Hz), 4.50–4.70 (m, 3H), 3.20–3.90 (m, 6H) IR (KBr, cm⁻¹): 3450, 3300, 1630, 1610, 1520, 1260

Elemental analysis:

Calculated (%): C 50.56, H 4.53, O 44.91

Found (%): C 50.60, H 4.50, O 44.90

Compound 33

¹H -NMR (DMSO-d₆, δ-TMS): 9.41 (bs, 1H), 7.76 (d, 1H, J=9.6 Hz), 6.80–7.00 (m, 2H), 5.77 (s, 1H), 5.27 (d, 1H, J=8.0 Hz), 4.50–4.70 (m, 3H), 4.11 (t, 2H, J=7.9 Hz), 3.20–3.80 (m, 6H), 1.20–1.70 (m, 4H), 0.95 (t, 3H, J=7.9 Hz) IR (KBr, cm⁻¹): 3400, 3300, 2900, 1670, 1620, 1610, 1220

Elemental analysis:

Calculated (%): C 55.33, H 5.87, O 38.80

Found (%): C 55.33, H 5.83, O 38.84

Compound 34

$^1$H -NMR (DMSO-d$_6$, δ-TMS): 9.41 (bs, 1H), 7.76 (d, 1H, J=9.6 Hz), 6.80–7.00 (m, 2H), 5.85 (s, 1H), 5.26 (d, 1H, J=8.0 Hz), 4.50–4.70 (m, 3H), 4.02 (t, 2H, J=7.2 Hz), 3.20–3.80 (m, 6H), 1.20–1.80 (m, 12H), 0.87 (t, 3H, J=7.2 Hz) IR (KBr, cm$^{-1}$): 3450, 3300, 2900, 2850, 1680, 1620, 1610, 1260 Melting point: 160°–162° C.

Elemental analysis:

Calculated (%): C 58.96, H 6.89, O 34.15

Found (%): C 59.02, H 6.85, O 34.13

Compound 35

$^1$H -NMR (DMSO-d$_6$, δ-TMS): 9.38 (bs, 1H), 7.77 (d, 1H, J=8.6 Hz), 6.80–7.00 (m, 2H), 5.83 (s, 1H), 5.26 (d, 1H, J=8.0 Hz), 4.50–4.70 (m, 3H), 4.02 (t, 2H, J=7.2 Hz), 3.20–3.80 (m, 6H), 1.20–1.80 (m, 20H), 0.85 (t, 3H, J=7.2 Hz) IR (KBr, cm$^{-1}$): 3450, 3300, 2900, 2850, 1680, 1630, 1610, 1260

Elemental analysis:

Calculated (%): C 61.81, H 7.69, O 30.50

Found (%): C 61.77, H 7.69, O 30.54

Compound 36

$^1$H -NMR (DMSO-d$_6$, δ-TMS): 9.38 (bs, 1H), 7.75 (d, 1H, J=8.6 Hz), 6.80–7.00 (m, 2H), 5.85 (s, 1H), 5.25 (d, 1H, J=8.0 Hz), 4.50–4.80 (m, 3H), 4.05 (m, 1H), 3.20–3.80 (m, 6H), 1.10 (d, 6H, J=6.0 Hz) IR (KBr, cm$^{-1}$): 3400, 3350, 2900, 2850, 1690, 1630, 1600, 1260

Elemental analysis:

Calculated (%): C 54.27, H 5.57, O 40.16

Found (%): C 54.25, H 5.55, O 40.20

Compound 37

$^1$H -NMR (DMSO-d$_6$, δ-TMS): 9.42 (bs, 1H), 7.76 (d, 1H, J=8.6 Hz), 6.80–7.00 (m, 2H), 5.86 (s, 1H), 5.40–5.60 (m, 2H), 5.24 (d, 1H, J=8.0 Hz), 4.50–4.80 (m, 3H), 4.02 (t, 2H, J=6.8 Hz), 3.20–3.80 (m, 6H), 1.50–2.40 (m, 4H), 0.87 (t, 3H, J=6.8 Hz) IR (KBr, cm$^{-1}$): 3450, 3300, 2950, 1690, 1630, 1610, 1220

Elemental analysis:

Calculated (%): C 57.53, H 5.98, O 36.49

Found (%): C 57.49, H 6.01, O 36.50

Compound 38

$^1$H -NMR (DMSO-d$_6$, δ-TMS): 9.39 (bs, 1H), 7.77 (d, 1H, J=8.6 Hz), 6.80–7.00 (m, 2H), 5.84 (s, 1H), 5.40–5.60 (m, 2H), 5.25 (d, 1H, J=8.0 Hz), 4.50–4.80 (m, 3H), 4.10 (d, 2H, J=7.0 Hz), 3.20–3.80 (m, 6H), 1.70–2.40 (m, 4H), 1.40–1.60 (m, 9H) IR (KBr, cm$^{-1}$): 3400, 3350, 2900, 2850, 1680, 1630, 1610, 1220

Elemental analysis:

Calculated (%): C 60.96, H 6.55, O 32.49

Found (%): C 60.93, H 6.61, O 32.46

Compound 39

$^1$H -NMR (DMSO-d$_6$, δ-TMS): 9.40 (bs, 1H), 7.40–8.10 (m, 6H), 6.80–7.00 (m, 2H), 5.85 (s, 1H), 5.24 (d, 1H, J=8.0 Hz), 4.50–4.80 (m, 3H), 3.20–3.80 (m, 6H) IR (KBr, cm$^{-1}$): 3450, 2900, 1700, 1680, 1620, 1320

Elemental analysis:

Calculated (%): C 57.39, H 4.35, O 38.26

Found (%): C 57.41, H 4.33, O 38.26

Compound 40

$^1$H-NMR (DMSO-d$_6$, δ-TMS): 9.40 (bs, 1H), 7.40–7.85 (m, 6H), 6.80–7.00 (m, 2H), 5.85 (s, 1H), 5.42 (s, 2H), 5.24 (d, 1H, J=8.0 Hz), 4.50–4.80 (m, 3H) 3.20–3.80 (m, 6H) IR (KBr, cm$^{-1}$): 3450, 2900, 1680, 1620, 1320

Elemental analysis:

Calculated (%): C 59.19, H 4.97, O 35.84

Found (%): C 59.20, H 4.84, O 35.96

Compound 41

$^1$H -NMR (DMSO-d$_6$, δ-TMS): 9.39 (bs, 1H), 7.74 (d, 1H, J=9.6 Hz), 6.80–7.00 (m, 2H), 5.83 (s, 1H), 5.24 (d, 1H, J=8.0 Hz), 4.40–4.60 (m, 3H), 4.00 (t, 2H, J=7.2 Hz), 3.20–3.70 (m, 6H), 1.20–1.70 (m, 8H), 0.89 (t, 3H, J=7.2 Hz) IR (KBr, cm$^{-1}$): 3450, 3300, 2900, 2800, 1670, 1620, 1600, 1260

Elemental analysis:

Calculated (%): C 57.26, H 6.41, O 36.33

Found (%): C 57.30, H 6.38, O 36.32

Compound 42

$^1$H-NMR (DMSO-d$_6$, δ-TMS): 10.15 (bs, 1H), 7.74 (d, 1H, J=8.8 Hz), 6.90–7.00 (m, 2H), 5.85 (s, 1H), 5.23 (d, 1H, J=8.0 Hz), 4.50–4.80 (m, 3H), 3.20–3.80 (m, 6H), 2.35 (s, 3H) IR (KBr, cm$^{-1}$): 3450, 3300, 1750, 1640, 1600, 1510, 1260

Elemental analysis:

Calculated (%): C 51.26, H 4.55, O 44.19

Found (%): C 51.30, H 4.53, O 44.17

Compound 43

$^1$H-NMR (DMSO-d$_6$, δ-TMS): 9.31 (bs, 1H), 7.77 (d, 1H, J=8.6 Hz), 6.80–7.00 (m, 2H), 5.83 (bs, 1H), 5.35 (d, 1H, J=7.2 Hz), 5.16 (d, 1H, J=4.4 Hz), 5.00 (d, 1H, J=4.4 Hz), 4.46 (s, 1H), 4.01 (t, 2H, J=6.4 Hz ), 3.10–3.70 (m, 6H), 1.20–1.70 (m, 8H), 0.86 (t, 3H, J=6.4 Hz) IR (KBr, cm$^{-1}$): 3400, 2900, 1670, 1610, 1320

Elemental analysis:

Calculated (%): C 57.26, H 6.41, O 36.33

Found (%): C 57.23, H 6.39, O 36.38

Compound 44

$^1$H -NMR (DMSO-d$_6$, δ-TMS): 9.40 (bs, 1H), 7.63 (d, 1H, J=8.8 Hz), 6.80–7.00 (m, 2H), 6.12 (s, 1H), 5.20 (s, 1H), 5.01 (s, 1H), 4.72 (s, 1H), 4.34 (s, 1H), 4.27 (t, 2H, J=8.0 Hz), 4.09 (m, 2H), 3.10–3.70 (m, 4H), 1.20–1.65 (m, 8H), 0.93 (t, 3H, J=8.0 Hz) IR (KBr, cm$^{-1}$): 3320, 2900, 1710, 1640, 1600, 1220

Elemental analysis:

Calculated (%): C 57.26, H 6.41, O 36.33

Found (%): C 57.25, H 6.45, O 36.30

Compound 45

$^1$H -NMR (DMSO-d$_6$, δ-TMS): 10.17 (bs, 1H), 7.62 (d, 1H, J=8.8 Hz), 6.80–7.00 (m, 2H), 6.14 (s, 1H), 5.18 (bs, 1H, ), 4.99 (s, 1H), 4.77 (s, 1H), 4.40 (s, 1H), 3.10–3.90 (m, 6H), 2.40 (s, 3H) IR (KBr, cm$^{-1}$): 3350, 1740, 1650, 1610, 1520, 1250

Elemental analysis:

Calculated (%): C 51.26, H 4.55, O 44.19

Found (%): C 51.28, H 4.56, O 44.16

Compound 46

$^1$H -NMR (CDCl$_3$, δ-TMS): 10.21 (bs, 1H), 7.73 (d, 1H, J=8.8 Hz), 7.10–7.30 (m, 5H), 6.90 (d, 1H, J=8.8 Hz), 6.77 (s, 1H), 5.56 (m, 2H), 5.46 (s, 2H), 5.40 (s, 1H), 5.16–5.26 (m, 1H), 4.10–4.20 (m, 3H), 2.02–2.22 (m, 12H) IR (KBr, cm$^{-1}$): 3450, 1750, 1620, 1440, 1360, 1230

Elemental analysis:

Calculated (%): C 58.63; H 4.92; O 36.45

Found (%): C 58.62; H 4.91; O 36.47

Compound 47

$^1$H -NMR (CDCl$_3$, δ-TMS): 7.71 (d, 1H, J=8.8 Hz), 7.10–7.30 (m, 5H), 6.87 (d, 1H, J=8.8 Hz), 6.79 (s, 1H), 5.53 (m, 2H), 5.43 (s, 2H), 5.39 (s, 1H), 5.16–5.23 (m, 1H), 4.10–4.20 (m, 3H), 2.41 (s, 3H), 2.00–2.2(m, 12H) IR (KBr, cm$^{-1}$): 1750, 1610, 1440, 1370, 1230

Elemental analysis:

Calculated (%): C 58.54; H 4.91; O 36.55

Found (%): C 58.52; H 4.89; O 36.59

Compound 48

$^1$H -NMR (CDCl$_3$, δ-TMS): 7.71 (d, 1H, J=8.8 Hz), 7.20–7.30 (m, 5H), 6.87 (d, 1H, J=8.8 Hz), 6.77 (s, 1H), 5.40–5.60 (m, 7H), 5.14–5.23 (m, 1H), 4.11–4.21 (m, 3H), 4.01 (t, 2H, J=6.8 Hz), 2.01–2.20 (m, 12H), 1.51–2.41 (m, 4H), 0.88 (t, 3H, J=6.8 Hz) IR (KBr, cm$^{-1}$): 2900, 1750, 1620, 1440, 1370, 1240

Elemental analysis:

Calculated (%): C 62.06; H 5.79; O 32.15

Found (%): C 62.03; H 5.82; O 32.15

Compound 49

$^1$H -NMR (CDCl$_3$, δ-TMS): 7.73 (d, 1H, J=8.8 Hz), 7.21–8.10 (m, 10H), 6.89 (d, 1H, J=8.8 Hz), 6.77 (s, 1H), 5.54 (m, 2H), 5.46 (m, 4H), 5.41 (s, 1H), 5.15–5.26 (m, 1H), 4.11–4.21 (m, 3H), 2.01–2.20 (m, 12H) IR (KBr, cm$^{-1}$): 1740, 1620, 1445, 1360, 1240

Elemental analysis:

Calculated (%): C 63.07; H 5.15; O 31.78

Found (%): C 63.09; H 5.10 ; O 31.81

Compound 50

$^1$H-NMR (CDCl$_3$, δ-TMS): 10.22 (bs, 1H), 7.71 (d, 1H, J=8.8 Hz), 7.21–7.41 (m, 5H), 6.88 (d, 1H, J=8.8 Hz), 6.80 (s, 1H), 5.40 (s, 2H), 5.25–5.35 (m, 2H), 5.13 (t, 1H, J=8 Hz), 4.90 (d, 1H, J=8 Hz), 4.20–4.30 (m, 2H), 3.82–3.85 (m, 1H), 2.00–2.22 (m, 12H) IR (KBr, cm$^{-1}$): 3440, 1750, 1620, 1440, 1360, 1230

Elemental analysis:

Calculated (%): C 58.63; H 4.92; O 36.45

Found (%): C 58.64; H 4.93; O 36.43

Compound 51

$^1$H -NMR (CDCl$_3$, δ-TMS): 7.72 (d, 1H, J=8.8 Hz), 7.21–7.41 (m, 5H), 6.86 (d, 1H, J=8.8 Hz), 6.78 (s, 1H), 5.40 (s, 2H), 5.25–5.35 (m, 2H), 5.12 (t, 1 H, J=8 Hz), 4.95 (d, 1H, J=8 Hz), 4.21–4.30 (m, 2H), 3.80–3.85 (m, 1H), 2.41 (s, 3H), 2.02–2.25 (m, 12H) IR (KBr, cm$^{-1}$): 1750, 1620, 1435, 1350, 1230

Elemental analysis:

Calculated (%): C 58.54; H 4.91; O 36.55

Found (%): C 58.55; H 4.88; O 36.57

Compound 52

$^1$H-NMR (CDCl$_3$, δ-TMS): 7.68 (d, 1H, J=8.8 Hz), 7.20–7.40 (m, 5H), 6.88 (d, 1H, J=8.8 Hz), 6.75 (s, 1H), 5.45 (s, 2H), 5.42–5.62 (m, 2H), 5.26–5.36 (m, 2H), 5.15 (t, 1H, J=8 Hz), 4.91 (d, 1H, J=8 Hz), 4.21–4.28 (m, 2H), 4.01 (t, 2H, J=6.8 Hz), 3.82–3.86 (m, 1H), 2.04–2.24 (m, 12H), 1.52–2.40 (m, 4H), 0.89 (t, 3H, J=6.8 Hz) IR (KBr, cm$^{-1}$): 2910, 1750, 1630, 1430, 1360, 1240

Elemental analysis:

Calculated (%): C 62.06; H 5.79; O 32.15

Found (%): C 62.05; H 5.82; O 32.13

Compound 53

$^1$H -NMR (CDCl$_3$, δ-TMS): 7.70 (d, 1H, J=8.8 Hz), 7.20–8.13 (m, 10H), 6.85 (d, 1H, J=8.8 Hz), 6.76 (s, 1H), 5.45 (m, 2H), 5.25–5.30 (m, 4H), 5.15 (t, 1H, J=8 Hz), 4.91 (d, 1H, J=8 Hz), 4.21–4.28 (m, 2H), 3.81–3.86 (m, 1H) 2.02–2.22 (m, 12H) IR (KBr, cm$^{-1}$): 1750, 1630, 1440, 1350, 1240

Elemental analysis:

Calculated (%): C 63.07; H 5.15; O 31.78

Found (%): C 63.10; H 5.12; O 31.78

Compound 54

$^1$H -NMR (CDCl$_3$, δ-TMS): 10.21 (bs, 1H), 7.69 (d, 1H, J=8.4 Hz), 7.20–7.40 (m, 5H), 6.93 (s, 1H), 6.92 (d, 1H, J=8.4 Hz), 6.00 (s, 1H), 5.54 (m, 2H), 5.45 (s, 2H), 5.38 (m, 1H), 4.22 (m, 2H), 4.14 (s, 1H), 2.02–2.22 (m, 12H) IR (KBr, cm$^{-1}$): 3450, 1750, 1620, 1440, 1350, 1240

Elemental analysis:

Calculated (%): C 58.63; H 4.92; O 36.45

Found (%): C 58.61; H 4.94 ; O 36.45

Compound 55

$^1$H -NMR (CDCl$_3$, δ-TMS): 7.68 (d, 1H, J=8.4 Hz), 7.22–7.42 (m, 5H), 6.95 (s, 1H), 6.94 (d, 1H, J=8.4 Hz), 5.99 (s, 1H), 5.53 (m, 2H), 5.45 (s, 2H), 5.39 (m, 1H), 4.21 (m, 2H), 4.15 (s, 1H), 2.40 (s, 3H), 2.02–2.22 (m, 12H) IR (KBr, cm$^{-1}$): 1750, 1610, 1430, 1360, 1240

Elemental analysis:

Calculated (%): C 58.54; H 4.91; O 36.55

Found (%): C 58.55; H 4.92; O 36.53

Compound 56

$^1$H-NMR (CDCl$_3$, δ-TMS): 7.69 (d, 1H, J=8.4 Hz), 7.22–7.42 (m, 5H), 6.95 (s, 1H), 6.93 (d, 1H, J=8.4 Hz), 6.02 (s, 1H), 5.40–5.60 (m, 7H), 4.25 (m, 2H) 4.12 (s, 1H), 4.01 (t, 2H, J=6.8 Hz), 2.00–2.20 (m, 12H), 1.50–2.42 (m, 4H), 0.89 (t, 3H, J=6.8 Hz) IR (KBr, cm$^{-1}$): 2910, 1750, 1630, 1430, 1360, 1240

Elemental analysis:

Calculated (%): C 62.06; H 5.79; O 32.15

Found (%): C 62.03; H 5.81 ; O 32.16

Compound 57

$^1$H-NMR (CDCl$_3$, δ-TMS): 7.66 (d, 1H, J=8.4 Hz), 7.22–8.12 (m, 10H), 6.96 (s, 1H), 6.94 (d, 1H, J=8.4 Hz), 6.03 (s, 1H), 5.45–5.55 (m, 6H), 5.41 (m, 1H), 4.23 (m, 2H), 4.15 (s, 1H), 2.01–2.21 (m, 12H) IR (KBr, cm$^{-1}$): 1750, 1620, 1435, 1370, 1230

Elemental analysis:

Calculated (%): C 63.07; H 5.15; O 31.78

Found (%): C 63.10; H 5.11 ; O 31.79

Compound 66

$^1$H -NMR (DMSO-d$_6$, δ-TMS): 9.30 (bs, 1H), 7.75 (d, 1H, J=9.6 Hz), 6.80–7.00 (m, 2H), 5.80 (bs, 1H), 5.38 (d, 1H, J-7.2 Hz), 5.17 (d, 1H, J-4.4 Hz), 5.01 (d, 1H, J=4.4 Hz), 4.46 (bs, 1H), 4.02 (t, 2H, J=6.8 Hz), 3.10–3.70 (m, 6H), 1.20–1.80 (m, 12H), 0.87 (t, 3H, J=6.8 Hz) IR (KBr, cm$^{-1}$): 3400, 2900, 1680, 1620, 1320 Melting point: 167°–169° C.

Elemental analysis:

Calculated (%): C 58.96, H 6.89, O 34.15

Found (%): C 58.99, H 6.85, O 34.16

Compound 67

$^1$H -NMR (DMSO-d$_6$, δ-TMS): 9.40 (bs, 1H), 7.74 (d, 1H, J=9.6 Hz), 6.80–7.00 (m, 2H), 5.75 (bs, 1H), 5.38 (d, 1H, J=7.2 Hz), 5.17 (d, 1H, J=4.4Hz), 5.01 (d, 1H, J=4.4 Hz), 4.46 (s, 1H), 4.01 (t, 2H, J=6.8 Hz), 3.10–3.70 (m, 6H), 1.20–1.80 (m, 16H), 0.86 (t, 3H, J=6.8 Hz) IR (KBr, cm$^{-1}$): 3400, 2900, 2850, 1680, 1630, 1360

Elemental analysis:

Calculated (%): C 60.47, H 7.31, O 32.22

Found (%): C 60.45, H 7.36, O 32.19

Compound 68

$^1$H-NMR (DMSO-d$_6$, δ-TMS): 9.30 (bs, 1H), 7.74 (d, 1H, J=9.6 Hz), 6.80–7.00 (m, 2H), 5.82 (bs, 1H), 5.39 (d, 1H, J=7.2 Hz), 5.16 (d, 1H, J=4.4 Hz), 5.01 (d, 1H, J=4.4 Hz), 4.46 (s, 1H), 4.02 (t, 2H, J=6.8 Hz), 3.10–3.70 (m, 6H), 1.20–1.80 (m, 20H), 0.85 (t, 3H, J=6.8 Hz) IR (KBr, cm$^{-1}$): 3400, 2900, 2850, 1670, 1630, 1260 Melting point: 171°–172° C.

Elemental analysis:

Calculated (%): C 61.81, H 7.69, O 30.50

Found (%): C 61.92, H 7.52, O 30.56

Compound 69

$^1$H-NMR (DMSO-d$_6$, δ-TMS): 9.35 (bs, 1H), 7.71 (d, 1H, J=9.6 Hz), 6.80–7.00 (m, 2H), 5.80 (bs, 1H), 5.40 (d, 1H, J=7.2 Hz), 5.15 (d, 1H, J=4.4 Hz), 5.01 (d, 1H, J=4.8 Hz), 4.46 (s, 1H), 4.10 (m, 1H), 3.10–3.70 (m, 6H), 1.10 (d, 6H, J=7.0 Hz) IR (KBr, cm$^{-1}$): 3400, 2900, 2800, 1680, 1630, 1260

Elemental analysis:

Calculated (%): C 54.27, H 5.57, O 40.16

Found (%): C 54.28, H 5.54, O 40.18

Compound 70

$^1$H-NMR (DMSO-d$_6$, δ-TMS): 9.32 (bs, 1H), 7.71 (d, 1H, J=9.6 Hz), 6.80–7.00 (m, 2H), 5.90 (bs, 1H), 5.40–5.60 (m, 2H), 5.38 (d, 1H, J=7.2 Hz), 5.17 (d, 1H, J=4.4 Hz), 5.01 (d, 1H, J=4.4 Hz), 4.46 (s, 1H), 4.02 (t, 2H, J=6.8 Hz), 3.10–3.70 (m, 6H), 2.10–2.40 (m, 4H), 0.87 (t, 3H, J=6.8 Hz) IR (KBr, cm$^{-1}$): 3400, 2900, 1680, 1620, 1320

Elemental analysis:

Calculated (%): C 57.53, H 5.98, O 36.49

Found (%): C 57.59, H 5.97, O 36.44

Compound 71

$^1$H-NMR (DMSO-d$_6$, δ-TMS): 9.30 (bs, 1H), 7.72 (d, 1H, J=9.6 Hz), 6.80–7.00 (m, 2H), 5.90 (bs, 1H), 5.40–5.60 (m, 2H), 5.38 (d, 1H, J=7.2 Hz), 5.17 (d, 1H, J=4.4 Hz), 5.01 (d, 1H, J=4.8 Hz), 4.46 (s, 1H), 4.10 (d, 2H, J=7.0 Hz), 3.10–3.70 (m, 6H), 1.70–2.40 (m, 4H), 1.55–1.85 (m, 9H) IR (KBr, cm$^{-1}$): 3400, 2900, 2800, 1670, 1620, 1220

Elemental analysis:

Calculated (%): C 60.96, H 6.55, O 32.49

Found (%): C 60.99, H 6.57, O 32.44

Compound 72

$^1$H-NMR (DMSO-d$_6$, δ-TMS): 9.35 (bs, 1H), 7.70–8.10 (m, 2H), 7.40–7.65 (m, 4H), 6.80–7.00 (m, 2H), 5.80 (bs, 1H), 5.38 (d, 1H, J=7.2 Hz), 5.15 (d, 1H, J=4.4 Hz), 5.01 (d, 1H, J=4.4 Hz), 4.46 (s, 1H), 3.10–3.70 (m, 6H) IR (KBr, cm$^{-1}$): 3400, 2900, 1700, 1680, 1620, 1320

Elemental analysis:

Calculated (%): C 57.39, H 4.35, O 38.26

Found (%): C 57.34, H 4.37, O 38.29

Compound 73

$^1$H-NMR (DMSO-d$_6$, δ-TMS): 7.70–8.10 (m, 2H), 7.40–7.65 (m, 4H) 6.80–7.00 (m, 2H), 5.80 (bs, 1H), 5.38 (d, 1H, J=7.2 Hz), 5.15 (d, 1H, J=4.4 Hz), 5.01 (d, 1H, J=4.8 Hz), 4.46 (s, 1H), 3.82 (s, 3H), 3.10–3.70 (m, 6H) IR (KBr, cm$^{-1}$): 3400, 2900, 1720, 1680, 1620, 1320

Elemental analysis:

Calculated (%): C 58.23, H 4.64, O 37.13

Found (%): C 58.24, H 4.71, O 37.05

Compound 74

$^1$H-NMR (DMSO-d$_6$, δ-TMS): 7.78 (d, 1H, J=9.6 Hz), 6.80–7.00 (m, 2H), 5.80 (bs, 1H), 5.38 (d, 1H, J=7.2 Hz), 5.17 (d, 1H, J=4.4 Hz), 5.01 (d, 1H, J=4.4 Hz), 4.46 (s, 1H), 4.10 (t, 2H, J=7.9 Hz), 3.10–3.70 (m, 6H), 2.36 (s, 3H), 1.20–1.70 (m, 4H), 0.94 (t, 3H, J=7.9 Hz) IR (KBr, cm$^{-1}$): 3400, 2950, 2800, 1780, 1680, 1610

Elemental analysis:

Calculated (%): C 55.50, H 5.77, O 38.73

Found (%): C 55.48, H 5.81, O 38.71

Compound 75

$^1$H-NMR (DMSO-d$_6$, δ-TMS): 7.77 (d, 1H, J=9.6 Hz), 6.80–7.00 (m, 2H), 5.83 (bs, 1H), 5.38 (d, 1H, J=7.2 Hz), 5.17 (d, 1H, J=4.4 Hz), 5.01 (d, 1H, J=4.4 Hz), 4.46 (s, 1H), 4.01 (t, 2H, J=6.8 Hz), 3.10–3.70 (m, 6H), 2.31 (s, 3H), 1.20–1.80 (m, 20H), 0.85 (t, 3H, J=6.8 Hz) IR (KBr, cm$^{-1}$): 3400, 2950, 2800, 1780, 1680, 1610

Elemental analysis:

Calculated (%): C 61.48, H 7.42, O 31.10

Found (%): C 61.42, H 7.51, O 31.07

Compound 76

$^1$H-NMR (DMSO-d$_6$, δ-TMS): 9.35 (bs, 1H), 7.40–7.65 (m, 6H), 6.80–7.00 (m, 2H), 5.80 (bs, 1H, ), 5.45 (s, 2H), 5.38 (d, 1H, J=7.2 Hz), 5.15 (d, 1H, J=4.4 Hz), 5.01 (d, 1H, J=4.4 Hz), 4.46 (s, 1H), 3.10–3.70 (m, 6H) IR (KBr, cm$^{-1}$): 3400, 2900, 1720, 1680, 1620, 1320

Elemental analysis:

Calculated (%): C 59.19, H 4.97, O 35.84

Found (%): C 59.34, H 4.87, O 35.79

Compound 77

$^1$H-NMR (DMSO-d$_6$, δ-TMS): 10.18 (bs, 1H), 9.45 (bs, 1H), 7.60 (d, 1H, J=8.8 Hz), 6.80–7.00 (m, 2H), 6.16 (s, 1H), 5.18 (bs, 1H, ), 4.97 (s, 1H), 4.75 (s, 1H), 4.39 (s, 1H), 3.10–3.90 (m, 6H) IR (KBr, cm$^{-1}$): 3350, 1640, 1610, 1520, 1260

Elemental analysis:

Calculated (%): C 50.56, H 4.53, O 44.91

Found (%): C 50.51, H 4.55, O 44.94

Compound 78

$^1$H-NMR (DMSO-d$_6$, δ-TMS): 9.44 (bs, 1H), 7.61 (d, 1H, J=8.8 Hz), 6.80–7.00 (m, 2H), 6.16 (d, 1H, J=1.2 Hz), 5.17 (bs, 1H), 5.00 (s, 1H), 4.71 (s, 1H), 4.36 (s, 1H), 3.82 (s, 3H), 3.10–3.70 (m, 6H) IR (KBr, cm$^{-1}$): 3350, 1700, 1640, 1520, 1270

Elemental analysis:

Calculated (%): C 51.89, H 4.90, O 43.21

Found (%): C 51.92, H 4.85, O 43.23

Compound 79

$^1$H-NMR (DMSO-d$_6$, δ-TMS): 9.39 (bs, 1H), 7.62 (d, 1H, J=8.8 Hz), 6.80–7.00 (m, 2H), 6.14 (s, 1H), 5.17 (s, 1H), 5.00 (s, 1H), 4.74 (s, 1H), 4.34 (s, 1H), 4.11 (t, 2H, J=7.9 Hz), 3.10–3.70 (m, 6H), 1.20–1.70 (m, 4H), 0.95 (t, 3H, J=7.9 Hz) IR (KBr, cm$^{-1}$): 3320, 2900, 1700, 1640, 1610, 1220

Elemental analysis:

Calculated (%): C 55.33, H 5.87, O 38.80

Found (%): C 55.37, H 5.82, O 38.81

Compound 80

$^1$H-NMR (DMSO-d$_6$, δ-TMS): 9.45 (bs, 1H), 7.60 (d, 1H, J=9.2 Hz), 6.80–7.00 (m, 2H), 6.16 (s, 1H), 5.15 (s, 1H, ), 4.91 (s, 1H), 4.77 (s, 1H), 4.40 (s, 1H), 4.03 (t, 2H, J=7.2 Hz ), 3.10–3.70 (m, 6H), 1.20–1.80 (m, 12H), 0.86 (t, 3H, J=7.2 Hz) IR (KBr, cm$^{-1}$): 3400, 2900, 2850, 1700, 1640, 1610, 1260 Melting point: 118°–120° C.

Elemental analysis:

Calculated (%): C 58.96, H 6.89, O 34.15

Found (%): C 59.00, H 6.85, O 34.15

Compound 81

$^1$H-NMR (DMSO-d$_6$, δ-TMS): 9.43 (bs, 1H), 7.61 (d, 1H, J=9.2 Hz), 6.80–7.00 (m, 2H), 6.14 (s, 1H), 5.11 (s, 1H, ), 4.97 (s, 1H), 4.71 (s, 1H), 4.36 (s, 1H), 4.01 (t, 2H, J=7.2 Hz), 3.10–3.70 (m, 6H), 1.20–1.80 (m, 16H), 0.87 (t, 3H, J=7.2 Hz) IR (KBr, cm$^{-1}$): 3400, 2900, 2850, 1690, 1630, 1610, 1360

Elemental analysis:

Calculated (%): C 60.47, H 7.32, O 32.22

Found (%): C 60.49, H 7.27, O 32.24

Compound 82

$^1$H-NMR (DMSO-$d_6$, δ-TMS): 9.38 (bs, 1H), 7.60 (d, 1H, J=9.2 Hz), 6.80–7.00 (m, 2H), 6.16 (s, 1H), 5.10 (s, 1H), 4.96 (d, 1H), 4.71 (s, 1H), 4.36 (s, 1H), 4.02 (t, 2H, J=7.2 Hz), 3.10–3.70 (m, 6H), 1.20–1.80 (m, 20H), 0.85 (t, 3H, J=6.4 Hz, J=7.2 Hz) IR (KBr, cm$^{-1}$): 3350, 2900, 2850, 1700, 1640, 1610, 1260

Elemental analysis:

Calculated (%): C 61.81, H 7.69, O 30.50

Found (%): C 61.79, H 7.70, O 30.51

Compound 83

$^1$H-NMR (DMSO-$d_6$, δ-TMS): 9.35 (bs, 1H), 7.61 (d, 1H, J=9.2 Hz), 6.80–7.00 (m, 2H), 6.16 (s, 1H), 5.15 (s, 1H), 4.95 (s, 1H), 4.71 (s, 1H), 4.37 (s, 1H), 3.85 (m, 1H), 3.10–3.70 (m, 6H), 1.10 (d, 6H, J=6.0 Hz) IR (KBr, cm$^{-1}$): 3400, 2900, 2850, 1690, 1630, 1600, 1260

Elemental analysis:

Calculated (%): C 54.27, H 5.57, O 40.16

Found (%): C 54.23, H 5.58, O 40.19

Compound 84

$^1$H-NMR (DMSO-$d_6$, δ-TMS): 9.32 (bs, 1H), 7.61 (d, 1H, J=9.2 Hz), 6.80–7.00 (m, 2H), 6.16 (s, 1H), 5.40–5.60 (m, 2H), 5.18 (s, 1H), 4.97 (s, 1H), 4.71 (s 1H), 4.36 (s, 1H), 4.00 (t, 2H, J=6.8 Hz), 3.10–3.70 (m, 6H), 1.70–2.40 (m 4H), 0.87 (t, 3H, J=6.0 Hz) IR (KBr, cm$^{-1}$): 3400, 2950, 1690, 1630, 1610, 1220

Elemental analysis:

Calculated (%): C 57.53, H 5.98, O 36.49

Found (%): C 57.58, H 5.97, O 36.45

Compound 85

$^1$H-NMR (DMSO-$d_6$, δ-TMS): 9.39 (bs, 1H), 7.62 (d, 1H, J=9.2 Hz), 6.80–7.00 (m, 2H), 6.15 (s, 1H), 5.40–5.60 (m, 2H), 5.18 (s, 1H), 4.99 (s, 1H), 4.71 (s, 1H), 4.40 (s, 1H), 4.11 (d, 2H, J=7.0 Hz), 3.10–3.70 (m, 6H), 1.56–2.40 (m, 13H) IR (KBr, cm$^{-1}$): 3400, 2900, 2850, 1690, 1630, 1600, 1220

Elemental analysis:

Calculated (%): C 60.96, H 6.55, O 32.49

Found (%): C 61.02, H 6.52, O 32.46

Compound 86

$^1$H-NMR (DMSO-$d_6$, δ-TMS): 9.40 (bs, 1H), 7.40–8.10 (m, 6H), 6.80–7.00 (m, 2H), 6.15 (s, 1H), 5.15 (s, 1H), 4.95 (s, 1H), 4.69 (s, 1H), 4.46 (s, 1H), 3.10–3.70 (m, 6H) IR (KBr, cm$^{-1}$): 3400, 2900, 1700, 1680, 1620, 1320

Elemental analysis:

Calculated (%): C 57.39, H 4.35, O 38.26

Found (%): C 57.38, H 4.42, O 38.20

Compound 87

$^1$H-NMR (DMSO-$d_6$, δ-TMS): 7.40–8.10 (m, 6H), 6.80–7.00 (m, 2H), 6.15 (d, 1H, J=1.2 Hz), 5.18 (s, 1H), 4.95 (s, 1H), 4.72 (s, 1H), 4.46 (s, 1H), 3.88 (s, 3H), 3.10–3.70 (m, 6H) IR (KBr, cm$^{-1}$): 3400, 2900, 1720, 1690, 1640, 1620, 1320

Elemental analysis:

Calculated (%): C 58.23, H 4.64, O 37.13

Found (%): C 58.24, H 4.70, O 37.06

Compound 88

$^1$H-NMR (DMSO-$d_6$, δ-TMS): 7.60 (d, 1H, J=9.2 Hz), 6.80–7.00 (m, 2H), 6.15 (s, 1H), 5.18 (s, 1H), 4.97 (s, 1 Hz), 4.75 (s, 1H), 4.46 (s, 1H), 4.10 (t, 2H, J=7.9 Hz), 3.10–3.70 (m, 6H), 2.36 (s, 3H), 1.20–1.70 (m, 4H), 0.94 (t, 3H, J=7.9 Hz), IR (KBr, cm$^{-1}$): 3400, 2950, 2800, 1780, 1690, 1630, 1610

Elemental analysis:

Calculated (%): C 55.50, H 5.77, O 38.73

Found (%): C 55.45, H 5.81, O 38.74

Compound 89

$^1$H-NMR (DMSO-$d_6$, δ-TMS): 7.61 (d, 1H, J=9.2 Hz), 6.80–7.00 (m, 2H), 6.16 (s, 1H), 5.18 (s, 1H), 4.99 (s, 1H), 4.70 (s, 1H), 4.36 (s, 1H), 4.00 (t, 2H, J=7.2 Hz), 3.10–3.70 (m, 6H), 2.32 (s, 3H), 1.20–1.80 (m, 20H), 0.85 (t, 3H, J=7.2 Hz) IR (KBr, cm$^{-1}$): 3400, 2950, 2800, 1780, 1700, 1640, 1610

Elemental analysis:

Calculated (%): C 61.48, H 7.42, O 31.10

Found (%): C 61.50, H 7.42, O 31.08

Compound 90

$^1$H-NMR (DMSO-$d_6$, δ-TMS): 9.40 (bs, 1H), 7.25–7.68 (m, 6H), 6.80–7.00 (m, 2H), 6.15 (s, 1H), 5.45 (s, 2H), 5.15 (s, 1H), 4.95 (s, 1H), 4.69 (s, 1H), 4.46 (s, 1H), 3.10–3.70 (m, 6H) IR (KBr, cm$^{-1}$): 3400, 2900, 1700, 1680, 1620, 1320

Elemental analysis:

Calculated (%): C 59.19, H 4.97, O 35.84

Found (%): C 59.25, H 4.85, O 35.90

Compound 91

$^1$H-NMR (DMSO-$d_6$, δ-TMS): 10.18 (bs, 1H), 9.35 (bs, 1H), 7.76 (d, 1H, J=8.8 Hz), 6.80–7.00 (m, 2H), 5.80 (s, 1H), 5..26 (d, 1H, J=8.0 Hz), 4.50–4.70 (m, 3H), 3.20–3.90 (m, 6H) IR (KBr, cm$^{-1}$): 3450, 3300, 1630, 1610, 1520, 1260

Elemental analysis:

Calculated (%): C 50.56, H 4.53, O 44.91

Found (%): C 50.60, H 4.50, O 44.90

Compound 92

$^1$H-NMR (DMSO-$d_6$, δ-TMS): 9.38 (bs, 1H), 7.75 (d, 1H, J=8.6 Hz), 6.80–7.00 (m, 2H), 5.76 (s, 1H), 5.27 (d, 1H, J=8.0 Hz), 4.50–4.70 (m, 3H), 3.83 (t, 3H), 3.20–3.80 (m, 6H) IR (KBr, cm$^{-1}$): 3450, 3300, 1680, 1630, 1600, 1520, 1270

Elemental analysis:

Calculated (%): C 51.89, H 4.90, O 43.21

Found (%): C 51.95, H 4.88, O 43.17

Compound 93

$^1$H-NMR (DMSO-$d_6$, δ-TMS): 9.41 (bs, 1H), 7.76 (d, 1H, J=8.6 Hz), 6.80–7.00 (m, 2H), 5.77 (s, 1H), 5.27 (d, 1H, J=8.0 Hz), 4.50–4.70 (m, 3H), 4.11 (t, 2H, J=7.9 Hz), 3.20–3.80 (m, 6H), 1.20–1.70 (m, 4H), 0.95 (t, 3H, J=7.9 Hz) IR (KBr, cm$^{-1}$): 3400, 3300, 2900, 1670, 1620, 1610, 1220

Elemental analysis:

Calculated (%): C 55.33, H 5.87, O 38.80

Found (%): C 55.33, H 5.83, O 38.84

Compound 94

$^1$H-NMR (DMSO-$d_6$, δ-TMS): 9.41 (bs, 1H), 7.76 (d, 1H, J=8.6 Hz), 6.80–7.00 (m, 2H), 5.85 (s, 1H), 5.20 (d, 1H, J=8.0 Hz), 4.50–4.70 (s, 3H), 4.02 (t, 2H, J=7.2 Hz ), 3.20–3.80 (m, 6H), 1.20–1.80 (m, 12H), 0.87 (t, 3H, J=7.2 Hz) IR (KBr, cm$^{-1}$): 3450, 3300, 2900, 2850, 1680, 1620, 1610, 1260 Melting point: 160°–162° C.

Elemental analysis:

Calculated (%): C 58.96, H 6.89, O 34.15

Found (%): C 59.02, H 6.85, O 34.13

Compound 95

$^1$H-NMR (DMSO-$d_6$, δ-TMS): 9.40 (bs, 1H), 7.76 (d, 1H, J=8.6 Hz), 6.80–7.00 (m, 2H), 5.84 (s, 1 Hz), 5.26 (d, 1H, J=8.0 Hz), 4.50–4.70 (m, 2H), 4.01 (t, 2H, J=7.2 Hz), 3.20–3.80 (m, 6H), 1.20–1.80 (m, 16H), 0.87 (t, 3H, J=7.2 Hz) IR (KBr, cm$^{-1}$): 3450, 3300, 2900, 2850, 1690, 1630, 1610, 1360

Elemental analysis:

Calculated (%): C 60.47, H 7.32, O 32.22

Found (%): C 60.50, H 7.27, O 32.23

Compound 96

$^1$H-NMR (DMSO-d$_6$, δ-TMS): 9.38 (bs, 1H), 7.77 (d, 1H, J=8.6 Hz), 6.80,–7.00 (m, 2H), 5.83 (s, 1H), 5.26 (d, 1H, J=8.0 Hz), 4.50–4.70 (m, 3H), 4.02 (t, 2H, J=7.2 Hz), 3.20–3.80 (m, 6H), 1.20–1.80 (m, 20H), 0.85 (t, 3H, J=7.2 Hz) IR (KBr, cm$^{-1}$): 3450, 3300, 2900, 2850, 1680, 1630, 1610, 1260

Elemental analysis:

Calculated (%): C 61.81, H 7.69, O 30.50

Found (%): C 61.77, H 7.69, O 30.54

Compound 97

$^1$H-NMR (DMSO-d$_6$, δ-TMS): 9.38 (bs, 1H), 7.75 (d, 1H, J=8.6 Hz), 6.80–7.00 (m, 2H), 5.85 (s, 1H), 5.25 (d, 1H, J=8.0 Hz), 4.50–4.80 (m, 3H), 3.85 (m, 1H), 3.20–3.80 (m, 6H), 1.10 (d, 6H, J=6.0 Hz) IR (KBr, cm$^{-1}$): 3400, 3350, 2900, 2850, 1690, 1630, 1600, 1260

Elemental analysis:

Calculated (%): C 54.27, H 5.57, O 40.16

Found (%): C 54.25, H 5.55, O 40.20

Compound 98

$^1$H-NMR (DMSO-d$_6$, δ-TMS): 9.42 (bs, 1H), 7.76 (d, 1H, J=8.6 Hz), 6.80–7.00 (m, 2H), 5.86 (s, 1H), 5.40–5.60 (m, 2H), 5.24 (d, 1H, J=8.0 Hz), 4.50–4.80 (m, 3H), 4.02 (t, 2H, J=6.8 Hz), 3.20–3.80 (m, 6H), 1.50–2.40 (m, 4H), 0.87 (t, 3H, J=6.8 Hz) IR (KBr, cm$^{-1}$): 3450, 3300, 2950, 1690, 1630, 1610, 1220

Elemental analysis:

Calculated (%): C 57.53, H 5.98, O 36.49

Found (%): C 57.49, H 6.01, O 36.50

Compound 99

$^1$H-NMR (DMSO-d$_6$, δ-TMS): 9.39 (bs, 1H), 7.77 (d, 1H, J=8.6 Hz), 6.80–7.00 (m, 2H), 5.84 (s, 1H), 5.40–5.60 (m, 2H), 5.25 (d, 1H, J=8.0 Hz), 4.50–4.80 (m, 3H), 4.10 (d, 2H, J=7.0 Hz), 3.20–3.80 (m, 6H), 1.70–2.40 (m, 4H), 1.50–1.85 (m, 9H) IR (KBr, cm$^{-1}$): 3400, 3350, 2900, 2850, 1680, 1630, 1610, 1220

Elemental analysis:

Calculated (%): C 60.96, H 6.55, O 32.49

Found (%): C 60.93, H 6.61, O 32.46

Compound 100

$^1$H-NMR (DMSO-d$_6$, δ-TMS): 9.40 (bs, 1H), 7.40–8.10 (m, 6H), 6.80–7.00 (m, 2H), 5.85 (s, 1H), 5.24 (d, 1H, J=8.0 Hz), 4.50–4.80 (m, 3H), 3.20–3.80 (m, 6H) IR (KBr, cm$^{-1}$): 3450, 2900, 1700, 1680, 1620, 1320

Elemental analysis:

Calculated (%): C 57.39, H 4.35, O 38.26

Found (%): C 57.41, H 4.33, O 38.26

Compound 101

$^1$H-NMR (DMSO-d$_6$, δ-TMS): 7.40–8.10 (m, 6H), 6.80–7.00 (m, 2H), 5.85 (s, 1H), 5.28 (d, 1H, J=8.0 Hz), 4.50–4.80 (m, 3H), 3.90 (s, 3H), 3.20–3.80 (m, 6H) IR (KBr, cm$^{-1}$): 3400, 2900, 2850, 1720, 1680, 1630, 1620, 1320

Elemental analysis:

Calculated (%): C 58.23, H 4.64, O 37.13

Found (%): C 58.22, H 4.72, O 37.06

Compound 102

$^1$H-NMR (DMSO-d$_6$, δ-TMS): 7.76 (d, 1H, J=9.2 Hz), 6.80–7.00 (m, 2H), 5.85 (s, 1H), 5.25 (d, 1, J=8.0 Hz), 4.50–4.80 (m, 3H), 4.10 (t, 2H, J=7.9 Hz), 3.20–3.80 (m, 6H), 2.36 (s, 3H), 1.20–1.70 (m, 4H), 0.94 (t, 3H, J=7.9 Hz) IR (KBr, cm$^{-1}$): 3400, 2950, 2800, 1780, 1670, 1630, 1610

Elemental analysis:

Calculated (%): C 55.50, H 5.77, O 38.73

Found (%): C 55.49, H 5.81, O 38.70

Compound 103

$^1$H-NMR (DMSO-d$_6$, δ-TMS): 7.77 (d, 1H, J=8.6 Hz), 6.80–7.00 (m, 2H), 5.86 (s, 1H), 5.26 (d, 1H, J=8.0 Hz), 4.50–4.80 (m, 3H), 4.00 (t, 2H, J=7.2 Hz), 3.20–3.80 (m, 6H), 2.32 (s, 3H), 1.20–1.80 (m, 20H), 0.85 (t, 3H, J=7.2 Hz) IR (KBr, cm$^{-1}$): 3400, 2950, 2850, 1780, 1680, 1620, 1610

Elemental analysis:

Calculated (%): C 61.48, H 7.42, O 31.10

Found (%): C 61.48, H 7.50, O 31.02

Compound 104

$^1$H-NMR (DMSO-d$_6$, δ-TMS): 9.40 (bs, 1H), 7.30–7.85 (m, 6H), 6.80–7.00 (m, 2H), 5.85 (s, 1H), 5.24 (d, 1H, J=8.0 Hz), 4.50–4.80 (m, 3H), 3.20–3.80 (m, 6H) IR (KBr, cm$^{-1}$): 3450, 2900, 1700, 1680, 1620, 1320

Elemental analysis:

Calculated (%): C 59.19, H 4.97, O 35.84

Found (%): C 59.18, H 4.85, O 35.97

Compound 105

$^1$H-NMR (DMSO-d$_6$, δ-TMS): 9.40 (bs, 1H), 7.77 (d, 1H, J=8.6 Hz), 6.80–7.00 m, 2H), 5.76 (s, 1H), 5.25 (d, 1H, J=8.0 Hz), 4.50–4.75 (m, 3H), 3.20–3.80 (m, 6H), 2.33 (s, 3H) IR (KBr, cm$^{-1}$): 3450, 1740, 1620, 1610, 1520, 1220

Elemental analysis:

Calculated (%): C 51.26, H 4.55, O 44.19

Found (%): C 51.28, H 4.50, O 44.22

Compound 106

$^1$H-NMR (DMSO-d$_6$, δ-TMS): 9.50 (bs, 1H), 7.60 (d, 1H, J=8.8 Hz), 6.80–7.00 (m, 2H), 6.16 (bs, 1H), 5.15 (s, 1H), 5.05 (s, 1H), 4.72 (s, 1H), 4.30 (s, 1H), 3.10–3.70 (m, 6H), 2.31 (s, 3H) IR (KBr, cm$^{-1}$): 3300, 1740, 1640, 1610, 1520, 1220

Elemental analysis:

Calculated (%): C 51.26, H 4.55, O 44.19

Found (%): C 51.21, H 4.56, O 44.23

Compound 107

$^1$H-NMR (DMSO-d$_6$, δ-TMS): 10.15 (bs, 1H), 7.77 (d, 1H, J=8.8 Hz), 6.80–7.00 (m, 2H), 5.83 (s, 1H), 5.25 (d, 1H, J=8.0 Hz), 4.50–4.80 (m, 3H), 3.20–3.80 (m, 6H), 2.43 (s, 3H) IR (KBr, cm$^{-1}$): 3450, 3290, 1750, 1630, 1600, 1510, 1260

Elemental analysis:

Calculated (%): C 51.26, H 4.55, O 44.19

Found (%): C 51.23, H 4.53, O 44.24

Compound 108

$^1$H-NMR (DMSO-d$_6$, δ-TMS): 10.21 (bs, 1H), 7.65 (d, 1H, J=8.4 Hz), 6.80–6.90 (m, 2H), 5.37 (d, 1H, J=7.2 Hz), 5.14 (s, 1H), 5.00 (s, 1H), 4.51 (s, 1H), 3.20–3.80 (m, 7H), 2.31 (s, 3H) IR (KBr, cm$^{-1}$): 3350, 1740, 1650, 1630, 1570, 1270

Elemental analysis:

Calculated (%): C 51.26; H 4.55; O 4.19

Found (%): C 51.23; H 4.56; O 4.21

Compound 109

$^1$H-NMR (DMSO-d$_6$, δ-TMS): 10.20 (bs, 1H), 7.61 (d, 1H, J=8.8 Hz), 6.90–7.10 (m, 2H), 6.15 (s, 1H), 5.15 (bs, 1H), 4.99 (s, 1H), 4.73 (s, 1 H), 4.41 (s, 1H), 3.10–3.80 (m, 6H), 2.42 (s, 3H) IR (KBr, cm$^{-1}$): 3350, 1740, 1640, 1600, 1530, 1260

Elemental analysis:

Calculated (%): C 51.26, H 4.55, O 44.19

Found (%): C 51.20, H 4.58, O 44.22

Compound 110

$^1$H-NMR (DMSO-$d_6$, δ-TMS): 7.73 (d, 1H, J=8.6 Hz), 6.80–7.00 (m, 2H), 5.88 (s, 1H), 5.50–5.70 (m, 2H), 5.21 (d, 1H, J=8.0 Hz), 4.50–4.70 (m, 3H), 4.00 (t, 2H, J=6.8 Hz), 3.20–3.80 (m, 6H), 1.50–2.50 (m, 7H), 0.89 (t, 3H, J=6.8 Hz) IR (KBr, cm$^{-1}$): 3300, 2930, 1740, 1680, 1630, 1610, 1220

Elemental analysis:

Calculated (%): C 57.50, H 5.87, O 36.63

Found (%): C 57.53, H 5.88, O 36.59

Compound 111

$^1$H-NMR (DMSO-$d_6$, δ-TMS): 7.69 (d, 1H, J=9.6 Hz), 6.70–7.00 (m, 2H), 5.95 (bs, 1H), 5.40–5.70 (m, 2H), 5.36 (d, 1H, J=7.2 Hz), 5.19 (d, 1H, J=4.4 Hz), 5.04 (d, 1H, J=4.4 Hz), 4.46 (s, 1H), 4.01 (t, 2H, J=6.8 Hz), 3.10–3.80 (m, 6H), 2.00–2.40 (m, 7H), 0.89 (t, 3H, J=6.8 Hz) IR (KBr, cm$^{-1}$): 3400, 2800, 1740, 1670, 1620, 1320

Elemental analysis:

Calculated (%): C 57.50, H 5.87, O 36.63

Found (%): C 57.48, H 5.85, O 36.67

Compound 112

$^1$H-NMR (DMSO-$d_6$, δ-TMS): 7.60 (d, 1H, J=9.2 Hz), 6.90–7.00 (m, 2H), 6.13 (s, 1H), 5.40–5.60 (m, 2H), 5.20 (s, 1H), 4.95 (s, 1H), 4.71 (s, 1H, ), 4.33 (s, 1H), 3.99 (t, 2H, J=6.8 Hz), 3.10–3.80 (m, 6H), 1.70–2.50 (m, 7H), 0.85 (t, 3H, J=6.0 Hz) IR (KBr, cm$^{-1}$): 3400, 2940, 1750, 1680, 1620, 1610, 1220

Elemental analysis:

Calculated (%): C 57.50, H 5.87, O 36.63

Found (%): C 57.51, H 5.89, O 36.60

Compound 113

$^1$H-NMR (DMSO-$d_6$, δ-TMS): 7.30–7.80 (m, 6H), 6.90–7.00 (m, 2H), 5.88 (s, 1H), 5.40 (s, 2H), 5.23 (d, 1H, J=8.0 Hz), 4.60–4.80 (m, 3H), 3.20–3.70 (m, 6H), 2.37 (s, 3H) IR (KBr, cm$^{-1}$): 3450, 2900, 1740, 1700, 1670, 1620, 1310

Elemental analysis:

Calculated (%): C 59.01, H 4.95, O 36.04

Found (%): C 58.99, H 4.93, O 36.08

Compound 114

$^1$H-NMR (DMSO-$d_6$, δ-TMS): 7.35–7.65 (m, 6H), 6.90–7.00 (m, 2H), 5.83 (bs, 1H, ), 5.44 (s, 2H), 5.40 (d, 1H, J=7.2 Hz), 5.13 (d, 1H, J=4.4 Hz), 4.99 (d, 1H, J=4.4 Hz), 4.48 (s, 1H), 3.10–3.80 (m, 6H), 2.43 (s, 3H) IR (KBr, cm$^{-1}$): 3400, 2800, 1750, 1720, 1680, 1 610, 1320

Elemental analysis:

Calculated (%): C 59.01, H 4.95, O 36.04

Found (%): C 59.03, H 4.90, O 35.07

Compound 115

$^1$H-NMR (DMSO-$d_6$, δ-TMS): 7.26–7.70 (m, 6H), 6.90–7.00 (m, 2H), 6.18 (s, 1H), 5.42 (s, 2H), 5.15 (s, 1H), 4.98 (s, 1H), 4.71 (s, 1H), 4.46 (s, 1H), 3.00–3.70 (m, 6H), 2.35 (s, 3H) IR (KBr, cm$^{-1}$): 3400, 2900, 1740, 1710, 1680, 1610, 1320

Elemental analysis:

Calculated (%): C 59.01, H 4.95, O 36.04

Found (%): C 59.06, H 4.91, O 36.03

Compound 116

$^1$H-NMR (DMSO-$d_6$, δ-TMS): 9.28 (bs, 1H), 7.63 (d, 1H, J=8.4 Hz), 6.70–6.90 (m, 2H), 5.35 (d, 1H, J=7.2 Hz), 5.17 (s, 1H), 5.01 (s, 1H), 4.49 (s, 1H), 3.10–3.80 (m, 7H), 2.31 (s, 3H) IR (KBr, cm$^{-1}$): 3340, 1750, 1650, 1620, 1580, 1270

Elemental analysis:

Calculated (%): C 51.26; H 4.55; O 4.19

Found (%): C 51.27; H 4.57; O 44.16

Compound 117

$^1$H-NMR (DMSO-$d_6$, δ-TMS): 7.80 (d, 1H, J=8.8 Hz), 6.80–7.10 (m, 2H), 5.85 (s, 1H), 5.23 (d, 1H, J=8.0 Hz), 4.60–4.80 (m, 3H), 3.20–3.90 (m, 6H), 2.41 (s, 3H), 2.20 (s, 3H) IR (KBr, cm$^{-1}$): 3290, 1750, 1620, 1600, 1520, 1250

Elemental analysis:

Calculated (%): C 51.82, H 4.58, O 43.60

Found (%): C 51.88, H 4.50, O 43.62

Compound 118

$^1$H-NMR (DMSO-$d_6$, δ-TMS): 7.64 (d, 1H, J=8.4 Hz), 6.80–7.00 (m, 2H), 5.33 (d, 1H, J=7.2 Hz), 5.20 (s, 1H), 4.99 (s, 1H), 4.52 (s, 1H), 3.00–3.70 (m, 7H), 2.35 (s, 3H), 2.22 (s, 3H) IR (KBr, cm$^{-1}$): 3350, 1740, 1650, 1630, 1580, 1260

Elemental analysis:

Calculated (%): C 51.82; H 4.58; O 43.60

Found (%): C 51.80; H 4.60; O 43.60

Compound 119

$^1$H-NMR (DMSO-$d_6$, δ-TMS): 7.59 (d, 1H, J=8.8 Hz), 6.90–7.00 (m, 2H), 6.12 (s, 1H), 5.20 (bs, 1H, ), 5.00 (s, 1H), 4.76 (s, 1H), 4.38 (s, 1H), 3.00–3.80 (m, 6H), 2.45 (s, 3H), 2.23 (s, 3H) IR (KBr, cm$^{-1}$): 3340, 1750, 1640, 1600, 1540, 1250

Elemental analysis:

Calculated (%): C 51.82, H 4.58, O 43.60

Found (%): C 51.86, H 4.53, O 43.61

Compound 120

$^1$H-NMR (DMSO-$d_6$, δ-TMS): 9.39 (bs, 1H), 7.73 (d, 1H, J=8.6 Hz), 6.90–7.10 (m, 2H), 5.75 (s, 1H), 5.28 (d, 1H, J=8.0 Hz), 4.50–4.70 (m, 3H), 4.12 (t, 2H, J=7.9 Hz), 3.10–3.80 (m, 6H), 1.20–1.80 (m, 8H), 0.93 (t, 3H, J=7.9 Hz) IR (KBr, cm$^{-1}$): 3400, 2900, 1680, 1620, 1610, 1210

Elemental analysis:

Calculated (%): C 57.26, H 6.41, O 36.33

Found (%): C 57.24, H 6.40, O 36.36

Compound 121

$^1$-NMR (DMSO-$d_6$, δ-TMS): 9.36 (bs, 1H), 7.74 (d, 1H, J=8.4 Hz), 6.80–6.90 (m, 2H), 5.40 (d, 1H, J=7.6 Hz), 5.15 (s, 1H), 5.01 (s, 1H), 4.46 (s, 1H), 4.13 (t, 2H, J=7.9 Hz), 3.00–3.70 (m, 7H), 1.10–1.70 (m, 8H), 0.92 (t, 3H, J=7.9 Hz) IR (KBr, cm$^{-1}$): 3430, 2920, 1660, 1610, 1280

Elemental analysis:

Calculated (%): C 57.26; H 6.41; O 36.33

Found (%): C 57.23; H 6.39 ; O 36.38

Compound 122

$^1$H-NMR (DMSO-$d_6$, δ-TMS): 9.37 (bs, 1H), 7.60 (d, 1H, J=8.8 Hz), 6.90–7.10 (m, 2H), 6.11 (s, 1H), 5.20 (s, 1H), 5.03 (s, 1H), 4.72 (s, 1H), 4.33 (s, 1H), 4.11 (t, 2H, J=7.9 Hz), 3.10–3.70 (m, 6H), 1.20–1.80 (m, 8H), 0.94 (t, 3H, J=7.9 Hz) IR (KBr, cm$^{-1}$): 3320, 2900, 1700, 1630, 1610, 1230

Elemental analysis:

Calculated (%): C 57.26, H 6.41, O 36.33

Found (%): C 57.23, H 6.43, O 36.34

Compound 123

$^1$H-NMR (DMSO-$d_6$, δ-TMS): 7.78 (d, 1H, J=9.2 Hz), 6.80–7.10 (m, 2H), 5.86 (s, 1H), 5.22 (d, 1, J=8.0 Hz), 4.50–4.80 (m, 3H), 4.09 (t, 2H, J=7.9 Hz), 3.10–3.70 (m, 6H), 2.39 (s, 3H), 1.10–1.70 (m, 8H), 0.95 (t, 3H, J=7.9 Hz) IR (KBr, cm$^{-1}$): 3400, 2940, 2800, 1770, 1670, 1620, 1610

Elemental analysis:

Calculated (%): C 55.41, H 6.07, O 38.52

Found (%): C 55.39, H 6.08, O 38.53

Compound 124

$^1$H-NMR (DMSO-d$_6$, δ-TMS): 7.79 (d, 1H, J=9.6 Hz), 6.80–7.00 (m, 2H), 5.83 (bs, 1H), 5.35 (d, 1H, J=7.2 Hz), 5.20 (d, 1H, J=4.4 Hz), 5.04 (d, 1H, J=4.4 Hz), 4.45 (s, 1H), 4.08 (t, 2H, J=7.9 Hz), 3.10–3.80 (m, 6H), 2.34 (s, 3H), 1.20–1.80 (m, 8H), 0.96 (t, 3H, J=7.9 Hz) IR (KBr, cm$^{-1}$): 3400, 2940, 2800, 1770, 1670, 1610

Elemental analysis:

Calculated (%): C 55.41, H 6.07, O 38.52

Found (%): C 55.43, H 6.05, O 38.52

Compound 125

$^1$H-NMR (DMSO-d$_6$, δ-TMS): 7.58 (d, 1H, J=9.2 Hz), 6.90–7.00 (m, 2H), 6.12 (s, 1H), 5.20 (s, 1H), 4.99 (s, 1 Hz), 4.72 (s, 1H), 4.42 (s, 1H), 4.10 (t, 2H, J=7.9 Hz), 3.10–3.80 (m, 6H), 2.33 (s, 3H), 1.10–1.70 (m, 8H), 0.95 (t, 3H, J=7.9 Hz) IR (KBr, cm$^{-1}$): 3400, 2940, 2800, 1760, 1690, 1620, 1610

Elemental analysis:

Calculated (%): C 55.41, H 6.07, O 38.52

Found (%): C 55.45, H 6.02, O 38.53

TEST EXAMPLE 1

Acute toxicity test in mice

We performed this test in order to confirm a degree of the safety on that the compounds of the present invention in the following, the method of the acute toxicity test will be explained.

Method: 3-glycosyloxybenzopyran derivatives (compound No. 3–45) and 4-glycosyloxybenzopyran derivatives (compound No. 59, 61, 63, 65–106, 116, 120–122) were forcibly administered orally at the doses of 1000 and 2000 mg/kg to Male ICR mice (body weight is 20–25 g, 5 mice per one(1) group), using an esophageal sound. After the administration, the animals were kept in cages for 7 days, to observed general symptoms and to count dead animals. Lethal dose (LD$_{50}$:mg/kg) was extrapolated from the mortality at 7th day after administration.

In result, the LD$_{50}$ of all compounds (both 3-glycosyloxybenzopyran derivatives and 4-glycosyloxybenzopyran derivatives) were over 2000 mg/kg, and therefore it was clearly shown that the compounds of the present invention have extremely low toxicity.

TEST EXAMPLE 2

Effect on homologous passive cutaneous anaphylaxis (PCA) reaction in rats

We performed this pharmacological test by PCA reaction which was well known screening test for anti-allergic agents in order to demonstrate that the compounds of the present invention possess anti-allergic activity. This experimental animal model is caused by immediate type allergic reaction, namely, antigen-antibody reaction. In the following, the method of this pharmacological test will be explained.

Method: Male wistar rats (9 weeks old) were intradermally administered 0.05 ml of anti-serum against trinitrophenylated ascaris (TNP-As) into two sites on the shaved dorsal skin. 48 hours later, 3-glycosyloxybenzopyran derivatives and 4-glycosyloxybenzopyran derivatives (test compounds) suspended in 0.5% sodium carboxymethylcellulose (CMCNa) were given orally at a dose of 100 mg/kg to the animals. 1 hour after administration of Test compounds, the animals were induced anaphylaxis by injection of saline (1 ml) dissolving 5 mg of Evans Blue and 1 mg of TNP-As into the tail vein of the animals. 30 minutes after induction of anaphylaxis, animals were anesthetized by ether and killed by bleeding, and were flayed dorsal skin. The leakage of dye was assessed by measuring the diameter (mean of shortest and longest diameter) of the blue spot on the inside surface of dorsal skin. As vehicle control group, only 0.5% CMCNa solution was administered orally, and as positive control group, Tranilast suspended in 0.5% CMCNa were administered orally at a dose of 100 mg/kg to the animals with the same method as the test compounds groups. The inhibition (%) of PCA reaction was calculated according to equation 1 and the result was shown in Table 3. Each experimental group consisted of 5 rats.

$$\text{Inhibition (\%)} = \frac{A - B}{A} \times 100 \quad \text{(Equation 1)}$$

In equation 1:

A: leakage of dye in vehicle control group

B: leakage of dye in test compound group or in positive control group

TABLE 3

| compound No. | Inhibition (%) |
|---|---|
| compound 3 | 43.5 |
| compound 4 | 40.2 |
| compound 5 | 48.7 |
| compound 6 | 42.3 |
| compound 7 | 41.1 |
| compound 8 | 45.2 |
| compound 9 | 51.3 |
| compound 10 | 50.3 |
| compound 11 | 52.1 |
| compound 12 | 41.3 |
| compound 13 | 58.7 |
| compound 14 | 50.2 |
| compound 15 | 60.4 |
| compound 16 | 62.6 |
| compound 17 | 59.2 |
| compound 18 | 56.6 |
| compound 19 | 56.8 |
| compound 20 | 57.2 |
| compound 21 | 54.4 |
| compound 22 | 53.8 |
| compound 23 | 47.8 |
| compound 24 | 54.3 |
| compound 25 | 50.9 |
| compound 26 | 53.3 |
| compound 27 | 47.8 |
| compound 28 | 53.4 |
| compound 29 | 45.6 |
| compound 30 | 41.7 |
| compound 31 | 46.9 |
| compound 32 | 43.2 |
| compound 33 | 57.2 |
| compound 34 | 64.3 |
| compound 35 | 60.1 |
| compound 36 | 56.7 |
| compound 37 | 59.5 |
| compound 38 | 59.6 |
| compound 39 | 58.3 |
| compound 40 | 40.5 |
| compound 41 | 60.8 |
| compound 42 | 52.7 |
| compound 43 | 63.2 |
| compound 44 | 53.5 |
| compound 45 | 46.3 |
| compound 59 | 46.1 |
| compound 61 | 49.2 |
| compound 63 | 57.4 |
| compound 65 | 45.6 |
| compound 66 | 63.8 |
| compound 67 | 60.4 |
| compound 68 | 59.9 |
| compound 69 | 57.2 |
| compound 70 | 58.5 |
| compound 71 | 57.4 |
| compound 72 | 46.9 |
| compound 73 | 45.8 |
| compound 74 | 46.8 |

TABLE 3-continued

| compound No. | Inhibition (%) |
|---|---|
| compound 75 | 43.3 |
| compound 76 | 47.7 |
| compound 77 | 42.7 |
| compound 78 | 46.2 |
| compound 79 | 47.1 |
| compound 80 | 50.5 |
| compound 81 | 48.3 |
| compound 82 | 47.3 |
| compound 83 | 49.3 |
| compound 84 | 45.5 |
| compound 85 | 47.6 |
| compound 86 | 43.0 |
| compound 87 | 44.7 |
| compound 88 | 45.8 |
| compound 89 | 43.7 |
| compound 90 | 45.3 |
| compound 91 | 40.4 |
| compound 92 | 50.2 |
| compound 93 | 57.6 |
| compound 94 | 63.3 |
| compound 95 | 65.1 |
| compound 96 | 56.6 |
| compound 97 | 55.7 |
| compound 98 | 60.2 |
| compound 99 | 58.6 |
| compound 100 | 42.6 |
| compound 101 | 45.2 |
| compound 102 | 46.3 |
| compound 103 | 51.1 |
| compound 104 | 44.2 |
| compound 105 | 51.4 |
| compound 106 | 42.2 |
| compound 116 | 48.0 |
| compound 120 | 64.3 |
| compound 121 | 63.7 |
| compound 122 | 52.3 |
| Tranilast | 56.2 |

As shown in Table 3, it was demonstrated that all compounds of the present invention have equivalent or superior anti-allergic activity to Tranilast. The results of these examples clearly showed that the compounds of the present invention were useful anti-allergic agent for immediate type allergic disease.

COMPARATIVE TEST EXAMPLE 1

Effect on homologous passive cutaneous anaphylaxis (PCA) reaction in rats

The anti-allergic activity of the compounds of the present invention were compared with that of analogous compounds which were published in the Patent (EP-A-0598117) by PCA reaction. This pharmacological test was performed according to the method described in Test Example 1. The compared compounds were shown in Table 4 and the results were shown in Table 5.

TABLE 4

| Compared compound No. | Chemical name |
|---|---|
| Compared compound 1 | 4-hydroxy-3,7-dimethoxy-2H-1-benzopyran-2-one |
| Compared compound 2 | 3-methoxy-4-hydroxy-7-octyloxy-2H-1-benzopyran-2-one |
| Compared compound 3 | 3-hydroxy-4,7-dimethoxy-2H-1-benzopyran-2-one |
| Compared compound 4 | 3-hydroxy-4-methoxy-7-decyloxy-2H-1-benzopyran-2-one |

TABLE 5

| Compared compound No. | Inhibition (%) | Compound No. (of the present invention) | Inhibition (%) |
|---|---|---|---|
| Compared compound 1 | 28.9 | compound 5 | 48.7 |
| Compared compound 2 | 32.8 | compound 11 | 52.1 |
|  |  | compound 16 | 62.6 |
|  |  | compound 34 | 64.3 |
| Compared compound 3 | 30.6 | compound 61 | 49.2 |
| Compared compound 4 | 26.4 | compound 67 | 60.4 |
|  |  | compound 92 | 50.2 |
|  |  | compound 95 | 65.1 |

From the results of the Test Example 2 and this Comparative Test Example, it is clear that the anti-allergic activity of the compounds of the present invention, 3-glycoside and 4-glycoside, were higher than that of the compared compounds.

TEST EXAMPLE 3

Effect on contact dermatitis induced by picryl chloride in mice

We performed this pharmacological test by experimental contact dermatitis model which is well known in order to demonstrate that the compounds of the present invention suppress the delayed type hypersensitization. This experimental animal model which is typical delayed type hypersensitization model, was mainly caused by cellular immune response (Immunology, Vol. 15, P. 405–416, 1968). The delayed type hypersensitization is inhibited by steroid, but can not be effected by known anti-allergic agents. In the following, the method of the pharmacological test will be explained.

Method: Mice, shaved their abdominal skin on previous day, were immunized by applying 0.1 ml of acetone containing 7 mg of picryl chloride to the skin of the abdomen. 7 days after immunization, the thickness of the ear was measured with a dial thickness gauge, then mice were challenged by painting 5 µl of 1% picryl chloride olive oil solution to each side skin of left ear. 24 hours after challenge, the thickness of the left ear was measured again and the increase (%) of thickness was calculated according to equation 2. The compounds of the present invention (test compounds) suspended in 0.5% CMCNa were forcibly administered orally at a dose of 100 mg/kg at 1 hour before and 16 hours after challenge. As vehicle control group, only 0.5% CMCNa solution were administered orally, and as positive control group, Prednisolone, steroid hormone, and Tranilast were administered orally at the doses of 10 mg/kg and 100 mg/kg, respectively. The inhibition (%) against the increase of thickness in vehicle control group were calculated according to equation 2 and 3, the result was shown in Table 6.

(Equation 2)

$$\text{Increase } (\%) = (A-B)/B \times 100$$

In equation 2:
A: thickness of the ear at 24 hours after challenge
B: thickness of the ear before challenge
(equation 3)

$$\text{Inhibition}(\%) = (C-D)/C \times 100$$

In equation 3:
C: The increase (%) in vehicle control group

D: The increase (%) in test compounds group or positive control group

TABLE 6

| Compound No. | Inhibition (%) |
|---|---|
| compound 3 | 40.5 |
| compound 4 | 46.3 |
| compound 5 | 51.2 |
| compound 6 | 41.9 |
| compound 7 | 40.3 |
| compound 8 | 45.3 |
| compound 9 | 50.1 |
| compound 10 | 47.5 |
| compound 11 | 53.3 |
| compound 12 | 40.8 |
| compound 13 | 50.4 |
| compound 14 | 47.5 |
| compound 15 | 58.5 |
| compound 16 | 64.0 |
| compound 17 | 59.2 |
| compound 18 | 56.9 |
| compound 19 | 57.4 |
| compound 20 | 56.2 |
| compound 21 | 53.6 |
| compound 22 | 53.4 |
| compound 23 | 45.0 |
| compound 24 | 52.6 |
| compound 25 | 57.3 |
| compound 26 | 55.9 |
| compound 27 | 51.2 |
| compound 28 | 50.3 |
| compound 29 | 53.6 |
| compound 30 | 48.7 |
| compound 31 | 48.6 |
| compound 32 | 48.1 |
| compound 33 | 62.5 |
| compound 34 | 64.2 |
| compound 35 | 61.1 |
| compound 36 | 58.2 |
| compound 37 | 58.3 |
| compound 38 | 57.6 |
| compound 39 | 54.3 |
| compound 40 | 41.3 |
| compound 41 | 65.7 |
| compound 42 | 52.1 |
| compound 43 | 63.4 |
| compound 44 | 58.2 |
| compound 45 | 46.3 |
| compound 59 | 45.6 |
| compound 61 | 50.7 |
| compound 63 | 57.1 |
| compound 65 | 46.3 |
| compound 66 | 62.5 |
| compound 67 | 63.8 |
| compound 68 | 56.6 |
| compound 69 | 56.4 |
| compound 70 | 57.6 |
| compound 71 | 57.1 |
| compound 72 | 47.8 |
| compound 73 | 45.8 |
| compound 74 | 47.0 |
| compound 75 | 46.2 |
| compound 76 | 46.8 |
| compound 77 | 39.6 |
| compound 78 | 43.1 |
| compound 79 | 46.3 |
| compound 80 | 50.3 |
| compound 81 | 50.8 |
| compound 82 | 48.7 |
| compound 83 | 49.1 |
| compound 84 | 46.3 |
| compound 85 | 47.2 |
| compound 86 | 39.1 |
| compound 87 | 42.4 |
| compound 88 | 40.2 |
| compound 89 | 41.2 |
| compound 90 | 38.4 |
| compound 91 | 45.5 |
| compound 92 | 52.6 |
| compound 93 | 59.9 |
| compound 94 | 64.7 |
| compound 95 | 65.1 |
| compound 96 | 57.8 |
| compound 97 | 58.7 |
| compound 98 | 61.2 |
| compound 99 | 59.4 |
| compound 100 | 44.9 |
| compound 101 | 47.2 |
| compound 102 | 46.3 |
| compound 103 | 48.3 |
| compound 104 | 46.1 |
| compound 105 | 47.8 |
| compound 106 | 40.1 |
| compound 116 | 45.1 |
| compound 120 | 65.2 |
| compound 121 | 63.7 |
| compound 122 | 53.2 |
| Prednisolone | 63.5 |
| Tranilast | 11.5 |

It was observed that test compounds effectively inhibit the swelling of the ear by 40–65% against that in vehicle control group. Many of the compounds of the present invention were equivalent or superior to Prednisolone (Inhibition: 63.5%). In contrast, Tranilast, used widely for allergic disease, did not inhibit delayed type hypersensitization. These results clearly show that the compounds of the present invention have exceedingly inhibitory activity against delayed type hypersensitization. And therefore the compounds of the present invention are exceedingly useful anti-allergic agent.

TEST EXAMPLE 4

Effect on exprimental asthma model in guinea pigs

The asthma is typical allergic disease and we carried out this pharmacological test by well known experimental asthma model in guinea pigs in order to confirm that the compounds of the present invention suppress the asthma. In the following, the method of the pharmacological test will be explained.

Method: Male hadley guinea pigs were immunized by intraperitoneal injection of saline (1 ml) containing 5 mg of ovalbumine (OVA) three times at interval of one week. 2 weeks after final immunization, the animals were challenged by inhalation of 1% OVA-saline solution for 1 minute and then the airway resistance of the animals were measured for 30 minutes with PULMOS-1 (Medical Interface Project Station Inc.) after the inhalation. The compounds of the present invention (test compounds) suspended in 0.5% CMCNa were given orally at a dose of 100 mg/kg. As positive control group, Disodium Cromoglicate (DSCG), well known anti-allergic agent, in saline were injected at a dose of 20 mg/kg into the vein of the animals. As vehicle control group, only 0.5% CMCNa solution were given orally. The inhibition (%) of the airway resistance in vehicle control group was calculated according to equation 5 and the result was shown in Table 7. Each experimental group consisted of 5 guinea pigs.

$$\text{Inhibition (\%)} = \frac{A - B}{A} \quad \text{(equation 5)}$$

In equation 5:
A: Maximum airway resistance in vehicle control group

B: Maximum airway resistance in test compounds group or positive control group

TABLE 7

| compound No. | Inhibition (%) |
|---|---|
| compound 3 | 40.0 |
| compound 4 | 48.3 |
| compound 5 | 62.0 |
| compound 6 | 38.5 |
| compound 7 | 43.7 |
| compound 8 | 46.7 |
| compound 9 | 58.4 |
| compound 10 | 49.0 |
| compound 11 | 63.3 |
| compound 12 | 39.2 |
| compound 13 | 57.7 |
| compound 14 | 52.3 |
| compound 15 | 73.6 |
| compound 16 | 75.8 |
| compound 17 | 75.0 |
| compound 18 | 70.3 |
| compound 19 | 73.1 |
| compound 20 | 72.4 |
| compound 21 | 60.7 |
| compound 22 | 59.4 |
| compound 23 | 46.6 |
| compound 24 | 58.3 |
| compound 25 | 68.6 |
| compound 26 | 66.3 |
| compound 27 | 56.7 |
| compound 28 | 57.2 |
| compound 29 | 56.1 |
| compound 30 | 47.8 |
| compound 31 | 53.5 |
| compound 32 | 54.8 |
| compound 33 | 68.1 |
| compound 34 | 78.3 |
| compound 35 | 75.2 |
| compound 36 | 66.4 |
| compound 37 | 72.4 |
| compound 38 | 73.7 |
| compound 39 | 64.1 |
| compound 40 | 46.2 |
| compound 41 | 77.7 |
| compound 42 | 62.6 |
| compound 43 | 76.3 |
| compound 44 | 71.2 |
| compound 45 | 46.5 |
| compound 59 | 49.1 |
| compound 61 | 53.3 |
| compound 63 | 64.7 |
| compound 65 | 46.9 |
| compound 66 | 74.1 |
| compound 67 | 70.6 |
| compound 68 | 65.3 |
| compound 69 | 68.3 |
| compound 70 | 67.7 |
| compound 71 | 65.2 |
| compound 72 | 49.5 |
| compound 73 | 44.7 |
| compound 74 | 55.4 |
| compound 75 | 45.2 |
| compound 76 | 47.5 |
| compound 77 | 37.3 |
| compound 78 | 50.8 |
| compound 79 | 50.3 |
| compound 80 | 63.3 |
| compound 81 | 63.1 |
| compound 82 | 55.1 |
| compound 83 | 46.9 |
| compound 84 | 47.1 |
| compound 85 | 48.5 |
| compound 86 | 41.2 |
| compound 87 | 42.5 |
| compound 88 | 43.5 |
| compound 89 | 43.2 |
| compound 90 | 40.5 |
| compound 91 | 45.1 |
| compound 92 | 57.7 |
| compound 93 | 60.5 |

TABLE 7-continued

| compound No. | Inhibition (%) |
|---|---|
| compound 94 | 82.6 |
| compound 95 | 75.4 |
| compound 96 | 73.1 |
| compound 97 | 63.2 |
| compound 98 | 72.8 |
| compound 99 | 77.7 |
| compound 100 | 67.8 |
| compound 101 | 56.2 |
| compound 102 | 50.3 |
| compound 103 | 65.3 |
| compound 104 | 63.3 |
| compound 105 | 58.8 |
| compound 106 | 46.2 |
| compound 116 | 55.3 |
| compound 120 | 78.9 |
| compound 121 | 75.1 |
| compound 122 | 62.1 |
| DSCG | 50.5 |

As shown in Table 7, the compounds of the present invention administered orally inhibited the increase of the airway resistance by 40–80%. Therefore the compounds of the present invention have exceedingly high activity to treat for the asthma.

FORMULATION EXAMPLE 1

| (5% powders) | |
|---|---|
| compound 34 | 50 mg |
| lactose | 950 mg |
| | 1000 mg |

Crystals of the compound 34 were pulverized in a mortar and thoroughly mixed with lactose by pulverizing the mixture with a pestle to obtain 5% powders.

FORMULATION EXAMPLE 2

| (5% powders) | |
|---|---|
| compound 66 | 50 mg |
| lactose | 950 mg |
| | 1000 mg |

The procedure of Formulation Example 1 was repeated to obtain 5% powders.

FORMULATION EXAMPLE 3

| (10% granules) | |
|---|---|
| compound 43 | 300 mg |
| lactose | 2000 mg |
| starch | 670 mg |
| gelatin | 30 mg |
| | 3000 mg |

The compound 43 was mixed with the same amount of starch and pulverized in a mortar. This was further mixed with lactose and the remaining portion of starch. Separately from this, 30 mg of gelatin was mixed with 1 ml of purified water, solubilized by heating, cooled and then, with stirring, mixed with 1 ml of ethanol to prepare a gelatin solution. Thereafter, the mixture prepared above was mixed with the gelatin solution, and the resulting mixture was kneaded, granulated and then dried to obtain granules.

FORMULATION EXAMPLE 4

| (10% granules) | |
|---|---|
| compound 94 | 300 mg |
| lactose | 2000 mg |
| starch | 670 mg |
| gelatin | 30 mg |
| | 3000 mg |

The procedure of Formulation Example 3 was repeated to obtain 10% granules.

FORMULATION EXAMPLE 5

| (5 mg tablets) | |
|---|---|
| compound 19 | 5 mg |
| lactose | 62 mg |
| starch | 30 mg |
| talc | 2 mg |
| magnesium stearate | 1 mg |
| | 100 mg/tablet |

A 20 times larger portion of the above composition was used to prepare tablets each of which containing 5 mg of the compound 19. That is, 100 mg of the compound 19 in a crystal form was pulverized in a mortar and mixed with lactose and starch. The thus prepared formulation was mixed with 10% starch paste, and the mixture was kneaded and then subjected to granulation. After drying, the resulting granules were mixed with talc and magnesium stearate and subjected to tablet making in the usual way.

FORMULATION EXAMPLE 6

| (5 mg tablets) | |
|---|---|
| compound 80 | 5 mg |
| lactose | 62 mg |
| starch | 30 mg |
| talc | 2 mg |
| magnesium stearate | 1 mg |
| | 100 mg/tablet |

The procedure of Formulation Example 5 was repeated to obtain 5 mg tablets.

FORMULATION EXAMPLE 7

| (20 mg tablets) | |
|---|---|
| compound 38 | 20 mg |
| 6% hydroxypropylcellulose/lactose | 75 mg |
| stearate/talc | 2 mg |
| potato starch | 3 mg |
| | 100 mg/tablet |

A 10 times larger portion of the above composition was used to prepare tablets each of which containing 20 mg of the active ingredient. That is, 6 g of hydroxypropylcellulose was dissolved in an appropriate volume of ethanol and mixed with 94 g of lactose, followed by kneading. After drying to a degree, the mixture was passed through a No. 60 mesh, and the thus graded granules were used as 6% hydroxypropylcellulose/lactose. Separately from this, magnesium stearate and talc were mixed at a ratio of 1:4 and used as stearate/talc. Thereafter, the compound 38, 6% hydroxypropylcellulose/lactose, stearate/talc and potato starch were thoroughly mixed and subjected to tablet making in the usual way.

FORMULATION EXAMPLE 8

| (20 mg tablets) | |
|---|---|
| compound 98 | 20 mg |
| 6% hydroxypropylcellulose/lactose | 75 mg |
| stearate/talc | 2 mg |
| potato starch | 3 mg |
| | 100 mg/tablet |

The procedure of Formulation Example 7 was repeated to obtain 20 mg tablets.

FORMULATION EXAMPLE 9

| (25 mg tablets) | |
|---|---|
| compound 25 | 25 mg |
| lactose | 122 mg |
| carboxymethylstarch | 50 mg |
| talc | 2 mg |
| magnesium stearate | 1 mg |
| | 200 mg/tablet |

Ten times larger portions of the above compounds were put into a mortar to prepare tablets each of which containing 25 mg of the active ingredient. That is, 250 mg of the compound 25 in a crystal form was pulverized in a mortar and thoroughly mixed with lactose. An appropriate volume of purified water was added to carboxymethylstarch which was subsequently added to the above mixture, and the resulting mixture was kneaded and then subjected to granulation. After drying, the thus prepared granules were mixed with talc and magnesium stearate and subjected to tablet making in the usual way.

FORMULATION EXAMPLE 10

| (25 mg tablets) | |
|---|---|
| compound 68 | 25 mg |
| lactose | 122 mg |
| carboxymethylstarch | 50 mg |
| talc | 2 mg |
| magnesium stearate | 1 mg |
| | 200 mg/tablet |

The procedure of Formulation Example 9 was repeated to obtain 25 mg tablets.

FORMULATION EXAMPLE 11

| (10 mg capsules) | |
|---|---|
| compound 33 | 300 mg |
| lactose | 2000 mg |
| starch | 670 mg |
| gelatin | 30 mg |
| | 3000 mg |

Granules were prepared in accordance with the procedure described in Formulation Example 3 and packed in capsules in 100 mg portions.

FORMULATION EXAMPLE 12

| (10 mg capsules) | |
|---|---|
| compound 99 | 300 mg |
| lactose | 2000 mg |
| starch | 670 mg |
| gelatin | 30 mg |
| | 3000 mg |

The procedure of Formulation Example 11 was repeated to obtain 100 mg capsules.

FORMULATION EXAMPLE 13

| (0.1% injections) | |
|---|---|
| compound 32 | 10 mg |
| polyethylene glycol 400 | 3 ml |
| polysorbate 80 | 0.01 ml |
| distilled water for injection use | balance |
| | 10 ml |

The compound 32 was dissolved in a mixture solution of polyethylene glycol 400 and polysorbate 80, total volume of the resulting solution was adjusted to 10 ml by gradually adding distilled water for injection use and then the thus prepared solution was packed in an ampule aseptically.

FORMULATION EXAMPLE 14

| (0.1% injections) | |
|---|---|
| compound 59 | 10 mg |
| polyethylene glycol 400 | 3 ml |
| polysorbate 80 | 0.01 ml |
| distilled water for injection use | balance |
| | 10 ml |

The procedure of Formulation Example 13 was repeated to obtain 0.1% injections.

Thus, it is apparent that there has been provided, in accordance with the present invention, a novel 3- or 4-glycosyloxybenzopyran derivative which is useful in pharmaceutical preparations. Also provided are excellent antiallergic agents which have low toxicity and are useful for the treatment or prevention of immediate type and delayed type allergic diseases, particularly an excellent antiallergic agent which is highly effective on delayed type allergy that cannot be treated effectively with the prior art antiallergic agents.

While the invention has been described in detail and with reference to specific embodiments thereof, it will be apparent to one skilled in the art that various changes and modifications can be made therein without departing from the spirit and scope thereof.

What is claimed is:

1. A 3-glycosyloxybenzopyran derivative represented by the following formula (I)

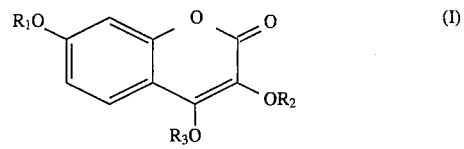

wherein $R_1$ is a hydrogen atom, an alkyl group, an alkenyl group, an aralkyl group or an acyl group, $R_2$ is a glycosyl group whose hydroxyl group is protected or not protected, which is selected from the group consisting of glucosyl, mannosyl and galactosyl groups, and $R_{33}$ is a hydrogen atom or a benzyl group, and physiologically acceptable salts thereof.

2. The 3-glycosyloxybenzopyran derivative and physiologically acceptable salts thereof as claimed in claim 1 wherein $R_2$ is a glucosyl group.

3. The 3-glycosyloxybenzopyran derivative and physiologically acceptable salts thereof as claimed in claim 1 wherein $R_2$ is a mannosyl group.

4. The 3-glycosyloxybenzopyran derivative and physiologically acceptable salts thereof as claimed in claim 1 wherein $R_2$ is a galactosyl group.

5. The 3-glycosyloxybenzopyran derivative and physiologically acceptable salts thereof as claimed in claim 1 wherein $R_2$ is an unprotected glycosyl group.

6. The 3-glycosyloxybenzopyran derivative and physiologically acceptable salts thereof as claimed in claim 1 wherein $R_2$ is a glycosyl group which is protected with an acyl or benzyl group.

7. The 3-glycosyloxybenzopyran derivative and physiologically acceptable salts thereof as claimed in any one of claims 1 to 6 wherein $R_1$ is a hydrogen atom, an alkyl group having 1 to 12 carbon atoms or an alkenyl group having 2 to 10 carbon atoms.

8. The 3-glycosyloxybenzopyran derivative and physiologically acceptable salts thereof as claimed in claim 7 wherein $R_3$ is a hydrogen atom.

9. The 3-glycosyloxybenzopyran derivative and physiologically acceptable salts thereof as claimed in claim 7 wherein $R_3$ is a benzyl group.

10. The 3-glycosyloxybenzopyran derivative and physiologically acceptable salts thereof as claimed in any one of claims 1 to 6 wherein $R_1$ is an aralkyl group which comprises a benzyl group, or an acyl group having 2 to 7 carbon atoms.

11. The 3-glycosyloxybenzopyran derivative and physiologically acceptable salts thereof as claimed in claim 10 wherein $R_3$ is a hydrogen atom.

12. The 3-glycosyloxybenzopyran derivative and physiologically acceptable salts thereof as claimed in claim 10 wherein $R_3$ is a benzyl group.

13. The 3-glycosyloxybenzopyran derivative and physiologically acceptable salts thereof as claimed in claim 1 wherein $R_1$ is an alkyl group having 1 to 12 carbon atoms and $R_3$ is a hydrogen atom.

14. A 4-glycosyloxybenzopyran derivative represented by the following formula (II)

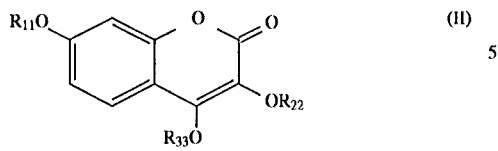

wherein $R_{11}$ is a hydrogen atom, an alkyl group, an alkenyl group, an aralkyl group or an acyl group, $R_{22}$ is a hydrogen atom or an acyl group and $R_{33}$ is a glycosyl group whose hydroxyl group is protected or not protected, which is selected from the group consisting of glucosyl, mannosyl and galactosyl groups, and physiologically acceptable salts thereof.

15. The 4-glycosyloxybenzopyran derivative and physiologically acceptable salts thereof as claimed in claim 14 wherein $R_{33}$ is a glucosyl group.

16. The 4-glycosyloxybenzopyran derivative and physiologically acceptable salts thereof as claimed in claim 14 wherein $R_{33}$ is a mannosyl group.

17. The 4-glycosyloxybenzopyran derivative and physiologically acceptable salts thereof as claimed in claim 14 wherein $R_{33}$ is a galactosyl group.

18. The 4-glycosyloxybenzopyran derivative and physiologically acceptable salts thereof as claimed in claim 14 wherein $R_{33}$ is an unprotected glycosyl group.

19. The 4-glycosyloxybenzopyran derivative and physiologically acceptable salts thereof as claimed in claim 14 wherein $R_{33}$ is a glycosyl group which is protected with an acyl or benzyl group.

20. The 4-glycosyloxybenzopyran derivative and physiologically acceptable salts thereof as claimed in any one of claims 14 to 19 wherein $R_{11}$ is a hydrogen atom, an alkyl group having 1 to 12 carbon atoms or an alkenyl group having 2 to 10 carbon atoms.

21. The 4-glycosyloxybenzopyran derivative and physiologically acceptable salts thereof as claimed in claim 20 wherein $R_{22}$ is a hydrogen atom.

22. The 4-glycosyloxybenzopyran derivative and physiologically acceptable salts thereof as claimed in claim 20 wherein $R_{22}$ is an acyl group having 2 to 7 carbon atoms.

23. The 4-glycosyloxybenzopyran derivative and physiologically acceptable salts thereof as claimed in any one of claims 14 to 19 wherein $R_{11}$ is an aralkyl group which comprises a benzyl group, or an acyl group having 2 to 7 carbon atoms.

24. The 4-glycosyloxybenzopyran derivative and physiologically acceptable salts thereof as claimed in claim 23 wherein $R_{22}$ is a hydrogen atom.

25. The 4-glycosyloxybenzopyran derivative and physiologically acceptable salts thereof as claimed in claim 23 wherein $R_{22}$ is an acyl group having 2 to 7 carbon atoms.

26. The 4-glycosyloxybenzopyran derivative and physiologically acceptable salts thereof as claimed in claim 14 wherein $R_{22}$ is an alkyl group having 1 to 12 carbon atoms and $R_{22}$ is a hydrogen atom.

27. An antiallergic composition comprising a therapeutically effective amount of the compound of formula (I) as recited in claim 1, or a pysiologically acceptable salt thereof, and pharmaceutically acceptable carriers.

28. An antiallergic composition as claimed in claim 27 wherein $R_2$ is a glucosyl group or a galactosyl group.

29. An antiallergic composition as claimed in claim 28 wherein $R_1$ is an alkyl group having 1 to 12 carbon atoms or an alkenyl group having 2 to 10 carbon atoms.

30. An antiallergic composition as claimed in claim 29 wherein $R_3$ is a hydrogen atom.

31. An antiallergic composition as claimed in claim 30 wherein $R_1$ is an alkyl group having 1 to 12 carbon atoms.

32. An antiallergic composition comprising a therapeutically effective amount of the compound of formula (II) as recited in claim 14, or a pysiologically acceptable salt thereof, and pharmaceutically acceptable carriers.

33. An antiallergic composition as claimed in claim 32 wherein $R_{33}$ is a glucosyl group or a galactosyl group.

34. An antiallergic composition as claimed in claim 33 wherein $R_{11}$ is an alkyl group having 1 to 12 carbon atoms or an alkenyl group having 2 to 10 carbon atoms.

35. An antiallergic composition as claimed in claim 34 wherein $R_{22}$ is a hydrogen atom.

36. An antiallergic composition as claimed in claim 35 wherein $R_{11}$ is an alkyl group having 1 to 12 carbon atoms.

37. A method for treating allergic diseases which comprises administering to a mammal in need of such treatment a therapeuticaly effective amount of the compound of formula (I) as recited in claim 1 or a pysiologically acceptable salt thereof.

38. A method for treating allergic diseases which comprises administering to a mammal in need of such treatment a therapeuticaly effective amount of the compound of formula (II) as recited in claim 14 or a pysiologically acceptable salt thereof.

* * * * *